United States Patent
Padmani et al.

(10) Patent No.: US 11,575,673 B2
(45) Date of Patent: Feb. 7, 2023

(54) CENTRAL USER MANAGEMENT IN A DISTRIBUTED HEALTHCARE INFORMATION MANAGEMENT SYSTEM

(71) Applicant: Baxter Corporation Englewood, Englewood, CO (US)

(72) Inventors: Bhavesh S. Padmani, Port Orange, FL (US); Matthew A. Valentine, Ormond Beach, FL (US); Robert Bossio, Palm Coast, FL (US)

(73) Assignee: Baxter Corporation Englewood, Englewood, CO (US)

( * ) Notice: Subject to any disclaimer, the term of this patent is extended or adjusted under 35 U.S.C. 154(b) by 511 days.

(21) Appl. No.: 14/868,646

(22) Filed: Sep. 29, 2015

(65) Prior Publication Data

US 2016/0092639 A1    Mar. 31, 2016

Related U.S. Application Data

(60) Provisional application No. 62/057,881, filed on Sep. 30, 2014.

(51) Int. Cl.
*G16H 10/60* (2018.01)
*G16H 40/20* (2018.01)
(Continued)

(52) U.S. Cl.
CPC .......... *H04L 63/10* (2013.01); *G06F 21/6245* (2013.01); *G16H 10/60* (2018.01);
(Continued)

(58) Field of Classification Search
CPC .............................................. G06Q 50/22–26
See application file for complete search history.

(56) References Cited

U.S. PATENT DOCUMENTS 641,748 A    1/1900  Smith
819,339 A    5/1906  Cleland
(Continued)

FOREIGN PATENT DOCUMENTS

CN    1516257    5/1999
CN    2440518    8/2001
(Continued)

OTHER PUBLICATIONS

Editor, "A short history of the computer password" As retrieved from https://www.welivesecurity.com/2017/05/04/short-history-computer-password/ May 4, 2017 (Year: 2017).*

(Continued)

*Primary Examiner* — Neal Sereboff
(74) *Attorney, Agent, or Firm* — K&L Gates LLP

(57) ABSTRACT

Centralized support user management in a distributed healthcare information management system. Support user management may include generation of permission data that may be distributed from a central server to one or more local systems. The local systems may execute a healthcare information management application such as, for example, a pharmacy workflow management application. In any regard, central support users at the central server may periodically require access to the local systems to perform, among other activities, technical support or troubleshooting in relation to the application executed at the local system. In turn, provision of permission data from the central server to the local system may allow support users to access the local system with specific permission identification's provided specific ones of the support users. In turn, specific user permissions may be established and support user tracking may be carried out at the local systems.

28 Claims, 26 Drawing Sheets

(51) Int. Cl.
*G16H 20/10* (2018.01)
*H04L 9/40* (2022.01)
*G06F 21/62* (2013.01)
*G16Z 99/00* (2019.01)
*H04L 67/01* (2022.01)
*H04L 67/51* (2022.01)

(52) U.S. Cl.
CPC ............ *G16H 20/10* (2018.01); *G16H 40/20* (2018.01); *G16Z 99/00* (2019.02); *H04L 67/01* (2022.05); *H04L 67/51* (2022.05)

(56) References Cited

U.S. PATENT DOCUMENTS

| | | |
|---|---|---|
| 3,426,150 A | 2/1969 | Tygart |
| 3,739,943 A | 6/1973 | Williamsen et al. |
| 3,742,938 A | 7/1973 | Stern |
| 3,756,752 A | 9/1973 | Stenner |
| 3,774,762 A | 11/1973 | Lichtenstein |
| 3,786,190 A | 1/1974 | Pori |
| 3,809,871 A | 5/1974 | Howard et al. |
| 3,810,102 A | 5/1974 | Parks, III et al. |
| 3,848,112 A | 11/1974 | Weichselbaum et al. |
| 3,858,574 A | 1/1975 | Page |
| 3,878,967 A | 4/1975 | Joslin et al. |
| 3,910,257 A | 10/1975 | Fletcher et al. |
| 3,910,260 A | 11/1975 | Sarnoff et al. |
| 3,921,196 A | 11/1975 | Patterson |
| 3,971,000 A | 7/1976 | Cromwell |
| 3,995,630 A | 12/1976 | Verrdonk |
| 3,998,103 A | 12/1976 | Bjorklund et al. |
| 4,032,908 A | 6/1977 | Rice et al. |
| 4,078,562 A | 3/1978 | Friedman |
| 4,144,496 A | 3/1979 | Cunningham et al. |
| 4,151,407 A | 4/1979 | McBride et al. |
| 4,156,867 A | 5/1979 | Bench et al. |
| 4,164,320 A | 8/1979 | Irazoqui et al. |
| 4,173,971 A | 11/1979 | Karz |
| 4,199,307 A | 4/1980 | Jassawalla |
| 4,270,532 A | 6/1981 | Franetzki et al. |
| 4,273,121 A | 6/1981 | Jassawalla |
| 4,282,872 A | 8/1981 | Franetzki et al. |
| 4,308,866 A | 1/1982 | Jelliffe et al. |
| 4,319,338 A | 3/1982 | Grudowski et al. |
| 4,320,757 A | 3/1982 | Whitney et al. |
| 4,354,252 A | 10/1982 | Lamb et al. |
| 4,369,780 A | 1/1983 | Sakai |
| 4,370,983 A | 2/1983 | Lichtenstein |
| 4,373,527 A | 2/1983 | Fischell |
| 4,381,776 A | 5/1983 | Latham, Jr. |
| 4,385,630 A | 5/1983 | Gilcher et al. |
| 4,398,289 A | 8/1983 | Schoate |
| 4,398,908 A | 8/1983 | Siposs |
| 4,414,566 A | 11/1983 | Peyton et al. |
| 4,416,654 A | 11/1983 | Schoendorfer et al. |
| 4,425,114 A | 1/1984 | Schoendorfer et al. |
| 4,428,381 A | 1/1984 | Hepp |
| 4,443,216 A | 4/1984 | Chappell |
| 4,447,224 A | 5/1984 | DeCant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,464,172 A | 8/1984 | Lichtenstein |
| 4,469,481 A | 9/1984 | Kobayashi |
| 4,475,901 A | 10/1984 | Kraegen et al. |
| 4,476,381 A | 10/1984 | Rubin |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,496,351 A | 1/1985 | Hillel et al. |
| 4,511,352 A | 4/1985 | Theeuwes et al. |
| 4,525,861 A | 6/1985 | Freeburg |
| 4,529,401 A | 7/1985 | Leslie et al. |
| 4,531,527 A | 7/1985 | Reinhold, Jr. et al. |
| 4,538,138 A | 8/1985 | Harvey et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,979 A | 12/1985 | Rosskopf |
| 4,561,443 A | 12/1985 | Hogrefe et al. |
| 4,562,751 A | 1/1986 | Nason |
| 4,564,054 A | 1/1986 | Gustavsson |
| 4,590,473 A | 5/1986 | Burke et al. |
| 4,602,249 A | 7/1986 | Abbott |
| 4,619,653 A | 10/1986 | Fischell |
| 4,622,979 A | 11/1986 | Katchis et al. |
| 4,624,661 A | 11/1986 | Arimond |
| 4,636,950 A | 1/1987 | Caswell et al. |
| 4,637,817 A | 1/1987 | Archibald et al. |
| 4,650,469 A | 3/1987 | Berg et al. |
| 4,652,262 A | 3/1987 | Veracchi |
| 4,653,010 A | 3/1987 | Figler et al. |
| 4,676,776 A | 6/1987 | Howson |
| 4,681,563 A | 7/1987 | Deckert et al. |
| 4,688,167 A | 8/1987 | Agarwal |
| 4,691,580 A | 9/1987 | Fosslien |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,705,506 A | 11/1987 | Archibald |
| D293,135 S | 12/1987 | Medema et al. |
| 4,714,462 A | 12/1987 | DiComenico |
| 4,717,042 A | 1/1988 | McLaughlin |
| 4,718,576 A | 1/1988 | Tamura et al. |
| 4,722,224 A | 2/1988 | Scheller et al. |
| 4,722,349 A | 2/1988 | Baumberg |
| 4,722,734 A | 2/1988 | Kolln |
| 4,730,849 A | 3/1988 | Siegel |
| 4,731,058 A | 3/1988 | Doan |
| 4,732,411 A | 3/1988 | Siegel |
| 4,741,732 A | 5/1988 | Crankshaw et al. |
| 4,741,736 A | 5/1988 | Brown |
| 4,756,706 A | 7/1988 | Kerns et al. |
| 4,759,756 A | 7/1988 | Forman |
| 4,778,449 A | 10/1988 | Weber et al. |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,644 A | 1/1989 | Polaschegg |
| 4,797,840 A | 1/1989 | Fraden |
| 4,803,625 A | 2/1989 | Fu et al. |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,828,545 A | 5/1989 | Epstein et al. |
| 4,829,524 A | 5/1989 | Yoshida |
| 4,830,018 A | 5/1989 | Treach |
| 4,831,562 A | 5/1989 | Mcintosh et al. |
| 4,832,033 A | 5/1989 | Maher et al. |
| 4,835,372 A | 5/1989 | Gombrich et al. |
| 4,835,521 A | 5/1989 | Andrejasich et al. |
| 4,838,275 A | 6/1989 | Lee |
| 4,839,806 A | 6/1989 | Goldfischer et al. |
| 4,845,644 A | 7/1989 | Anthias et al. |
| 4,847,764 A | 7/1989 | Halvorson |
| 4,850,009 A | 7/1989 | Zook et al. |
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,889,132 A | 12/1989 | Hutcheson et al. |
| 4,889,134 A | 12/1989 | Greenwold et al. |
| 4,893,270 A | 1/1990 | Beck et al. |

(56) References Cited

U.S. PATENT DOCUMENTS

| | | |
|---|---|---|
| 4,897,777 A | 1/1990 | Janke et al. |
| 4,898,209 A | 2/1990 | Zbed |
| 4,898,576 A | 2/1990 | Philip |
| 4,898,578 A | 2/1990 | Rubalcaba, Jr. |
| 4,901,728 A | 2/1990 | Hutchison |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,925,444 A | 5/1990 | Orkin et al. |
| 4,933,843 A | 6/1990 | Scheller et al. |
| 4,937,777 A | 6/1990 | Flood et al. |
| 4,941,808 A | 7/1990 | Qureshi et al. |
| 4,943,279 A | 7/1990 | Samiotes et al. |
| 4,946,445 A | 8/1990 | Lynn |
| 4,949,274 A | 8/1990 | Hollander et al. |
| 4,952,928 A | 8/1990 | Carroll et al. |
| 4,953,074 A | 8/1990 | Kametani et al. |
| 4,960,230 A | 10/1990 | Marelli |
| 4,966,579 A | 10/1990 | Polaschegg |
| 4,967,928 A | 11/1990 | Carter |
| 4,968,295 A | 11/1990 | Neumann |
| 4,977,590 A | 12/1990 | Milovancevic |
| 4,978,335 A | 12/1990 | Arthur, III |
| 4,991,091 A | 2/1991 | Allen |
| 4,992,926 A | 2/1991 | Janke et al. |
| 4,993,068 A | 2/1991 | Piosenka et al. |
| 4,993,506 A | 2/1991 | Angel |
| 4,998,249 A | 3/1991 | Bennett et al. |
| 5,002,055 A | 3/1991 | Merki et al. |
| 5,003,296 A | 3/1991 | Lee |
| 5,006,699 A | 4/1991 | Felkner et al. |
| 5,007,429 A | 4/1991 | Treatch et al. |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,959 A | 9/1991 | Phillips et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,061,243 A | 10/1991 | Winchell et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,078,683 A | 1/1992 | Sancoff et al. |
| 5,084,828 A | 1/1992 | Kaufman et al. |
| 5,087,245 A | 2/1992 | Doan |
| 5,088,904 A | 2/1992 | Okada |
| 5,088,981 A | 2/1992 | Howson et al. |
| 5,088,990 A | 2/1992 | Hivale et al. |
| 5,096,385 A | 3/1992 | Georgi et al. |
| 5,098,377 A | 3/1992 | Borsanyi et al. |
| 5,100,380 A | 3/1992 | Epstein et al. |
| 5,100,394 A | 3/1992 | Dudar et al. |
| 5,104,374 A | 4/1992 | Bishko et al. |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,116,203 A | 5/1992 | Natwick et al. |
| 5,116,312 A | 5/1992 | Blankenship et al. |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,169,642 A | 12/1992 | Brinker et al. |
| 5,172,698 A | 12/1992 | Stanko |
| 5,176,004 A | 1/1993 | Gaudet |
| 5,179,569 A | 1/1993 | Sawyer |
| 5,179,700 A | 1/1993 | Aihara et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,208,762 A | 5/1993 | Charhut et al. |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,225,974 A | 7/1993 | Mathews et al. |
| 5,226,425 A | 7/1993 | Righter |
| 5,228,450 A | 7/1993 | Sellers |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,704 A | 9/1993 | Weber et al. |
| 5,254,096 A | 10/1993 | Rondelet et al. |
| 5,256,156 A | 10/1993 | Kern et al. |
| 5,256,157 A | 10/1993 | Samiotes et al. |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,277,188 A | 1/1994 | Selker |
| 5,283,861 A | 2/1994 | Dangler et al. |
| 5,284,150 A | 2/1994 | Butterfield et al. |
| 5,286,252 A | 2/1994 | Tuttle et al. |
| 5,292,029 A | 3/1994 | Pearson |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |
| 5,324,422 A | 6/1994 | Colleran et al. |
| 5,325,478 A | 6/1994 | Shelton et al. |
| 5,327,341 A | 7/1994 | Whalen et al. |
| 5,331,549 A | 7/1994 | Crawford, Jr. |
| 5,336,245 A | 8/1994 | Adams et al. |
| 5,337,230 A | 8/1994 | Baumgartner et al. |
| 5,337,919 A | 8/1994 | Spaulding et al. |
| 5,338,157 A | 8/1994 | Blomquist |
| 5,339,421 A | 8/1994 | Housel, III |
| 5,339,821 A | 8/1994 | Fujimoto |
| 5,341,291 A | 8/1994 | Roizen et al. |

(56) References Cited

U.S. PATENT DOCUMENTS

| | | |
|---|---|---|
| 5,341,412 A | 8/1994 | Ramot et al. |
| 5,348,008 A | 9/1994 | Bornn et al. |
| 5,348,539 A | 9/1994 | Herskowitz |
| 5,349,675 A | 9/1994 | Fitzgerald et al. |
| 5,356,378 A | 10/1994 | Doan |
| 5,361,202 A | 11/1994 | Doue |
| 5,361,758 A | 11/1994 | Hall et al. |
| 5,366,896 A | 11/1994 | Margrey et al. |
| 5,366,904 A | 11/1994 | Qureshi et al. |
| 5,367,555 A | 11/1994 | Isoyama |
| 5,368,562 A | 11/1994 | Blomquist et al. |
| 5,370,612 A | 12/1994 | Maeda et al. |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Purvis et al. |
| 5,377,864 A | 1/1995 | Blechl et al. |
| 5,378,231 A | 1/1995 | Johnson et al. |
| 5,379,214 A | 1/1995 | Arbuckle et al. |
| 5,389,078 A | 2/1995 | Zalesky et al. |
| 5,390,238 A | 2/1995 | Kirk et al. |
| 5,392,951 A | 2/1995 | Gardner et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,404,292 A | 4/1995 | Hendrickson |
| 5,404,384 A | 4/1995 | Colburn et al. |
| 5,406,473 A | 4/1995 | Yoshikura et al. |
| 5,412,715 A | 5/1995 | Volpe |
| 5,415,167 A | 5/1995 | Wilk |
| 5,416,695 A | 5/1995 | Stutman et al. |
| 5,417,222 A | 5/1995 | Dempsey et al. |
| 5,420,977 A | 5/1995 | Sztipanovits et al. |
| 5,421,343 A | 6/1995 | Feng |
| 5,423,746 A | 6/1995 | Burkett et al. |
| 5,429,602 A | 7/1995 | Hauser |
| 5,431,201 A | 7/1995 | Torchia et al. |
| 5,431,299 A | 7/1995 | Brewer et al. |
| 5,431,627 A | 7/1995 | Pastrone et al. |
| 5,433,736 A | 7/1995 | Nilsson |
| 5,438,607 A | 8/1995 | Przygoda, Jr. et al. |
| 5,440,699 A | 8/1995 | Farrand et al. |
| 5,441,047 A | 8/1995 | David et al. |
| 5,445,294 A | 8/1995 | Gardner et al. |
| 5,445,621 A | 8/1995 | Poli et al. |
| 5,446,868 A | 8/1995 | Gardea, II et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,469,855 A | 11/1995 | Pompei et al. |
| 5,471,382 A | 11/1995 | Tallman et al. |
| 5,474,552 A | 12/1995 | Palti |
| 5,482,043 A | 1/1996 | Zulauf |
| 5,482,446 A | 1/1996 | Williamson et al. |
| 5,485,408 A | 1/1996 | Blomquist |
| 5,490,610 A | 2/1996 | Pearson |
| 5,494,592 A | 2/1996 | Latham, Jr. et al. |
| 5,496,265 A | 3/1996 | Langley et al. |
| 5,496,273 A | 3/1996 | Pastrone et al. |
| 5,502,944 A | 4/1996 | Kraft et al. |
| 5,507,412 A | 4/1996 | Ebert et al. |
| 5,508,912 A | 4/1996 | Schneiderman |
| 5,509,318 A | 4/1996 | Gomes |
| 5,509,422 A | 4/1996 | Fukami |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,522,396 A | 6/1996 | Langer et al. |
| 5,522,798 A | 6/1996 | Johnson et al. |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,542,420 A | 8/1996 | Goldman et al. |
| 5,544,649 A | 8/1996 | David et al. |
| 5,544,651 A | 8/1996 | Wilk |
| 5,544,661 A | 8/1996 | Davis et al. |
| 5,545,140 A | 8/1996 | Conero et al. |
| 5,546,580 A | 8/1996 | Seliger et al. |
| 5,547,470 A | 8/1996 | Johnson et al. |
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,571,258 A | 11/1996 | Pearson |
| 5,573,502 A | 11/1996 | LeCocq et al. |
| 5,573,506 A | 11/1996 | Vasko |
| 5,575,632 A | 11/1996 | Morris et al. |
| 5,576,952 A | 11/1996 | Stutman et al. |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | Mcilroy et al. |
| 5,588,815 A | 12/1996 | Zaleski, II |
| 5,589,932 A | 12/1996 | Garcia-Rubio et al. |
| 5,590,648 A | 1/1997 | Mitchell et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,609,575 A | 3/1997 | Larson et al. |
| 5,609,576 A | 3/1997 | Voss et al. |
| 5,613,115 A | 3/1997 | Gihl et al. |
| 5,619,428 A | 4/1997 | Lee et al. |
| 5,619,991 A | 4/1997 | Sloane |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,641,628 A | 6/1997 | Bianchi |

(56) References Cited

U.S. PATENT DOCUMENTS

| | | |
|---|---|---|
| 5,643,193 A | 7/1997 | Papillon et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |
| 5,661,978 A | 9/1997 | Holmes et al. |
| 5,664,270 A | 9/1997 | Bell et al. |
| 5,666,404 A | 9/1997 | Ciccotelli et al. |
| D385,646 S | 10/1997 | Chan |
| 5,678,562 A | 10/1997 | Sellers |
| 5,678,568 A | 10/1997 | Uchikubo et al. |
| 5,681,285 A | 10/1997 | Ford et al. |
| 5,682,526 A | 10/1997 | Smokoff et al. |
| 5,683,367 A | 11/1997 | Jordan et al. |
| 5,685,844 A | 11/1997 | Marttila |
| 5,687,717 A | 11/1997 | Halpern |
| 5,687,734 A | 11/1997 | Dempsey et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,724,025 A | 3/1998 | Tavori |
| 5,724,580 A | 3/1998 | Levin et al. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,758,095 A | 5/1998 | Albaum et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,778,345 A | 7/1998 | McCartney |
| 5,778,882 A | 7/1998 | Raymond et al. |
| 5,781,442 A | 7/1998 | Engleson et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,790,409 A | 8/1998 | Fedor et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,801,755 A | 9/1998 | Echerer |
| 5,803,906 A | 9/1998 | Pratt et al. |
| 5,805,442 A | 9/1998 | Crater et al. |
| 5,805,454 A | 9/1998 | Valerino et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Russo et al. |
| 5,810,747 A | 9/1998 | Brudny et al. |
| 5,812,410 A | 9/1998 | Lion et al. |
| 5,814,015 A | 9/1998 | Gargano et al. |
| 5,815,566 A | 9/1998 | Ramot et al. |
| 5,818,528 A | 10/1998 | Roth et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,832,447 A | 11/1998 | Rieker et al. |
| 5,832,448 A | 11/1998 | Brown |
| 5,832,450 A | 11/1998 | Myers et al. |
| 5,833,599 A | 11/1998 | Schrier et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,848,593 A | 12/1998 | McGrady et al. |
| 5,851,186 A | 12/1998 | Wood et al. |
| 5,852,590 A | 12/1998 | De La Huerga |
| 5,853,387 A | 12/1998 | Clegg et al. |
| 5,855,550 A | 1/1999 | Lai et al. |
| 5,857,967 A | 1/1999 | Frid et al. |
| 5,859,972 A | 1/1999 | Subramaniam et al. |
| 5,865,745 A | 2/1999 | Schmitt et al. |
| 5,865,786 A | 2/1999 | Sibalis et al. |
| 5,867,821 A | 2/1999 | Ballantyne et al. |
| 5,871,465 A | 2/1999 | Vasko |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,884,273 A | 3/1999 | Sattizahn et al. |
| 5,884,457 A | 3/1999 | Ortiz et al. |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zimi et al. |
| 5,894,273 A | 4/1999 | Meador et al. |
| 5,895,371 A | 4/1999 | Levitas et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Jhuboo et al. |
| 5,904,668 A | 5/1999 | Hyman et al. |
| 5,905,653 A | 5/1999 | Higham et al. |
| 5,907,291 A | 5/1999 | Chen et al. |
| 5,907,493 A | 5/1999 | Boyer et al. |
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sato et al. |
| 5,912,818 A | 6/1999 | McGrady et al. |
| 5,913,197 A | 6/1999 | Kameda |
| 5,913,310 A | 6/1999 | Brown |
| 5,915,089 A | 6/1999 | Stevens et al. |
| 5,915,240 A | 6/1999 | Karpf |
| 5,919,154 A | 7/1999 | Toavs et al. |
| 5,921,938 A | 7/1999 | Aoyama et al. |
| 5,923,018 A | 7/1999 | Kameda et al. |
| 5,924,074 A | 7/1999 | Evans |
| 5,924,103 A | 7/1999 | Ahmed et al. |
| 5,927,540 A | 7/1999 | Godlewski |
| 5,931,791 A | 8/1999 | Saltzstein et al. |

(56) References Cited

U.S. PATENT DOCUMENTS

| | | |
|---|---|---|
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |
| 5,941,829 A | 8/1999 | Saltzstein et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,945,651 A | 8/1999 | Chorosinski et al. |
| 5,946,083 A | 8/1999 | Melendez et al. |
| 5,946,659 A | 8/1999 | Lancelot et al. |
| D414,578 S | 9/1999 | Chen et al. |
| 5,950,006 A | 9/1999 | Crater et al. |
| 5,951,300 A | 9/1999 | Brown |
| 5,951,510 A | 9/1999 | Barak |
| 5,954,640 A | 9/1999 | Szabo |
| 5,954,885 A | 9/1999 | Bollish et al. |
| 5,954,971 A | 9/1999 | Pages et al. |
| 5,956,023 A | 9/1999 | Lyle et al. |
| 5,957,885 A | 9/1999 | Bollish et al. |
| 5,959,529 A | 9/1999 | Kail, IV |
| 5,960,085 A | 9/1999 | de la Huerga |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,963,641 A | 10/1999 | Crandall et al. |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,490 A | 11/1999 | Tsoukalis |
| 5,983,193 A | 11/1999 | Heinonen et al. |
| 5,987,519 A | 11/1999 | Peifer et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,965 A | 11/1999 | Experton |
| 5,997,167 A | 12/1999 | Crater et al. |
| 5,997,476 A | 12/1999 | Brown |
| 6,003,006 A | 12/1999 | Colella et al. |
| 6,004,020 A | 12/1999 | Bartur |
| 6,004,276 A | 12/1999 | Wright et al. |
| 6,006,191 A | 12/1999 | DeRienzo |
| 6,006,946 A | 12/1999 | Williams et al. |
| 6,009,333 A | 12/1999 | Chaco |
| 6,010,454 A | 1/2000 | Arieff et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,021,392 A | 2/2000 | Lester et al. |
| 6,022,315 A | 2/2000 | Iliff |
| 6,023,522 A | 2/2000 | Draganoff et al. |
| 6,024,539 A | 2/2000 | Blomquist |
| 6,024,699 A | 2/2000 | Surwit et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Holowko et al. |
| 6,039,467 A | 3/2000 | Holmes |
| 6,047,259 A | 4/2000 | Campbell et al. |
| 6,048,086 A | 4/2000 | Valerino |
| 6,050,940 A | 4/2000 | Braun et al. |
| 6,055,487 A | 4/2000 | Margery et al. |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,068,153 A | 5/2000 | Young et al. |
| 6,068,156 A | 5/2000 | Liff et al. |
| 6,073,046 A | 6/2000 | Patel et al. |
| 6,074,345 A | 6/2000 | van Oostrom et al. |
| 6,079,621 A | 6/2000 | Vardanyan et al. |
| 6,080,106 A | 6/2000 | Lloyd et al. |
| 6,081,048 A | 6/2000 | Bergmann et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,096,561 A | 8/2000 | Tayi |
| 6,098,892 A | 8/2000 | Peoples, Jr. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,940 A | 9/2000 | Mjalli |
| 6,123,524 A | 9/2000 | Danby et al. |
| 6,125,350 A | 9/2000 | Dirbas |
| 6,129,517 A | 10/2000 | Danby et al. |
| 6,132,371 A | 10/2000 | Dempsey et al. |
| 6,134,504 A | 10/2000 | Douglas et al. |
| 6,135,949 A | 10/2000 | Russo et al. |
| 6,139,495 A | 10/2000 | De La Huerga |
| 6,141,412 A | 10/2000 | Smith et al. |
| 6,144,922 A | 11/2000 | Douglas et al. |
| 6,145,695 A | 11/2000 | Garrigues |
| 6,146,523 A | 11/2000 | Kenley et al. |
| 6,148,297 A | 11/2000 | Swor et al. |
| 6,149,063 A | 11/2000 | Reynolds et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |
| 6,160,478 A | 12/2000 | Jacobsen et al. |
| 6,161,095 A | 12/2000 | Brown |
| 6,161,141 A | 12/2000 | Dillon |
| 6,163,737 A | 12/2000 | Fedor et al. |
| 6,165,154 A | 12/2000 | Gray et al. |
| 6,168,563 B1 | 1/2001 | Brown |
| 6,170,007 B1 | 1/2001 | Venkatraman et al. |
| 6,170,746 B1 | 1/2001 | Brook et al. |
| 6,171,112 B1 | 1/2001 | Clark et al. |
| 6,171,237 B1 | 1/2001 | Avitall et al. |
| 6,171,264 B1 | 1/2001 | Bader |
| 6,173,198 B1 | 1/2001 | Schulze et al. |
| 6,175,779 B1 | 1/2001 | Barrett |
| 6,175,977 B1 | 1/2001 | Schumacher et al. |
| 6,176,392 B1 | 1/2001 | William et al. |
| 6,182,047 B1 | 1/2001 | Dirbas |
| 6,183,417 B1 | 2/2001 | Geheb et al. |
| 6,186,145 B1 | 2/2001 | Brown |
| 6,192,320 B1 | 2/2001 | Margrey et al. |
| 6,193,480 B1 | 2/2001 | Butterfield |
| 6,195,887 B1 | 3/2001 | Danby et al. |
| 6,198,394 B1 | 3/2001 | Jacobsen et al. |
| 6,200,264 B1 | 3/2001 | Satherley et al. |

(56) References Cited

U.S. PATENT DOCUMENTS

| | | |
|---|---|---|
| 6,200,289 B1 | 3/2001 | Hochman et al. |
| 6,202,923 B1 | 3/2001 | Boyer et al. |
| 6,203,495 B1 | 3/2001 | Bardy |
| 6,203,528 B1 | 3/2001 | Deckert et al. |
| 6,206,238 B1 | 3/2001 | Ophardt |
| 6,206,829 B1 | 3/2001 | Iliff |
| 6,210,361 B1 | 4/2001 | Kamen et al. |
| 6,213,391 B1 | 4/2001 | Lewis |
| 6,213,738 B1 | 4/2001 | Danby et al. |
| 6,219,439 B1 | 4/2001 | Burger |
| 6,219,587 B1 | 4/2001 | Ahlin et al. |
| 6,221,011 B1 | 4/2001 | Bardy |
| 6,221,012 B1 | 4/2001 | Maschke et al. |
| 6,222,619 B1 | 4/2001 | Herron et al. |
| 6,224,549 B1 | 5/2001 | Drongelen |
| 6,225,901 B1 | 5/2001 | Kail, IV |
| 6,226,564 B1 | 5/2001 | Stuart |
| 6,226,745 B1 | 5/2001 | Wiederhold |
| 6,230,927 B1 | 5/2001 | Schoonen et al. |
| 6,234,997 B1 | 5/2001 | Kamen et al. |
| 6,245,013 B1 | 6/2001 | Minoz et al. |
| 6,246,473 B1 | 6/2001 | Smith, Jr. et al. |
| 6,248,063 B1 | 6/2001 | Barnhill et al. |
| 6,248,065 B1 | 6/2001 | Brown |
| 6,255,951 B1 | 7/2001 | De La Huerga |
| 6,256,643 B1 | 7/2001 | Cork et al. |
| 6,256,967 B1 | 7/2001 | Hebron et al. |
| 6,259,355 B1 | 7/2001 | Chaco et al. |
| 6,259,654 B1 | 7/2001 | De La Huerga |
| 6,266,645 B1 | 7/2001 | Simpson |
| 6,269,340 B1 | 7/2001 | Ford et al. |
| D446,854 S | 8/2001 | Cheney, II et al. |
| 6,270,455 B1 | 8/2001 | Brown |
| 6,270,457 B1 | 8/2001 | Bardy |
| 6,272,394 B1 | 8/2001 | Lipps |
| 6,272,505 B1 | 8/2001 | De La Huerga |
| 6,277,072 B1 | 8/2001 | Bardy |
| 6,283,322 B1 | 9/2001 | Lift et al. |
| 6,283,944 B1 | 9/2001 | McMullen et al. |
| 6,290,646 B1 | 9/2001 | Cosentino et al. |
| 6,290,650 B1 | 9/2001 | Butterfield et al. |
| 6,294,999 B1 | 9/2001 | Yarin et al. |
| 6,295,506 B1 | 9/2001 | Heinonen |
| 6,304,788 B1 | 10/2001 | Eady et al. |
| 6,306,088 B1 | 10/2001 | Krausman et al. |
| 6,307,956 B1 | 10/2001 | Black |
| 6,308,171 B1 | 10/2001 | De La Huerga |
| 6,311,163 B1 | 10/2001 | Sheehan et al. |
| 6,312,227 B1 | 11/2001 | Davis |
| 6,312,378 B1 | 11/2001 | Bardy |
| 6,314,384 B1 | 11/2001 | Goetz |
| 6,317,719 B1 | 11/2001 | Schrier et al. |
| 6,319,200 B1 | 11/2001 | Lai et al. |
| 6,321,203 B1 | 11/2001 | Kameda |
| 6,322,504 B1 | 11/2001 | Kirshner |
| 6,322,515 B1 | 11/2001 | Goor et al. |
| 6,330,491 B1 | 12/2001 | Lion |
| RE37,531 E | 1/2002 | Chaco et al. |
| 6,337,631 B1 | 1/2002 | Pai et al. |
| 6,338,007 B1 | 1/2002 | Broadfield et al. |
| 6,339,732 B1 | 1/2002 | Phoon et al. |
| 6,345,260 B1 | 2/2002 | Cummings, Jr. et al. |
| 6,346,886 B1 | 2/2002 | De La Huerga |
| 6,352,200 B1 | 3/2002 | Schoonen et al. |
| 6,353,817 B1 | 3/2002 | Jacobs et al. |
| 6,358,225 B1 | 3/2002 | Butterfield |
| 6,358,237 B1 | 3/2002 | Paukovits et al. |
| 6,361,263 B1 | 3/2002 | Dewey et al. |
| 6,362,591 B1 | 3/2002 | Moberg |
| 6,363,282 B1 | 3/2002 | Nichols et al. |
| 6,363,290 B1 | 3/2002 | Lyle et al. |
| 6,364,834 B1 | 4/2002 | Reuss et al. |
| 6,368,273 B1 | 4/2002 | Brown |
| 6,370,841 B1 | 4/2002 | Chudy et al. |
| 6,381,577 B1 | 4/2002 | Brown |
| 6,385,505 B1 | 5/2002 | Lipps |
| 6,393,369 B1 | 5/2002 | Carr |
| 6,397,190 B1 | 5/2002 | Goetz |
| 6,402,702 B1 | 6/2002 | Gilcher et al. |
| 6,406,426 B1 | 6/2002 | Reuss et al. |
| 6,407,335 B1 | 6/2002 | Franklin-Lees et al. |
| 6,408,330 B1 | 6/2002 | DeLaHuerga |
| 6,416,471 B1 | 7/2002 | Kumar et al. |
| 6,421,650 B1 | 7/2002 | Goetz et al. |
| 6,427,088 B1 | 7/2002 | Bowman, IV et al. |
| 6,434,531 B1 | 8/2002 | Lancelot et al. |
| 6,434,569 B1 | 8/2002 | Tomlinson et al. |
| 6,438,451 B1 | 8/2002 | Lion |
| RE37,829 E | 9/2002 | Charhut et al. |
| 6,449,927 B2 | 9/2002 | Hebron et al. |
| 6,450,956 B1 | 9/2002 | Rappaport et al. |
| 6,458,102 B1 | 10/2002 | Mann et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,511,138 B1 | 1/2003 | Gardner et al. |
| 6,519,569 B1 | 2/2003 | White et al. |
| 6,537,244 B2 | 3/2003 | Paukovits |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,564,121 B1 | 5/2003 | Wallace et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,581,069 B1 | 6/2003 | Robinson et al. |
| 6,581,798 B2 | 6/2003 | Liff et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O'Mahony et al. |
| 6,592,551 B1 | 7/2003 | Cobb |
| 6,593,528 B2 | 7/2003 | Franklin-Lees et al. |
| 6,607,485 B2 | 8/2003 | Bardy |
| 6,610,973 B1 | 8/2003 | Davis, III |
| 6,613,009 B1 | 9/2003 | Bainbridge et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,673,314 B1 | 1/2004 | Burbank et al. |
| 6,687,546 B2 | 1/2004 | Lebel et al. |
| 6,689,091 B2 | 2/2004 | Bui et al. |
| 6,694,191 B2 | 2/2004 | Starkweather et al. |
| 6,694,334 B2 | 2/2004 | DuLong et al. |
| 6,711,460 B1 | 3/2004 | Reese |
| 6,731,324 B2 | 5/2004 | Levy |
| 6,733,447 B2 | 5/2004 | Lai et al. |
| 6,735,497 B2 | 5/2004 | Wallace et al. |
| 6,740,075 B2 | 5/2004 | Lebel et al. |
| 6,746,398 B2 | 6/2004 | Hervy et al. |
| 6,758,810 B2 | 7/2004 | Lebel et al. |
| 6,768,425 B2 | 7/2004 | Flaherty et al. |
| 6,771,369 B2 | 8/2004 | Rzasa et al. |
| 6,775,602 B2 | 8/2004 | Gordon, Jr. et al. |

(56) References Cited

U.S. PATENT DOCUMENTS

| | | | |
|---|---|---|---|
| 6,776,304 B2 | 8/2004 | Liff et al. |
| 6,790,198 B1 | 9/2004 | White et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,707 B2 | 11/2004 | Rovatti et al. |
| 6,813,473 B1 | 11/2004 | Bruker |
| 6,813,519 B2 | 11/2004 | Lebel et al. |
| 6,814,255 B2 | 11/2004 | Liff et al. |
| 6,820,093 B2 | 11/2004 | De La Huerga |
| 6,842,736 B1 | 1/2005 | Brzozowski |
| 6,847,861 B2 | 1/2005 | Lunak et al. |
| 6,854,088 B2 | 2/2005 | Massengale et al. |
| 6,871,211 B2 | 3/2005 | Labounty et al. |
| 6,873,268 B2 | 3/2005 | Lebel et al. |
| 6,877,530 B2 | 4/2005 | Osborne et al. |
| 6,880,034 B2 | 4/2005 | Manke et al. |
| 6,885,288 B2 | 4/2005 | Pincus |
| 6,892,941 B2 | 5/2005 | Rosenblum |
| 6,912,549 B2 | 6/2005 | Rotter et al. |
| 6,913,590 B2 | 7/2005 | Sorenson et al. |
| 6,915,823 B2 | 7/2005 | Osborne et al. |
| 6,928,452 B2 | 8/2005 | De La Huerga |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 6,975,924 B2 | 12/2005 | Kircher et al. |
| 6,976,628 B2 | 12/2005 | Krupa |
| 6,979,306 B2 | 12/2005 | Moll |
| 6,980,958 B1 | 12/2005 | Surwit et al. |
| 6,981,644 B2 | 1/2006 | Cheong et al. |
| 6,985,870 B2 | 1/2006 | Martucci et al. |
| 6,991,002 B2 | 1/2006 | Osborne et al. |
| 6,995,664 B1 | 2/2006 | Darling |
| 7,006,893 B2 | 2/2006 | Hart et al. |
| 7,015,806 B2 | 3/2006 | Naidoo et al. |
| 7,017,622 B2 | 3/2006 | Osborne et al. |
| 7,017,623 B2 | 3/2006 | Tribble et al. |
| 7,028,723 B1 | 4/2006 | Alouani et al. |
| 7,096,212 B2 | 8/2006 | Tribble et al. |
| 7,117,902 B2 | 10/2006 | Osborne |
| 7,151,982 B2 | 12/2006 | Liff et al. |
| 7,194,336 B2 | 3/2007 | DiGianfilippo et al. |
| 7,209,891 B1 | 4/2007 | Addy et al. |
| 7,240,699 B2 | 7/2007 | Osborne et al. |
| 7,277,579 B2 | 10/2007 | Huang |
| 7,277,757 B2 | 10/2007 | Casavant et al. |
| 7,317,967 B2 | 1/2008 | DiGianfilippo et al. |
| 7,343,224 B2 | 3/2008 | DiGianfilippo et al. |
| 7,403,901 B1 | 7/2008 | Carley et al. |
| 7,427,002 B2 | 9/2008 | Liff et al. |
| 7,493,263 B2 | 2/2009 | Helmus et al. |
| 7,499,581 B2 | 3/2009 | Tribble et al. |
| 7,555,557 B2 | 6/2009 | Bradley et al. |
| 7,561,312 B1 | 7/2009 | Proudfoot et al. |
| 7,581,953 B2 | 9/2009 | Lehmann et al. |
| 7,599,516 B2 | 10/2009 | Limer et al. |
| 7,610,115 B2 | 10/2009 | Rob et al. |
| 7,630,908 B1 | 12/2009 | Amrien et al. |
| 7,636,718 B1 | 12/2009 | Steen et al. |
| 7,672,859 B1 | 3/2010 | Louie et al. |
| 7,698,019 B2 | 4/2010 | Moncrief et al. |
| 7,734,478 B2 | 6/2010 | Goodall et al. |
| 7,753,085 B2 | 7/2010 | Tribble et al. |
| 7,769,601 B1 | 8/2010 | Bleser et al. |
| 7,783,383 B2 | 8/2010 | Eliuk et al. |
| D624,225 S | 9/2010 | Federico et al. |
| 7,801,642 B2 | 9/2010 | Ansari et al. |
| 7,847,970 B1 | 12/2010 | McGrady |
| 7,853,621 B2 | 12/2010 | Guo |
| 7,931,859 B2 | 4/2011 | Mlodzinski et al. |
| 7,937,290 B2 | 5/2011 | Bahir |
| 7,986,369 B1 | 7/2011 | Burns |
| 7,991,507 B2 | 8/2011 | Liff et al. |
| 8,170,271 B2 | 5/2012 | Chen |
| 8,191,339 B2 | 6/2012 | Tribble et al. |
| 8,215,557 B1 | 7/2012 | Reno et al. |
| 8,220,503 B2 | 7/2012 | Tribble et al. |
| 8,225,824 B2 | 7/2012 | Eliuk et al. |
| D667,961 S | 9/2012 | Marmier |
| 8,267,129 B2 | 9/2012 | Doherty et al. |
| 8,271,138 B2 | 9/2012 | Eliuk et al. |
| 8,280,549 B2 | 10/2012 | Liff et al. |
| 8,284,305 B2 | 10/2012 | Newcomb et al. |
| 8,374,887 B1 | 2/2013 | Alexander |
| 8,386,070 B2 | 2/2013 | Eliuk et al. |
| 8,548,824 B1 | 10/2013 | daCosta |
| 8,554,579 B2 | 10/2013 | Tribble et al. |
| D693,480 S | 11/2013 | Spiess et al. |
| 8,595,206 B1 | 11/2013 | Ansari |
| 8,666,541 B1 | 3/2014 | Ansari et al. |
| 8,678,047 B2 | 3/2014 | Tribble et al. |
| D715,958 S | 10/2014 | Bossart et al. |
| 9,053,218 B2 | 6/2015 | Osborne et al. |
| D733,480 S | 7/2015 | Shao |
| D738,152 S | 9/2015 | Grasselli et al. |
| 9,272,796 B1* | 3/2016 | Chudy ................. G07G 1/0045 |
| D753,428 S | 4/2016 | Shao |
| 9,362,969 B1 | 6/2016 | Burgess et al. |
| 9,382,021 B2 | 7/2016 | Tribble et al. |
| 9,662,273 B2 | 5/2017 | Ranalletta et al. |
| 9,930,297 B2 | 3/2018 | Alexander et al. |
| 9,956,145 B2 | 5/2018 | Thompson et al. |
| 2002/0100762 A1 | 8/2002 | Liff et al. |
| 2003/0050731 A1 | 3/2003 | Rosenblum |
| 2003/0216831 A1* | 11/2003 | Hart ........................ G07F 9/001 |
| | | 700/235 |
| 2004/0017475 A1* | 1/2004 | Akers .................... G16H 10/60 |
| | | 348/207.1 |
| 2004/0039911 A1* | 2/2004 | Oka ........................ G06F 21/10 |
| | | 713/175 |
| 2004/0172289 A1 | 9/2004 | Kozic et al. |
| 2004/0204954 A1 | 10/2004 | Lacko |
| 2005/0080651 A1 | 4/2005 | Morrison et al. |
| 2005/0114711 A1* | 5/2005 | Hesselink ............. H04L 63/029 |
| | | 726/4 |
| 2005/0144135 A1* | 6/2005 | Juarez .................... G06Q 40/00 |
| | | 705/51 |
| 2006/0253586 A1* | 11/2006 | Woods ................. G06F 16/9535 |
| | | 709/226 |
| 2006/0293572 A1* | 12/2006 | Bulat ...................... H04N 7/147 |
| | | 600/300 |
| 2008/0097205 A1* | 4/2008 | Takimoto ............... A61B 8/465 |
| | | 600/437 |
| 2008/0177760 A1* | 7/2008 | Fein ...................... G16H 40/67 |
| 2009/0012813 A1* | 1/2009 | Berzansky ............. G16H 10/60 |
| | | 705/2 |
| 2009/0055477 A1* | 2/2009 | Flesher ................. G06F 16/176 |
| | | 709/204 |
| 2009/0106313 A1* | 4/2009 | Boldyga ................ G16H 20/10 |
| 2009/0228300 A1* | 9/2009 | Hamel ............... G06Q 30/0185 |
| | | 705/2 |
| 2009/0287837 A1* | 11/2009 | Felsher .................. G06Q 10/10 |
| | | 709/229 |
| 2010/0094653 A1* | 4/2010 | Tribble .................. G16H 40/67 |
| | | 705/3 |
| 2011/0224509 A1* | 9/2011 | Fish ........................ G06F 21/32 |
| | | 600/301 |
| 2012/0290950 A1* | 11/2012 | Rapaport ............... H04L 67/306 |
| | | 715/753 |
| 2013/0218835 A1* | 8/2013 | Greenspan ............ G06F 16/355 |
| | | 707/610 |
| 2013/0285855 A1* | 10/2013 | Dupray .................. G01S 5/0278 |
| | | 342/451 |
| 2013/0297333 A1* | 11/2013 | Timmons ............... G16H 20/10 |
| | | 705/2 |
| 2013/0304616 A1* | 11/2013 | Raleigh ................. G06Q 40/12 |
| | | 705/34 |
| 2014/0129457 A1* | 5/2014 | Peeler .................. G06Q 10/067 |
| | | 705/317 |

(56) References Cited

U.S. PATENT DOCUMENTS

| | | | | |
|---|---|---|---|---|
| 2014/0223512 A1* | 8/2014 | Hagiwara | ............... | H04L 63/20 |
| | | | | 726/4 |
| 2014/0298030 A1* | 10/2014 | Akiyama | ............... | H04L 63/062 |
| | | | | 713/172 |
| 2015/0095352 A1* | 4/2015 | Lacey | ............... | H04W 4/029 |
| | | | | 707/752 |
| 2015/0286799 A1* | 10/2015 | Padmani | ............... | G16H 20/10 |
| | | | | 705/3 |
| 2016/0092638 A1* | 3/2016 | Padmani | ............... | G16H 40/67 |
| | | | | 705/2 |

FOREIGN PATENT DOCUMENTS

| | | |
|---|---|---|
| CN | 1131076 | 12/2003 |
| EP | 0237588 | 9/1987 |
| EP | 0462466 | 12/1991 |
| EP | 0505627 | 9/1992 |
| EP | 0522527 | 1/1993 |
| EP | 0439355 | 9/1994 |
| EP | 0844581 | 5/1998 |
| EP | 0960627 | 12/1999 |
| EP | 0970655 | 1/2000 |
| EP | 1107158 A1 | 6/2001 |
| EP | 1097671 | 2/2003 |
| GB | 994977 A | 6/1965 |
| GB | 2210713 | 2/1987 |
| GB | 2279784 | 1/1995 |
| GB | 2285135 | 6/1995 |
| GB | 2379037 | 2/2003 |
| JP | 3423055 B2 | 1/1994 |
| JP | 07204253 A | 8/1995 |
| JP | 2000036032 A | 2/2000 |
| JP | 2002011095 | 1/2002 |
| JP | 2002092181 A | 3/2002 |
| JP | 2002520718 | 7/2002 |
| JP | 2003022322 | 1/2003 |
| JP | 2004078970 | 3/2004 |
| JP | 2004326436 | 11/2004 |
| JP | 2004340770 A | 12/2004 |
| JP | 2005252710 A | 9/2005 |
| JP | 2006033291 A | 2/2006 |
| JP | 2006334062 | 12/2006 |
| JP | 2007198934 A | 8/2007 |
| JP | 2008139201 A | 6/2008 |
| JP | 4276654 B2 | 6/2009 |
| JP | 2009265827 A | 11/2009 |
| JP | 2010056619 A | 3/2010 |
| JP | 2010170504 A | 8/2010 |
| JP | 2010533927 A | 10/2010 |
| JP | 2011151430 A | 8/2011 |
| JP | 2012078265 | 4/2012 |
| JP | 5342197 B2 | 11/2013 |
| JP | 5747150 B2 | 7/2015 |
| JP | 6086813 | 3/2017 |
| KR | 20000036642 | 7/2000 |
| KR | 1020000036642 | 7/2000 |
| KR | 20010094703 A | 11/2001 |
| KR | 1020010094703 | 11/2001 |
| KR | 20050054379 | 12/2003 |
| KR | 20110115927 A | 10/2011 |
| KR | 1020110115927 | 10/2011 |
| KR | 20130001500 | 1/2013 |
| WO | WO8400493 | 2/1984 |
| WO | WO9524010 A1 | 9/1995 |
| WO | WO9634291 A1 | 10/1996 |
| WO | WO9741525 | 11/1997 |
| WO | WO9814275 A1 | 4/1998 |
| WO | WO9815092 A1 | 4/1998 |
| WO | WO9824358 A1 | 6/1998 |
| WO | WO9833433 A1 | 8/1998 |
| WO | WO9859487 | 12/1998 |
| WO | WO9904043 | 1/1999 |
| WO | WO9910029 | 3/1999 |
| WO | WO9942933 | 8/1999 |
| WO | WO9944162 | 9/1999 |
| WO | WO9959472 | 11/1999 |
| WO | WO0013588 | 3/2000 |
| WO | WO0029983 | 5/2000 |
| WO | WO0043941 | 7/2000 |
| WO | WO0052437 | 9/2000 |
| WO | WO0052626 | 9/2000 |
| WO | WO0057339 | 9/2000 |
| WO | WO0060449 | 10/2000 |
| WO | WO0069331 | 11/2000 |
| WO | WO0072181 | 11/2000 |
| WO | WO0078374 | 12/2000 |
| WO | WO0101305 | 1/2001 |
| WO | WO0102979 | 1/2001 |
| WO | WO0106468 | 1/2001 |
| WO | WO0145774 | 6/2001 |
| WO | WO0217777 | 7/2002 |
| WO | WO02091276 A1 | 11/2002 |
| WO | WO03025826 A2 | 3/2003 |
| WO | WO03094073 | 11/2003 |
| WO | WO2004070557 | 8/2004 |
| WO | WO2004070994 | 8/2004 |

OTHER PUBLICATIONS

Rusling, David, "An overview of TCP/IP Networking" As downloaded from https://www.tldp.org/LDP/tlk/net/net.html (Year: 1999).*

Pinola, Melanie "The top 50 companies that mine and sell your data (and how to opt out)" Lifehacker Dec. 13, 2013 (Year: 2013).*

Various, "Why there is a separate checksum in TCP and IP headers?" Stack Overflow as retrieved from https://stackoverflow.com/questions/4835996/why-there-is-separate-checksum-in-tcp-and-ip-headers (Year: 2011).*

Microsoft, "How TCP/IP works" as downloaded from https://technet.microsoft.com/en-us/library/cc786128(d=printer,v=ws.10).aspx (Year: 2003).*

Kuznetsov et al., "Take advantage of TCP/IP options to optimize data transmission" as downloaded from https://www.techrepublic.com/article/take-advantage-of-tcp-ip-options-to-optimize-data-transmission/ (Year: 2002).*

Beal, Vangie, "The Differences Between Thick & Thin Client Hardware" downloaded from https://www.webopedia.com/DidYouKnow/Hardware_Software/thin_client.asp (Year: 2006).*

Texas Administrative Code, Title 22, Part 15, Ch 291, Rules 20, 36, and 71-74. Feb. 10, 2004.

Peterson, Charles D. and Anderson, Jr., Howard C.; "The North Dakota Telepharmacy Project: Restoring and Retaining Pharmacy Services in Rural Communities" Feb. 1, 2004.

Cato Reference Manual, Support for Trial Version (Abridged), Vienna, May 2004 Jun. 1, 2004.

Seifert et al.; "The Training of a Telepharmacist: Addressing the Needs of Rural West Texas," American Journal of Pharmaceutical Education 2004; 68 (3) Article 60. Jul. 16, 2004.

Cato Reference Manual, Vienna, May 2005 May 1, 2005.

Phillips, Jon, Associate Director of Telemedicine; "Telepharmacy at Texas Tech," presented Apr. 30, 2003, published at http://www.ttuhsc.edu/telemedicine/publication.htm at least by Jun. 22, 2003 Jun. 22, 2003.

* cited by examiner

CENTRAL USER MANAGEMENT IN A DISTRIBUTED HEALTHCARE INFORMATION MANAGEMENT SYSTEM

CROSS-REFERENCE TO RELATED APPLICATION

This application claims priority from U.S. Provisional Application No. 62/057,881 filed on Sep. 30, 2014, entitled "CENTRAL USER MANAGEMENT IN A DISTRIBUTED HEALTHCARE INFORMATION MANAGEMENT SYSTEM," the contents of which are incorporated by reference herein as if set forth in full.

BACKGROUND

Distributed healthcare information management systems may include a plurality of local instances of healthcare information management applications operating remotely at remote nodes that are in operative communication with a central server. For instance, U.S. Provisional Patent Application No. 61/975,519 entitled "MANAGEMENT OF MEDICATION DOSE ORDERS" filed on Apr. 4, 2014, which is co-owned with the present application and incorporated by reference herein in the entirety, discloses certain embodiments of a distributed healthcare information management system.

In such a distributed system, remote nodes may communicate with a central server. For instance, the remote nodes may communicate with the central server for number of different functions. Administrative functions may also be performed at the remote nodes. In this regard, users of the central server may access the local node to perform certain administrative functions. Additionally, remote users (e.g., users remote from the central server and local node) may access the local node to perform administrative functions. Such administrative functions may be related to the management, upgrade, development, troubleshooting, technical support, or other tasks associated with the local node or a client application (e.g., a healthcare information management application like a pharmacy workflow manager or the like) executed at the local node.

A distributed healthcare information management system (e.g., including a host device such as a central server, client device, or a combination thereof) may also employ a role-based security model. The role-based security model may attribute access rights or privileges to individual users. In turn, individual users may access resources at a distributed healthcare information management system using a username and password combination associated with a given set of permissions or rights.

For instance, in one particular example of a healthcare information management system, the local nodes may each execute a client application comprising healthcare information management system for management of healthcare information (e.g., a pharmacy workflow management application for preparation of dose orders) related to the facility at which the local notice is executing (e.g., a hospital, pharmacy, or the like). As such, local users of the client application may have usernames and password combinations that are used to access the system such that specific permissions may be provided to appropriate users. However, additional access may need to be provided to a remote user (e.g., a central support user at a central server). In this regard, the support user may not have a local username and password combination for access to local client application.

In a traditional approach to providing support users access to a local device a generic "administrator" login may be provided to all central support users for access to a local node for purposes of performing various functions related to the local node. As such, tracking of specific support users taking action with respect to the local node and management of the role-based security model with respect to a specific support user may not be possible. Furthermore, security may be compromised in the case where a user having access to the generic administrator login is no longer to be permitted access to local systems. In turn, continued development to improve the role-based security model of the distributed healthcare information management system is needed.

SUMMARY

In view of the foregoing, the present disclosure includes management of central support user permissions at a plurality of local nodes that are operative to execute client applications in a distributed healthcare information management system. Permission data regarding access, rights, privileges, or other relevant permissions of a support user may be established at a central server. The permission data may define an access level, specific activity permissions, or other authorizations to a support user. In turn, a support user may access the client application executing at a local node of the healthcare information management system to perform functions according to the permission data provided.

Support users may access local nodes executing a client application remotely (e.g., the support users may be co-located with a central server that is remote from a local node). In this regard, the support users may have the need access a plurality of local nodes to perform administrative tasks or functions relative thereto. Accordingly, the central server may distribute permission data regarding support users to any or all of the local nodes executing a client application that is in communication with a central server. The centralized management of support users may allow the permission data regarding the support users to be provided to each client application executing at a local node to allow a support user to access any or all of the client applications executing at any of the local nodes according to the permission data established at the central server. In turn, modifications to the permission data regarding the support users may be provided across an entire system of local nodes in an efficient manner to facilitate rapid modifications of the permission data.

Centralized management of support users in a manner described herein may provide a number of advantages over traditional approaches to facilitating access to support users at a local node. For example and as described above, a generic administrator login may be established at a given local node that provides access rights associated with the tasks normally performed by central support users. Any support user may in turn be required to utilize the generic administrator login to access a local node to make administrative changes at that node. This approach suffers from many disadvantages. For instance, the specific identity of the support user is not known as a plurality of support users may each share access to the generic administrator login at the local node. Also, each local system may each have a general administrator login. Accordingly and especially for systems with many local nodes, remembering each local administrator login may be burdensome. Furthermore because many support users may each know the administrator login for a given local system, upon a change in role of any one of the support users with access to the administrator login, the administrator login may be required to change. This may be burdensome to manage and may result in lapses in security where unauthorized users may have access to a valid administrator login.

However, with the centralized management described herein, the support user may access a local node utilizing unique credential data (e.g., a specific username and password for a given user) such that the permissions associated with the support user may be tailored to the user and/or the support user performing administrative task at a local node may be tracked (e.g., by logging the activity of the specific support user at the local node). In turn, the granularity and specificity at which permissions may be provided may be increased to provide more variety with respect to access rights of the support users accessing local nodes and may provide increased visibility regarding what actions support users are taking at the local node. Furthermore, as the permissions for given support users change, such changes may be easily managed and efficiently provided to local system.

In this regard, a first aspect of the present disclosure includes a centralized support user management system for use in a healthcare information management system. The system may include a host device that is disposed remotely from and that is in operative communication via a network interface with a plurality of local devices each executing a client application comprising a healthcare information management application. The system may also include a support user management module executed at the host device. The support user management module may comprise a memory device having a non-transitory computer-readable data structure that stores permission data regarding at least one support user. The permission data may include a permission identification for the at least one support user regarding permitted activity at the healthcare information management system. The system may also include a network communication device located at the host device in operative communication with the support user management module to transmit the permission data to each of the plurality of local devices via the network interface.

A number of feature refinements and additional features are applicable to the first aspect. These feature refinements and additional features may be used individually or in any combination. As such, each of the following features that will be discussed may be, but are not required to be, used with any other feature or combination of features of the first aspect. In an embodiment, the support user management module may be operative to receive, from respective ones of the plurality of local devices confirmation of receipt of the permission data transmitted by the network communication device. The confirmation of receipt of the permission data transmitted by the network communication device may include a checksum calculated by the respective one of the plurality of local devices in relation to received permission data. The permission data transmitted to a given local device may include a subset of the permission data that is modified since a previous transmission of permission data to the given local device. For example, the support user management module may be operative to determine the subset of the permission data that is modified since the previous transmission of permission data to the given local device at least in part based on the confirmation of receipt of the permission data from the given local device. Furthermore, the support user management module may maintain a timestamp in relation to a time of modification of the permission data, and the support user management module is operative to determine the subset of the permission data that is modified since the previous transmission of the permission data to the given local device at least in part based on the timestamp in relation to the time of modification of the permission data. Additionally or alternatively, the support user management module may maintain a hash value in relation to the permission data, and the support user management module is operative to determine the subset of the permission data that is modified since the previous transmission of the permission data to the given local device at least in part based on the hash value. Further still, the network communication device may be operative to receive, from at least one local device, an error regarding the permission data transmitted to the at least one local device.

In an embodiment, the network communication device may transmit the permission data to the plurality of local devices at regular periodic intervals. The transmission of the permission data may be occur at the request of a local device or may be initiated at the host device. For instance, when initiated at the host device, the host device may periodically provide the permission data to the plurality of local systems. Furthermore, the transmission of the permission data to the local devices from the host device may be triggered by a change to the permission data.

The support user management module may also include a log module that is operative to log activity of the at least one support user in a human readable format for review by a human user of the health care information management system. The log module may log a number of activities and/or data. For instance, the log module may log changes made to the non-transitory computer-readable data structure regarding the permission data. Additionally or alternatively, the log module may be in operative communication with the network communication device and may log data regarding the transmission of the permission data to the plurality of local devices via the network interface. Additionally or alternatively, the log module may log access data regarding access by the at least one support user to the healthcare information management system. In this regard, the access data may include an identity of the at least one support user accessing a resource and an indication of the resource that is accessed by the user. The identity of the user may correspond to a user name of the user.

Furthermore, where the resource accessed by a user is logged, the indication of the resource accessed by the user may include an indicator of whether the resource includes protected health information (PHI). As discussed more herein, PHI may include any or all information that provides identifying characteristics of a patient. The indicator of whether the resource includes PHI may be based on a resource flag indicative of whether the resource includes PHI. The resource accessed by a user may include a report. For instance, the report may include data regarding one or more patients. As such, the resource flag indicative of whether the resource includes PHI may be dynamically generated based on whether the report includes a data class that is defined as containing PHI. Further still, for some resources (e.g., all resources at a given location such as a local device), resources may be assumed to contain PHI. As such, the resource flag may indicate some resources have PHI based on the location at which the resource is provided.

In an embodiment, the support user management module may also include a permission editing module that is operative to modify the permission data stored in the non-transitory computer-readable data structure. The permission editing module may be utilized to modify the permission data for one or more support users and/or modify support user groups. The ability to access the permission editing module may be a defined permission identification such that only certain support users may have access to the permission editing module.

In an embodiment, the permission data may be correlated to a user name regarding the at least one support user and the user name may be associated with a password. Accordingly, access to a resource at the local device or the host device may require provision of a correct user name and password combination. The access to the resource at the local device or the host device may in turn be defined by the permission identification associated with the user name. As such, access to a resource may only be provided to a user upon receipt of a correct user name and password combination associated with a support user that has a sufficient permission identification to access the resource requested. The user name may be associated with a single individual user. As such, the disadvantages associated with administrator login information sharing described above may be reduced.

In an embodiment, the non-transitory computer-readable data structure may store at least one support user group. The support user group may have permission data associated with the group. The permission data for a group may be applicable to each member of the support user group. As such, the at least one support user may be a member of the support user group such that the user name of the at least one support user is associated with the support user group. The support user group may be provided task specific permission identifications.

One possible permission identification may define a data class that is accessible by the at least one support user. For instance, the data class may be defined as either one of data having PHI or not having PHI. As such, a permission identification may be selected that identifies that the at least one support user is authorized to access the data class not having PHI only. That is, the support user may be restricted from accessing data containing PHI. Alternatively, a permission identification may identify that the at least one support user is authorized to access the data class having PHI. As such, the at least one support user may access data containing PHI if provided with this permission identification.

In an embodiment, the permission data may include at least a first permission identification relative to access of a resource at the host device and at least a second permission identification relative to access of a resource at the local device. That is, permission data may include permission identifications for both a host device and a local device in the healthcare information management system. As such, permission identifications may be specific to a particular node in the system accessed by a support user.

In one application, the host device may be a central server of a healthcare information management system, and the plurality of local devices may each include a pharmacy workflow management application for use in preparation of doses for administration to a patient. As such, permission identifications for the pharmacy workflow management application may include permission identifications related to specific tasks associated with preparation of a dose and/or specific tasks in relation to management of dose order records at the pharmacy workflow management application.

In the application of the central support user management to a healthcare information management system that includes pharmacy workflow management applications, the central server and the plurality of pharmacy workflow management applications may be unaffiliated. For instance, the central server may be maintained or executed by a provider of the healthcare information management application executed at the local device. As such, the central server may have a number of support users that may access a local device to provide technical support services in relation to the application. Accordingly, the at least one support user may be remote from the plurality of local devices.

A second aspect of the present disclosure includes a client node of a support user management system for use in healthcare information management. The client node may include a local device that is in operative communication with a host device that is disposed remotely from the local device. The local device may execute a client application comprising a healthcare information management application (e.g., such as pharmacy workflow management application). The local node may also include a network communication device located at the local device that is in operative communication with the host device to receive permission data from the host device. The permission data may include permission identification for at least one support user regarding permitted activity at the healthcare information management system. The local node may also include a memory device located at the local device that includes a non-transitory computer-readable data structure that stores the permission data. The local node may also include a permission module executed at the local device that is in operative communication with the memory device. The permission module may be operative to receive a request for access by the at least one support user and to permit access to the client application by the at least one support user based on the permission data.

A number of feature refinements and additional features are applicable to the second aspect. These feature refinements and additional features may be used individually or in any combination. As such, each of the following features that will be discussed may be, but are not required to be, used with any other feature or combination of features of the second aspect.

For instance, the local node of the second aspect may host a local device referenced in the system of the first aspect. In this regard, the local node of the second aspect may comprise a local device as referenced in the system of the first aspect. Accordingly, the first and second aspects may be used in conjunction in a support user management system.

In an embodiment, the permission module may be operative to provide confirmation of receipt of the permission data to the host device. The confirmation of receipt of the permission data may include a checksum calculated by the permission module in relation to received permission data. The permission data received from the host device may include a subset of permission data that is modified since the previous transmission of permission data to the local node.

The network communication device may transmit to the host device one of a confirmation of receipt of the permission data or an error regarding the permission data received at the local device. In this regard, the host device may be provided with an update as to the status of the last permission data successfully received at the local node. The network communication device may receive the permission data from the host device at regular periodic intervals.

The client node may also include a log module that may be operative to log activity of the at least one support user at the client device in a human readable format for review by a human user at the client device by the at least one support user. The log module may log changes made to the non-transitory computer-readable data structure regarding the permission data. The log module may be in operative communication with the network communication device and may log data regarding the receipt of the permission data from the host device.

In an embodiment, the log module may log access data regarding access by the at least one support user to the client device. The access data may include an identity of the user accessing the host device and an indication of a resource that is accessed by the user. The identity of the user may include a user name of the user. The indication of the resource accessed by the user may include an indicator of whether the resource included protected health information (PHI). The indicator of whether the resource included PHI may be based on a resource flag indicative of whether the resource includes PHI. The resource that is subject to the logging may include a report. In this regard, the resource flag indicative of whether the resource includes PHI may be dynamically generated based on whether the report included a data class defined as containing PHI.

In an embodiment, the permission data may be correlated to a user name regarding the at least one support user and the user name may be associated with a password. Accordingly, access to a resource at the local device may require provision of a correct user name and password combination. In turn, the access to the resource at the local device or the host device may be defined by the permission identification associated with the user name. The user name may correspond to a single individual user.

In an embodiment, the non-transitory computer-readable data structure may store at least one support user group. The support user group may have permission data applicable to each member of the support user group defined for the group. The at least one support user may be a member of the at least one support user group such that the user name of the at least one support user may be associated with the at least one support user group. The at least one support user group may be provided with task specific permission identification.

The permission identification of the permission data may define a data class accessible by the at least one support user. The data class may be defined as either one of data having protected health information (PHI) or not having PHI. The permission identification may identifies that the at least one support user is authorized to access the data class not having PHI only. Alternatively, the permission identification identifies that the at least one support user is authorized to access the data class having PHI. The permission module at the client device may determine whether access to the resource is granted to the at least one support user based at least on receipt of a correct password corresponding to the user name and the permission identification in the permission data regarding the at least one support user.

As described above, in one application the host device comprises a central server of a healthcare information management system, and the local device comprises a pharmacy workflow management application for use in preparation of doses for administration to a patient. As such, the central server and the pharmacy workflow management applications may be unaffiliated. Accordingly, the at least one support user is remote from the local device.

A third aspect includes a centralized support user management system for use in healthcare information management. The system may include a host device comprising a host memory device that includes a non-transitory computer-readable data structure that stores permission data regarding at least one support user. The permission data may include permission identification for the at least one support user regarding permitted activity at a client application. The system may also include a plurality of client devices each executing the client application comprising a healthcare information management application. Each of the plurality of the client devices may be in operative communication with the host device via a network interface to receive the permission data for storage in a local memory device at each corresponding one of the plurality of client devices.

A number of feature refinements and additional features are applicable to the third aspect. These feature refinements and additional features may be used individually or in any combination. As such, each of the following features that will be discussed may be, but are not required to be, used with any other feature or combination of features of the third aspect. Furthermore, any of the foregoing feature refinements and additional features discussed above in relation to the first and second aspects may be utilized in the third aspect without limitation.

A fourth aspect includes a method of support user management for use in a healthcare information management system. The method may include storing permission data regarding at least one support user in a non-transitory computer-readable data structure at a host device. The permission data may include a permission identification for at least one support user. The method may also include transmitting the permission data to a plurality of local devices each executing a client application comprising a healthcare information management application. The permission identification may define access privileges for the at least one support user to access the healthcare information management system including the healthcare information management application.

A number of feature refinements and additional features are applicable to the fourth aspect. These feature refinements and additional features may be used individually or in any combination. As such, each of the following features that will be discussed may be, but are not required to be, used with any other feature or combination of features of the fourth aspect.

For example, the method may include modifying the permission data at the host device with a permission editing module at the host device. The method may also include maintaining a record of the modification of the permission data at the host device. The transmitting may include only transmitting permission data that is modified since a previous transmission to each given one of the plurality of local devices. For instance, the maintaining may include time-stamping the permission data with a timestamp of the modifying, and the permission data that is modified since the previous transmission to each given one of the plurality of local devices may be determined at least in part based on the timestamp. Additionally or alternatively, the maintaining may include generating a hash value for the permission data, and the permission data that is modified since the previous transmission to each given one of the plurality of local devices may be determined at least in part based on the hash value.

The method may include receiving, from at least one local device, one of a confirmation regarding the permission data received at the at least one local device or an error regarding the permission data transmitted to the at least one local device. For example, the confirmation may include a checksum. As such, the host device may maintain a status of the last successful transmission of permission data to a local device. The transmitting may occur at regular periodic intervals. Additionally or alternatively, the transmitting may be triggered upon a request for permission data by a local device or upon modification of permission data at the host device.

The method may also include logging activity in relation to the healthcare information management system in a human readable format for review by a human user. The logging may include recording changes made to the non-transitory computer-readable data structure regarding the permission data. The logging may also include recording data regarding the transmission of the permission data to the plurality of local devices. Further still, the logging may include recording access data regarding user access to the healthcare information management system. In this regard, the access data may include an identity of the user accessing the host device and an indication of a resource that is accessed by the user. The identity of the user comprises a user name of the user. The indication of the resource accessed by the user may include an indicator of whether the resource included protected health information (PHI). The indicator of whether the resource included PHI may be based on a resource flag indicative of whether the resource includes PHI. As such, in an embodiment the resource may include a report, and the method may include dynamically generating the resource flag indicative of whether the resource includes PHI based on whether the report included a data class defined as containing PHI.

The method may include correlating permission data to a user name regarding the at least one support user. Additionally, the user name may be associated with a password to provide user credentials for a given support user. In turn, the method may also include receiving a user name and password from a user, determining the user name and password is a valid combination, and providing access to a resource of the healthcare information management system based on the permission identification associated with the received user name. The use name may correspond to a single individual user.

Also, in an embodiment the user name may be associated with a support user group. The support user group may have permission data applicable to each member of the support user group. As such, the method may include assigning task specific permissions to the support user group. In turn, each member of the support user group is assigned the task specific permissions. The method may further include restricting a permission identification for the a least one support user to access to a data class. The data class may be defined as data not having protected health information (PHI). As such, the method may include identifying, based on the permission identification, whether the at least one support user is authorized to access the data class not having PHI only. Additionally or alternatively, the method may include identifying, based on the permission identification, whether the at least one support user is authorized to access a data class having PHI.

As may be appreciated, permission identifications may be related that relate to access of a resource at the host device (e.g., a central server) or at a client device. In this regard, the method may include defining at least a first permission identification relative to access of a resource at the host device and at least a second permission identification relative to access of a resource at the client device.

A fifth aspect may include a method for management of centralized support user access at client node in a healthcare information management system. The method may include executing at least one client application comprising a healthcare information management application at a client device at the client node. The method may also include receiving, from a host device in the healthcare information management system, permission data that includes permission identification for at least one support user to access the client application. The method may also include operating a permission module at the local device. The operating may include receiving a request for a access to a resource at the client device. The request may include a user name associated with the at least one support user. The operating may also include determining whether to provide the requested access to the resource based on the user name and the permission data.

A number of feature refinements and additional features are applicable to the fifth aspect. These feature refinements and additional features may be used individually or in any combination. As such, each of the following features that will be discussed, or any of the foregoing features discussed in relation to the first, second, third, or fourth aspect, may be, but are not required to be, used with any other feature or combination of features of the fifth aspect.

BRIEF DESCRIPTION OF THE DRAWINGS

FIG. 5 is a view of an embodiment of a user interface of a pharmacy workflow management application with which dose order records stored by the pharmacy workflow management application may be managed.

FIGS. 6-12 are views of an embodiment of a user interface of a pharmacy workflow management application that provides management of dose order records stored by the pharmacy workflow management application.

FIGS. 16-17 depict an embodiment of a user interface of the pharmacy workflow management application that may be presented to a pharmacist when reviewing a dose.

DETAILED DESCRIPTION

Figure 1:
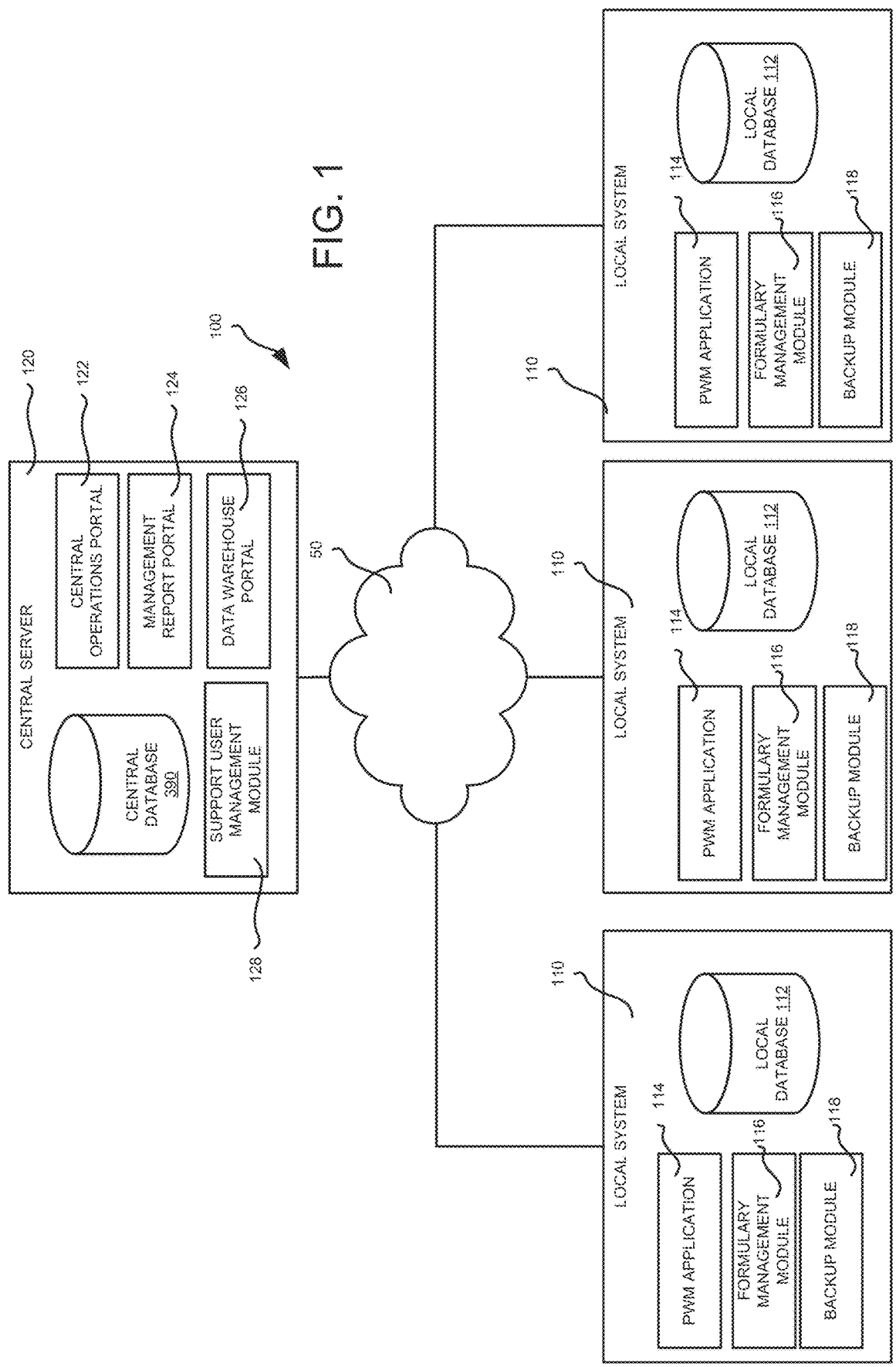
FIG. 1 is a schematic view of an embodiment of a healthcare information management system in which centralized support user management may be implemented.

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

The present disclosure contemplates centralized user support management in a distributed healthcare information management system. For example, a pharmacy workflow management application may be provided as a client application that executes at a local node in the healthcare information management system. The pharmacy workflow management application may facilitate pharmacy workflow management at local node. The local node may correspond to a facility such as a hospital, pharmacy, or other facility capable of preparing a dose for administration to a patient. Pharmacy workflow management provided by the pharmacy workflow management application may include one or more activities within a pharmacy that may include processing received medication dose orders at a pharmacy, creating corresponding dose order records for each received dose order, managing (e.g., viewing, sorting, prioritizing, etc.) dose order records, guiding a pharmacy technician in preparing the dose order medication, gathering information regarding the preparation of a dose to fulfill a dose order, reviewing the medication dose order, and/or tracking of medication dose order records in the pharmacy.

The local node may comprise one or more devices that may include hardware and/or software that may execute one or more applications related to the pharmacy workflow management application. The pharmacy workflow management application may include one or more processors operative to access machine-readable data stored in a storage medium (i.e., a memory) that provide instructions to the one or more processors for execution to provide the functionality described herein.

Additionally, the pharmacy workflow management application may comprise a portion of a distributed healthcare information management system. The distributed healthcare information management system may include a central server that may be in communication with a plurality of local nodes. The local nodes may each execute and instance of the pharmacy workflow management application to manage pharmacy activity at a corresponding one of the facilities associated with a local node. The central server may provide support services to the local node to support the pharmacy workflow management application and/or may provide additional services such as data backup, report generation, or access to data sets stored at the central server.

The following description provides details regarding embodiments of a distributed healthcare information management system and embodiments of a pharmacy workflow management application. As may be appreciated, the pharmacy workflow management application may have administrators or support users that periodically assess, maintain, upgrade, or otherwise access resources of the pharmacy workflow management application. Furthermore, upon initial setup of the pharmacy workflow management application at a local node, administrators or support users may access the application to perform functions related thereto connection with the initiation thereof. In this regard, support users may have the need to access the pharmacy workflow management application from time to time at the local node of the healthcare information management system for a variety of reasons. Accordingly, application of role-based security that extends to remotely located support users (e.g., central support users) may be advantageous to facilitate more robust role-based security model for a pharmacy workflow management application.

In addition to the centralized support user management described herein, embodiments of a pharmacy workflow management application that may be part of a healthcare information management system is described herein. In turn, the central support user management techniques described herein may be utilized in connection with the healthcare information management system including the pharmacy workflow management application described herein.

The present description generally includes a discussion of the operation of the centralized support user management applicable to a healthcare information management system. Thereafter, a description of an embodiment of dose order processing that may be performed by the pharmacy workflow management application is described. This dose order processing may include receiving dose orders and generating dose order records that are in turn stored by the application. Also described herein are embodiments that provide functionality related to the management of the dose order records within the pharmacy. The management functionality of the pharmacy workflow management application may include, but is not limited to, viewing, sorting, modifying, prioritizing, organizing, or otherwise managing dose order records. The pharmacy workflow management application 114 may also distribute, provide, or assign dose order records to workstations for preparation of a dose (i.e., a physical dose form capable of being administered to a patient) that corresponds to a dose order record. The pharmacy workflow management application may provide a protocol to assist a user in preparing a dose according to a dose order record. During the preparation, dose order metadata regarding the dose prepared in connection with the dose order record may be recorded or acquired. In connection with the preparation of the dose, embodiments of functionality related to remote pharmacy verification are also described. Furthermore, features related to the ability to utilize the application to track dose orders in the pharmacy (e.g., with respect to physical location and/or processing status in or other relevant status indications) are described.

With initial reference to FIG. 1, a distributed healthcare information management system 100 is depicted. The distributed healthcare information management system 100 may include one or more local systems 110. The local systems 110 may each comprise a local node in the system 100. The local systems 110 may each execute a pharmacy workflow management application 114. For instance, each local system 110 may include at least one local device executing a client application for providing functions related to the pharmacy workflow management application. As shown in FIG. 1, a plurality of local systems 110 may be provided that are each in operative communication with a central server 120. For example, the local systems 110 may be in operative communication the central server 120 by way of a wide area network 50 (e.g., the Internet). In this regard, the central server 120 and each local system 110 may collectively define the healthcare information management system 100.

Each local system 110 may be a healthcare facility such as a hospital, pharmacy, outpatient clinic, or the like, that prepares doses for administration to a patient. The respective pharmacy workflow management application 114 at each local system 110 may be operative to generate and/or capture medical information that may be provided to the central server 120 by way of the wide area network 50. As will come to be appreciated from the discussion below in relation to the pharmacy workflow management application, the medical information may include medication dose order data that may include metadata regarding the dose order record and/or dose. The pharmacy workflow management application 114 each local system 110 may allow for the pharmacy workflow management functions described in greater detail below. In any regard, any or all data generated by the pharmacy workflow management application may be provided to the central server 120. In this regard, central server 120 may provide for data collection and/or data backup services in relation to the local systems 110 as well as other functions described in greater detail below.

Accordingly, in at least one embodiment the local systems 110 may comprise unaffiliated and discrete healthcare facilities capable of preparing medication doses for administration to patients. The central server 120 may be hosted by another discrete and unaffiliated third-party that may be separate from any of entities of the local systems 110. For instance, the central server 120 may be hosted and/or executed by an application provider that provides one or more client applications for execution by the local systems 110 to facilitate the pharmacy workflow management application 114. Specifically, the central server 120 may be executed or hosted by an application provider that provides the pharmacy workflow management application each local system 110. In this regard, it may be appreciated that support users at the central server 120 may be particularly capable of providing technical support services, troubleshooting, or other assistance to local system 110 in relation to the pharmacy workflow management application.

The central server 120 and/or the local systems 110 may provide one or more resources in connection with the healthcare information management system 100. For instance, the resources provided by the local systems 110 may relate to any or all resources associated with the pharmacy workflow management application executed at the local system 110. This may include, for example, functions related to those processing, preparation, approval, or tracking. Furthermore, the resources provided by the local systems 110 may provide reporting, logging, or auditing functions in relation to the pharmacy workflow management application.

Furthermore, the central server 120 may provide, among other resources, a central operations portal 122, a management report portal 124, or a data warehouse portal 126. Generally, the central operations portal 122 may provide, among other resources, data backup services to the pharmacy workflow management application 114 of each local system 110. The management report portal 124 may allow a user accessing this resource to generate management reports that may relate to collectives of local systems 110 or individual local systems 110. For example, one or more local systems 110 may belong to an organization such that the data corresponding to the collective local systems 110 comprising the organization may be aggregated (e.g., at the central server 120). In this regard, organizational users may be defined that are members of local systems 110 belonging to an organization such that the organizational users may be able to access data related to any of the local systems 110 belonging to the organization. The management reports may include data in relation to the medical information received from one or more local systems 110.

Furthermore, a data warehouse portal 126 may be provided that may provide an aggregated source of medical information from local systems 110 and/or other data sources. The data warehouse portal 126 may provide functionality related to data aggregation and/or data formatting that allows multiple sources of medical information to be aggregated for purposes of data analytics the like. In this regard, the data warehouse portal 126 may provide functionality resources as described in U.S. Provisional Patent Application No. 62/019,227 entitled "MANAGED MEDICAL INFORMATION EXCHANGE" filed on Jun. 30, 2014, which is co-owned with the present application and is incorporated by reference herein in its entirety.

Access to the one more resources at the central server 120 and/or local system 110 may be governed by a role-based security model that requires appropriate user credentials (e.g., a valid username and password combination) be provided to access a given resource of the healthcare information management system 100. Users of the healthcare information management system 100 may be located at the central server 120, a local system 110, or remote location that is remote from both the central server 120 and the local system 110. As appreciated from the discussion above, situations may arise where users at the central server 120 may have the need to access resources at the local system 110 as well as where users at the local system 110 may have the need to access to certain resources at the central server 120. For instance, local users at the local system 110 may wish to access functionality or resources provided with one or more the central operations portal 122, the management report portal 124, or the data warehouse portal 126. Additionally, central support users at the central server 120 may beneficially access local systems 110. Central support user access to the local system 110 may be to access local resources for the purpose of initialization, troubleshooting, or technical support services provided by users at the central server 120.

The ability to provide remote users access to local systems 110 may be particularly difficult because each local system 110 may be unaffiliated with other local systems 110 and/or the central server 120. That is, each local system 110 may be executed by a facility that maintains a database of local users and may not otherwise have access to user credentials for users outside of the local system 110. In this regard, information that governs the role-based security provided at the local system 110 may not ordinarily include information related to centralized support users from the central server 120 because the local system 110 may not have access to user credentials (e.g., username and password combinations) from the central server 120. In turn, the present disclosure provides a mechanism by which permission data maintained at the central server 120 may be distributed to local systems 110 for purposes of providing access to centralized support users to resources at the local systems 110.

Specifically, the central server 120 may maintain permission data regarding one or more support users. The permission data may be stored in a non-transitory computer-readable data structure at the central server 120. The permission data may define one or more permission identifications for at least one support user regarding permitted access to the health information management system by the support user. That is, the permission identification may identify resources, data classes, or specific data that may be or may not be accessible by a given user. The permission identification may also identify specific tasks a user is allowed to perform and/or that a user may not perform. The permission identifications may be specific to resources at the central server 120, specific to resources at a local system 110, or generally applicable to resources at either the central server 120 or the local system 110.

In an embodiment, the permission data may include information related to support user groups. The support user groups may have permissions assigned to the support user group such that each member of the support user group is assigned a set of permissions provided to the group. In turn, centralized support users may be associated with the support user group and in turn inherit the permissions provided to the support user group. Details regarding support users and support user groups are provided in greater detail below.

Support users may be associated with usernames that may provide identification of the support user. In this regard, specific individual users may each be provided with a username. Additionally, a password associated with username may be established to provide authenticated identification of a support user upon receipt of a valid username and password combination. Providing specific individual users with a corresponding username password may help to prevent a common scenario where a single administrator username and password are shared among the plurality of users. As described briefly above, such a situation is disadvantageous because multiple users may each access a resource utilizing the same generic administrator name and password. In turn, tracking of actions by any given user may not be possible as multiple users may each utilize the administrator username password to access the system. That is, to the extent actions may be logged, the actions may be associated with the general administrator username such that the specific individual taking the action may not be tracked.

Furthermore, control of the username and password for the administrator account may be difficult because a plurality of individuals may each have access to the generic administrator username and password. Accordingly, if any one of the individuals with access to the generic administrator login and password changes roles or is terminated, or if new individuals are to be provided with the instrument login and password, the ability to control access to those who know the generic administrator username password may be difficult to maintain. This may require resetting or changing the generic administrator username and password upon any event occurring in relation to an individual that had access to the generic administrator username and password. This may be burdensome to implement, and thus may result in a lack of security in relation to those who have access to resources.

The present disclosure may assist in circumventing such difficulties in that each specific individual user may provided with corresponding permission identifications relative to the user (e.g. or to a user group with which the user is assigned). In this regard, any change in roles for a specific user may be easily facilitated by the system presented herein. For example, should a user's permissions within an organization change, the specific permission data for that particular user may be modified. For instance, the user may be removed from a support group, moved to a different group, or removed altogether. That is, the modification of permission data for anyone user or group of users may be easily facilitated utilizing the support user management module 128 at the central server 120. As will be described in more detail below, the support user management module 128 may provide a user interface allows for the management of support user groups and support users as well as the permission data related to either. In turn, the permissions associated with a user may be modified and provided to local systems 110 such that the modified permissions associated with a user may be distributed to each local system 110 to prevent unauthorized continued access by a support user upon a change in role or separation from an organization. In turn, the centralized management of support users may provide more robust role-based security and facilitate central support user access to local systems 110 without having to resort to the use of a generic administrator login.

A permission identification of the permission data may relate to permissions for resources provided either the central server 120 or the local system 110. For example, at the central server 120, examples of possible permissions include the ability to view reports having data from all local systems 110 in communication with the central server 120, the ability to view local system 110 specific data in reports, the ability to view reports with data related to organizations (e.g., predefined collectives of local systems 110), the ability to view protected health information (PHI), the ability to manage support users and support user groups, the ability to view local server details, the ability to manage report definitions, the ability to access the central server management portal 124, the ability to manage organizations, the ability to view billing information, the ability to view a data warehouse portal 126, or other functions associated with a central server 120. In this regard, permission identifications may be provided to support users at the central server 120 that may dictate access provided to the support user for access to resources at the central server 120.

Additionally, a number permission identifications be provided in relation to each local system 110. Permissions that may be applicable to a local system 110 may include the ability to operate a label processor, the ability to manage/configure the label processor, the ability to prepare standard doses, the ability to prepare high-risk doses, the ability to prepare hazmat doses, the ability to run reports at the local system 110, the ability to reassign a dose to a different workstation from the one currently assigned, the ability to distribute doses from the pharmacy, the ability to discontinue doses at a workstation, the ability to prepare products at a workstation, the ability to perform service tasks at the workstation, the ability to print a dose at a workstation, the ability to configure workstation settings, the ability to prepare total parenteral nutrition (TPN) doses at a workstation, the ability to adjust dose expiration times, the ability to reuse doses previously prepared, the ability to verify doses, the ability to manage a formulary, the ability to manage security at the local system 110, the ability to manage a local system configuration, the ability to manage or query the dose database, the ability to query dose preparation data, the ability to query product preparation data, the ability to view a situation dashboard, the ability to view management reports regarding a local system 110, the ability to requeue lost or damaged doses, the ability to place or remove doses to/from hold status, the ability to assign a new administration date/time to a dose, the ability to place new orders for stock doses, the ability to reprint dose product labels from a workstation, the ability to track doses (or products) using scan events, the ability to manage label designs and profiles, the ability to select and assemble doses and kits, the ability to manage a dose logic engine rules, the ability to manage objects which define a dose preparation protocol, the ability to manage changes to action groups, the ability to allow access to special formulary editing tools, the ability to manage a list of reasons, the ability to allow entering of custom reasons, the ability to allow users to modify certain properties of a dose order, and/or the ability to manage analytics provided by way of the data warehouse portal 126 at the local system 110.

Figure 22:
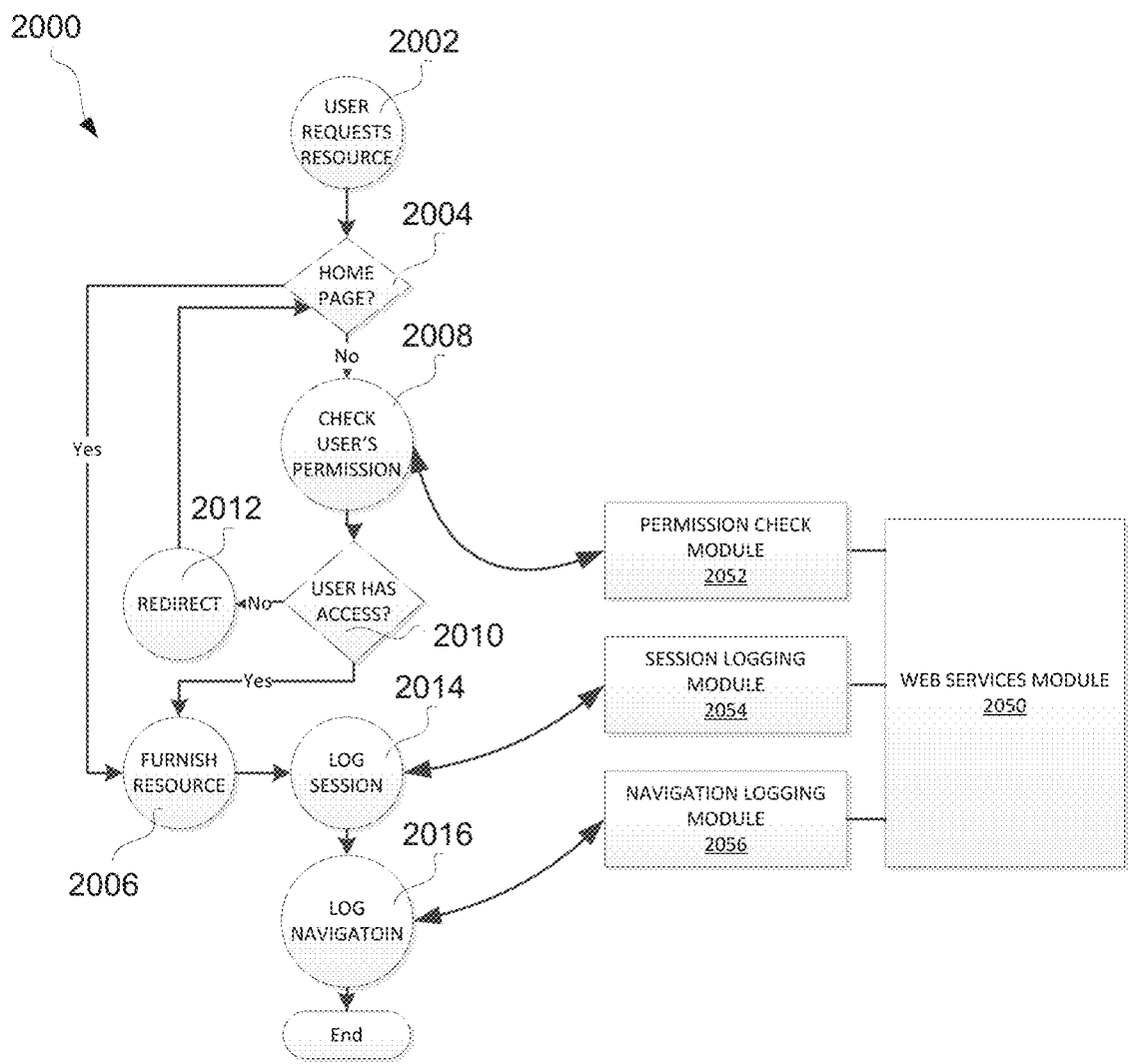
FIG. 22 depicts a flow chart of an embodiment of a method for centralized support user management that makes reference to an embodiment of modules utilized to execute the functionality of the flowchart.

With further reference to FIG. 22, a flowchart depicting an embodiment of a method 2000 for providing access to a user to a resource is depicted. The flow chart includes schematic representations of one or more modules accessed in the process 2000 to perform functionality related thereto. As may be appreciated, the modules referenced in FIG. 22 may be provided at either the central server 120 the local system 110 to facilitate secured access to a resource at a corresponding one of the locations. The process 2000 may initiate upon a user navigating 2002 to a resource (e.g., potentially provided as a webpage) that may be hosted by the local system 110 or the central server 120. The page to which the user navigates 2002 may be associated with a resource provided by the local system 110 or the central server 120. For example, the resource may comprise a webpage that provides functionality related to the local system 110 (e.g., a pharmacy workflow management application 114 thereof) or the central server 120 as described above. It may be determined 2004 whether the page navigated to is the homepage for the resource or not. If the page requested is the homepage, the page may be displayed 2006 to the user. The homepage may provide a field to receive a username and password combination for a user attempting to access the resource. If it is determined 2004 that the page sought to be accessed by the user is not the homepage, the method 2000 may include checking 2008 the user permission to access the page. In this regard, the user may provide a username and password combination. Based upon this username password combination, it may be determined (e.g., by a permission check module 2052 provided as a web service module 2050 at the device being accessed) whether the user has a corresponding permission identification in permission data accessed by the permission check module 2052. In this regard, the permission check module 2052 may determine 2010 whether the user has access to the requested resource by determining if an appropriate permission identification for the particular user is stored in permission data accessible by the permission check module 2052. In this regard, the permission check module 2052 may access permission data stored in a non-transitory computer readable data structure at the device being accessed. If the user does not have access (e.g., the user is not have an appropriate permission identification to access the resource being requested), the user may be redirected 2012 to a redirect page that may, for example, prompt a user for a correct username password with sufficient access rights to access the page requested or provide a indication that the user does not have sufficient access rights access the resource requested. In the event that it is determined 2010 that the user has sufficient access rights, the resource may be furnished 2006 to the user (e.g., the page requested by the user may be displayed to the user).

The process 2000 may also include logging 2014 a user session. Further information regarding the logging 2004 of the user session is described below. Additionally, logging 2016 of the navigation of the user may be provided as is further described below. In this regard, a session logging module 2014 and a navigation logging module 2056 may be provided in the web service module 2050.

It may be appreciated that when determining 2010 whether a user has access to a given resource (e.g., whether the user may access a particular page requested), the determination may at least part be based whether permission data stored at the device providing the resource includes a permission identification for the user for the resource requested. As described above, it may be advantageous to provide a distributed central support user model whereby permission data regarding central support users is distributed to local systems 110 such that local systems 110 may properly determine whether a central support user attempting to access a resource provided local system 110 has sufficient access rights.

Figure 23:
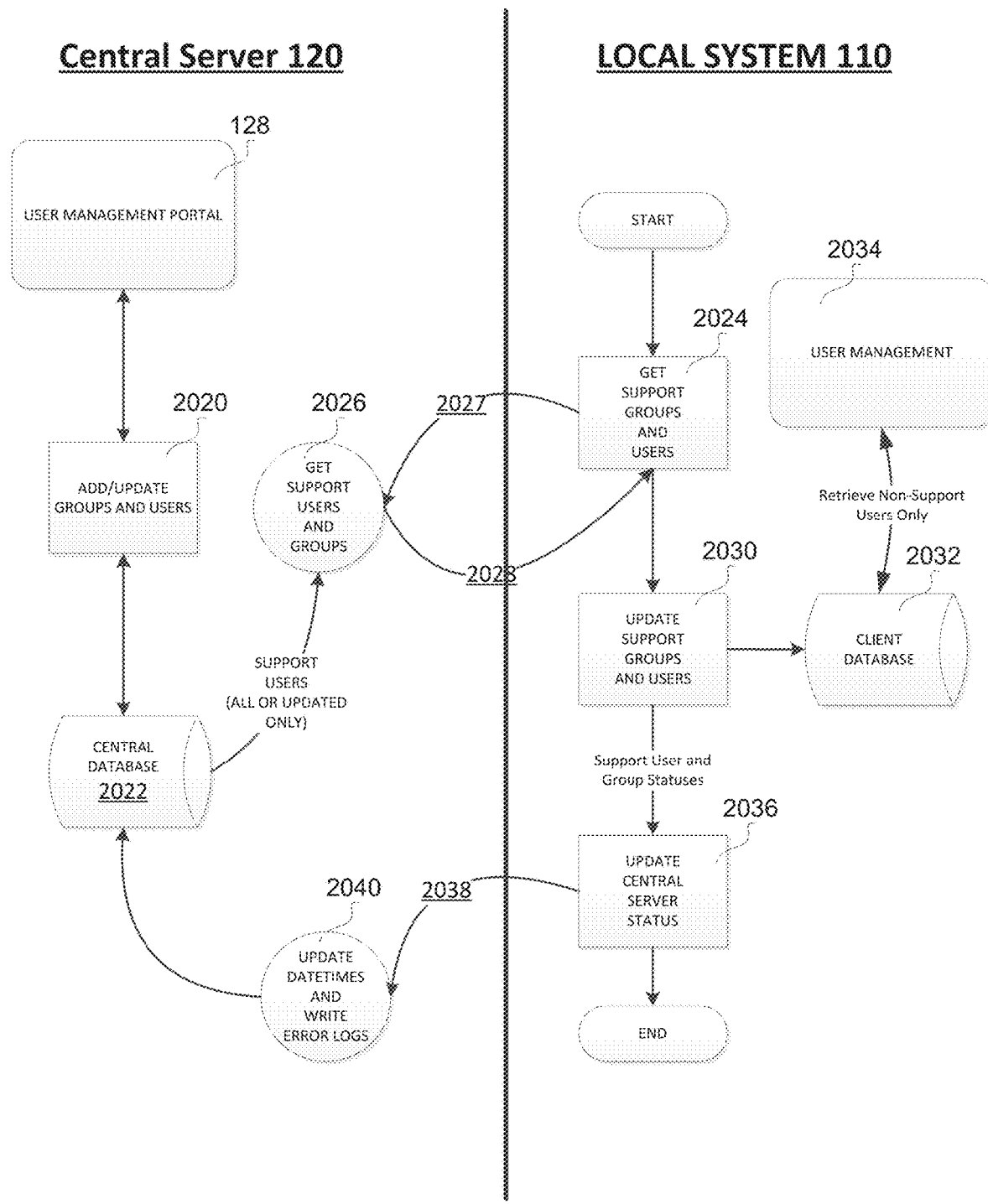
FIG. 23 depicts a schematic view of an embodiment of a process at a central server and a local system to implement centralized support user management.

In this regard, FIG. 23 depicts an embodiment of a system for use in distributing permission data from a central server 120 to a local system 110. Initially, the central server 120 may provide a support user management module 128 as referenced above in FIG. 1. The support user management module 128 may be accessed 2020 and utilized to add, modify, or delete groups and/or users.

Figure 21:
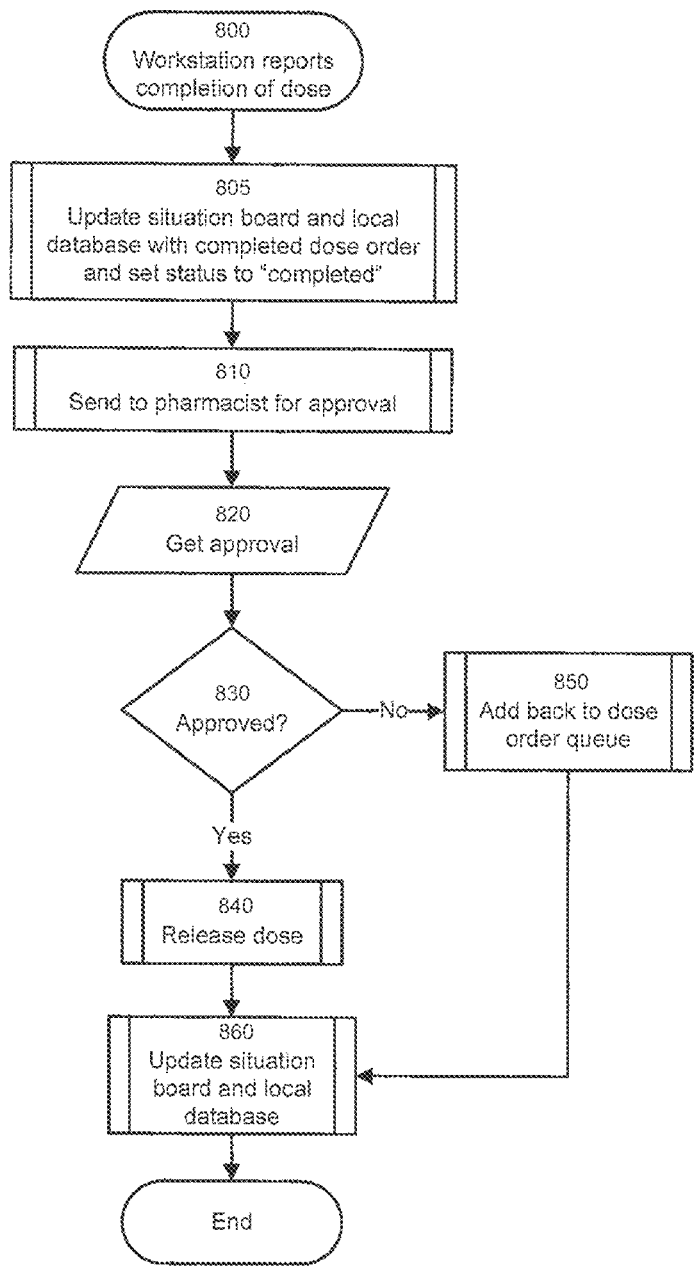
FIG. 21 depicts a flow chart of an embodiment of a method for review doses by a pharmacist.
Figure 24:
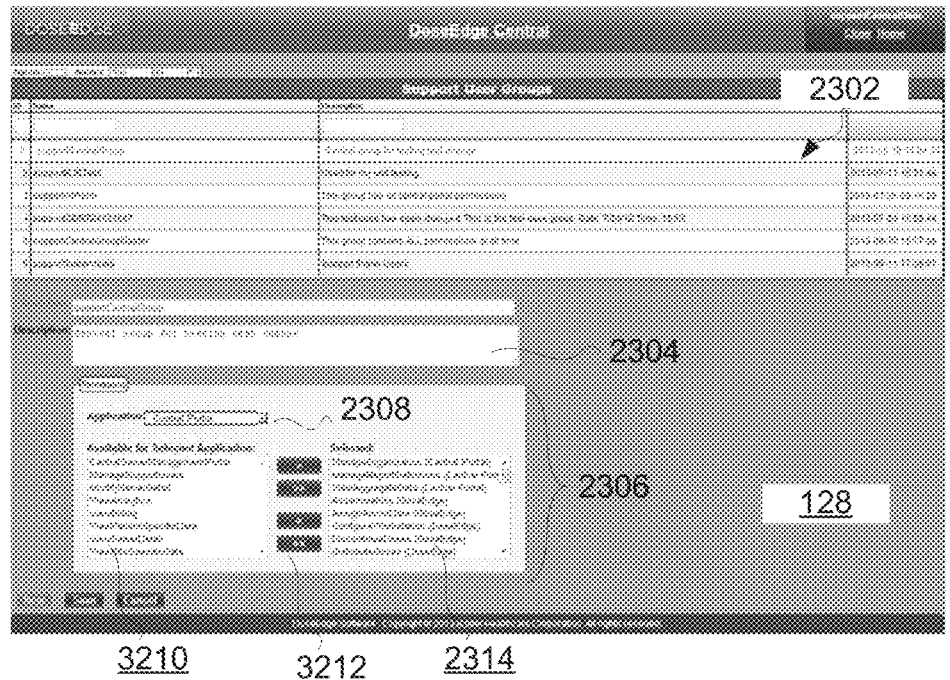
FIG. 24 depicts an embodiment of a user interface for management of support user groups according to an embodiment of centralized support user management.
Figure 25:
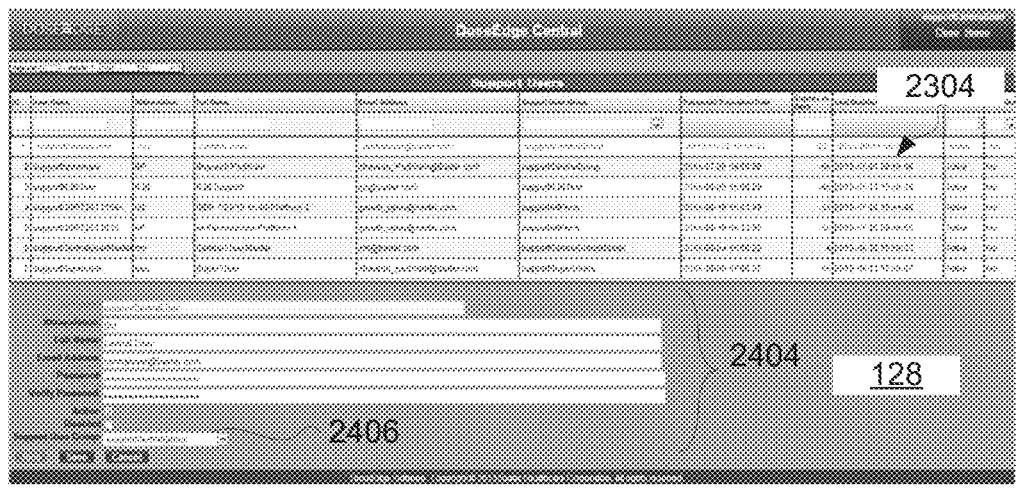
FIG. 25 depicts an embodiment of a user interface for management of support users according to an embodiment of centralized support user management.

With further reference to FIGS. 24 and 25, exemplary user interfaces are depicted that provide for the addition, modification, or deletion of groups and/or users at 2020 in FIG. 21. For example, in FIG. 24 a user interface of the support user management module 128 is depicted. In FIG. 24, the support user management module 128 provides a listing 2302 of support user groups. A plurality of support user groups is shown in the group listing 2302. As may be appreciated, the support user management module 128 may allow user groups to be added to or deleted from the listing 2302. Furthermore, a group may be modified by selection of the groups the listing 2302. As shown in FIG. 24, the group "supportCentralGroup" has been selected for modification as an example. The support user management module 128 provides a description 2304 of the group that allows the group to be described for reference.

Furthermore, the module 128 may provide a permission editing interface 2306. In general, the permission editing interface 2306 may allow for permission identifications to be associated with a given support user group. In this regard and as described above, the permission identifications provided to a support user group may be directed to resources accessed at a local system 110 or directed to resources accessed at the central server 120. Accordingly, a location selector 2308 may be provided that allows for selection of specific permissions with respect to one of the central server 120 or permissions related to local systems 110. That is, selection of the central server 120 in the location selector 2308 may provide permission identifications for selection relating only to the central server 120. Selection of a local system 110 in the location selector 2308 may provide permission identifications for selection relating to the local system 110. Accordingly, upon selection of the desired location using the location selector 2308, a permission listing 2310 that includes all available permission identifications is listed. It may be appreciated that the permission data may include permission identifications for both the central server 120 and local system 110. In this regard, a first permission identification may be provided related to the central server 120 and a second permission identification may provided related to the local system 110.

The user may use selection buttons 2312 to add or remove permissions from a selected permissions field 2314. In this regard, the permission identifications for either or both of the central server 120 as well as for local systems 110 may be selected by a user for a group using the permission editing interface 2306. The permission identifications may correspond to any or all of the identify permissions described above in relation to the central server 120 and local systems 110.

FIG. 25 shows a user listing 2402 that includes each specific individual user for which permission data is to be provided. The user listing 2402 may allow for users to be added or deleted from the listing. Furthermore, upon selection of a user from the listing, user parameters may be edited in a details interface 2404. The interface 2404 may allow a user to input an abbreviation, a full name, and for an email address associated with a selected user from the user listing 2402. Furthermore, a selected user may have a password established or edited using the interface 2404. The interface 2404 may also allow a selected user to be indicated as being active and/or disabled. Further still, a support user group selector 2406 may be provided in the interface 2404. In this regard, a selected user may be associated with a support user group. In this regard, a group from the group listing 2302 (from FIG. 24) may be selected using the selector 2406 to be associated with a given user. In this regard, the user may inherit each permission identification provided to the group with which the user is associated. As such, when a user is associated with the support user group, the permissions associated with the support user group as shown in FIG. 24 may be provided to the individual user associated with the group. Accordingly, permission data may be provided for each user in the system upon association with a support group for which permission identifications have been defined. These permission identifications, along with the support user groups and individual users associated there with may be stored as permission data to be provided in a manner described herein.

In turn, the permission data defined using the user management portal 2018 shown in FIGS. 24 and 25 may be stored at the central database at 2022. For instance, in the context of the distributed healthcare information management system 100 shown in FIG. 1, the permission data may be stored at the central database 390. In further relation to the context of the distributed healthcare information management system 100 employing central support user management, it may be particularly advantageous to provide permission data from a central database 2022/390 to a plurality of local systems 110. For example, the transmission of this permission data may allow support users to access a local system 110 from the central server 120, thereby providing the benefits described above in relation to the ability to control access information and identify specific users taking action at the local system 120.

In such a distributed system, the permission data may be transmitted from the central server 120 on a periodic basis to the plurality of local systems 110. For instance, the central server 120 may transmit the permission data at a regular reoccurring time periods (e.g., every minute, every five minutes, every 15 minutes, hourly, daily, etc). Furthermore, the central server 120 may transmit permission data to the plurality of local systems 110 upon any change to the permission data. Additionally or alternatively the permission data may be transmitted from the central server 120 on request by a given local system 110.

Furthermore, regardless of the frequency or trigger of the transmission of permission data from the central server 120 to the local systems 110, the local system 110 may be operative to verify successful receipt of the permission data at the local system 110. In turn, the local system 110 may provide confirmation of successful receipt of permission data the local server 120. In turn, in future transmissions of permission data from the central server 120 to local system 110, only the permission data that has been modified since a prior transmission to a given local system 110. This may reduce the amount of network traffic related to the provision of permission data between the central server 120 and a local system 110. In turn and with return reference to FIG. 23, in an embodiment a local system 110 (e.g., a client application server executing at the local system 110) may request 2024 permission data by transmitting a request 2027 directed to the central server 120. In turn, the central server 120 may retrieve 2026 the permission data for the support users and groups and provide 2028 such permission data to the local system 110. In turn, the local system 110 may update 2030 permission data stored locally at the local system 110 in a client database at 2032. For instance, in the context of the distributed healthcare information management system 100 shown in FIG. 1, the permission data received from the central server 120 may be stored at the local database 112. In turn, a user management module 2034 (e.g., the permission check module 2052 shown in FIG. 22) at the local system 110 may access the client database at 2032 to retrieve permission data for use in the determination 2010 of whether a user has access to a requested resource (as depicted in FIG. 22).

Furthermore, when permission data has been received 2028 at the local system 110, the local system 110 may update 2036 status information regarding each one of the support users and/or support user groups at the local system 110. This updating 2036 may include providing a confirmation of receipt of the permission data and/or an error log regarding the permission data in a transmission 2038 to the central server 120. Upon receipt of the transmission 2038, the central server 120 may have information related to the last successful permission data received by a local system 110. The central server 120 may then update 2040 the last time a successful permission data transmission was received at a given local client 110 and/or may generate an error report associated with the failure at the local system 110 to receive the permission data based on the transmission 2038.

In an embodiment, the local systems 110 may also verify the transfer of permission data to ensure the transmission of permission data from the central server 120 to local system 110 is not intercepted, modified, or otherwise corrupted during transmission. For example, the local system 110 may apply a checksum function at the file or record level of the permission data to verify correct transmission of the permission data from the central server 120. In turn, upon receipt of the permission data, the local system 110 may be operative to apply a checksum to the received permission data to verify that no errors are detected in connection with the receipt of the permission data. For example, the checksum may include a checksum function or a checksum algorithm such as a hash function, a fingerprint, a randomized function, or a cryptographic hash function that is applied to the permission data to verify there are no errors in the permission data received at the local system 110 upon receipt from the central server 120. Accordingly, the use of a checksum may be employed to detect errors or other corruption in the permission data in connection with the transmission from the central server 120 local system 110. In turn, the confirmation provided from the local system 110 to the central server 120 may include information related to the success or failure of receipt of the permission data at the local system 110.

Additionally and as described above, the permission data provided by the central server 120 to the local system 110 may only include permission data that has been modified since the last successful transmission of permission data to a given local system 110. Specifically, confirmation provided from the local system 110 to the central server 120 upon successful receipt of permission data from the central server 120 may allow the central server 122 track the last time in which permission data was received at the local system 110. For example, the confirmation from the local system 110 may provide information related to successful receipt (e.g., where a checksum verifies no data errors were contained in the permission data) and/or may contain error logs regarding unsuccessful receipt of permission data from the central server 120. In any regard, the local system 110 may provide a communication to the central server 120 that allows the central server 120 to maintain a record of the last successful permission data provided to the local system 110. As described in greater detail below, the record of the last successful permission data provided local system 110 may be in the form of a timestamp, a hash value, or other mechanisms known in the art that allows tracking of updates to database records.

In this regard, the central server 120 may timestamp data records to indicate the time/date at which modifications to the permission data records are made using the support user management module 128. Accordingly, by using the timestamps associated with modifications of the data records in combination with the record regarding the last successful transmission of permission data to a given local system, only permission data records that have been modified since the last successful transmission of permission data may be provided when a local system 110 requests the permission data. In this regard, timestamping modifications of the permission data at the central server 120 may be provided in plaintext such that a comparison of the modification timestamp associated with the permission data may be directly compared to the time of the last successful transmission of permission data to a local system 110 to determine what portion of the permission data is to be transmitted to the local system 110 in a subsequent transmission (e.g., only the permission data having a timestamp for modification since the last successful transmission of permission data to a local system 110).)

In another embodiment, a hash value may be computed for permission data by applying a hash function (e.g., a cryptographic hash such as SHA, MD5, variants thereof, or other known cryptographic hash functions) to the permission data upon transmission of the permission data to the local system 110. In turn, upon successful transmission and confirmation of receipt of permission data from the central server 120 to the local system 110, the hash value associated with the last successful permission data transmitted to the local system 110 may be maintained at the central server 120. In turn, upon a subsequent transmission of permission data to the local system 110, the central server 120 may apply the hash function to the permission data at the time of the subsequent transmission and determine whether the resulting hash value is equal to the prior hash value associated with the last successful transmission the local system 110. In the event the hash values agree, it may be determined that the local system 110 successfully received the permission data and no subsequent changes have been made. However, if the hash values differ, updated permission data may be provided to the local system 110 based on the determination that updated permission data exists in view of the difference in the hash values between the previous transmission and the currently contemplated transmission. Such hash functions may be applied at a file or record level to determine which files, records, or even partial permission records of the permission data are to be transferred in a subsequent transmission. Accordingly, verification of receipt of permission data may occur at the local system 110 and provision of only permission data that is updated since the last successful transmission of the permission data may be provided to the local systems 110.

Figure 26:
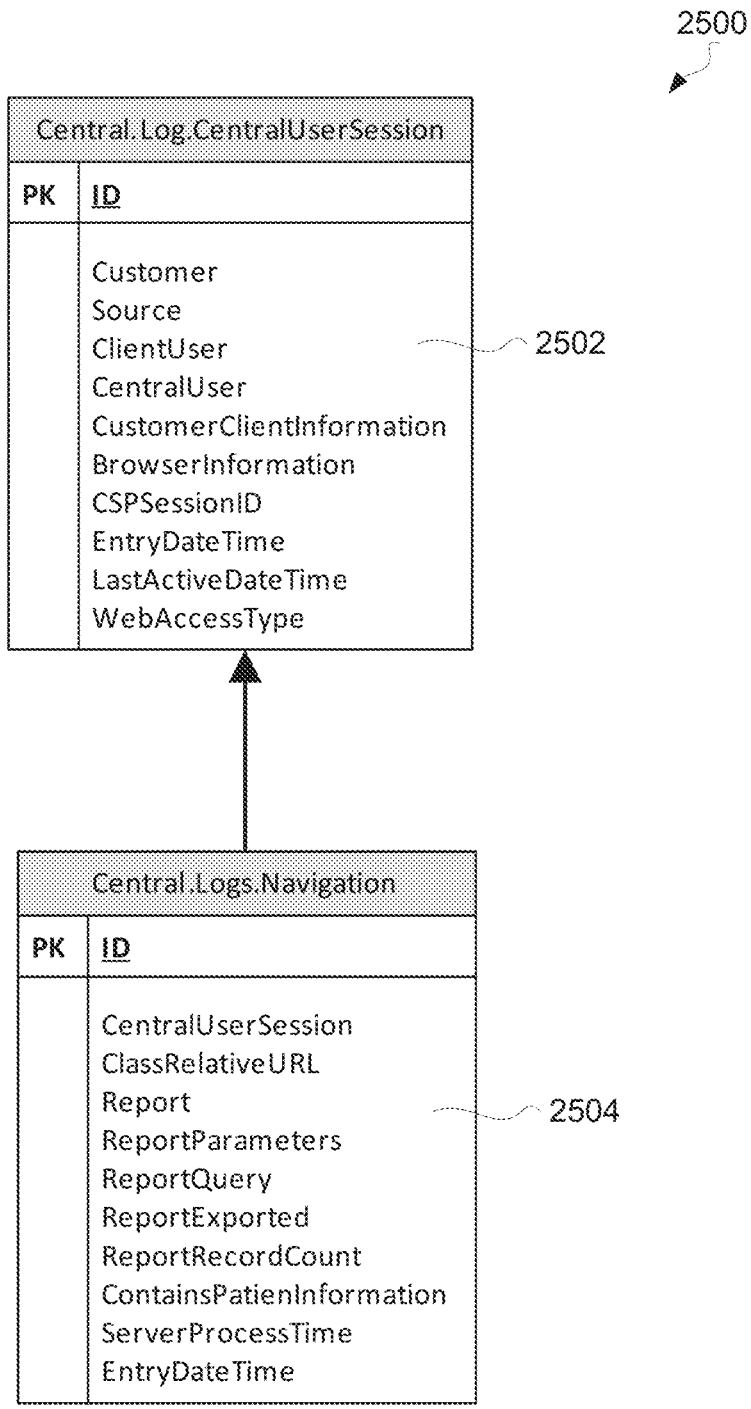
FIG. 26 depicts an embodiment of a database schema corresponding to database records recorded during logging operations in an embodiment of centralized support user management.

As described above, upon accessing a resource by a user, the method 2000 shown in FIG. 22 may include logging 2014 a user session as well as logging 2016 navigation of the user when accessing a resource. The logging 2014 and 2016 provided by logging modules 2054 and 2056, respectively, may be provided as components of a web service module 2050. With further reference to FIG. 26, an embodiment of a database schema 2500 is shown. The logging modules 2054 and 2056 may generate a log record in accordance with the schema 2500 upon a user accessing a resource.

For instance, a session record 2502 may be generated at the logging 2014 to record parameters regarding a session associated with a user accessing a resource. As shown in FIG. 25, the session record 2502 (e.g., as defined by the schema 2500 shown in FIG. 25) may include an identification of the customer (i.e., the local system 110) from which a user is accessing the resource. Alternatively, if the user originates from the central server 120, the SourceField of the schema may be used to indicate that the user accessing the resource is doing so from the central server 120 in the session record 2502. The session record 2502 may also record the user name in either the ClientUser field or the CentralUser field, depending upon whether the user is accessing the resource from a local system 110 or the central server 120 respectively. Furthermore, if the user is accessing a resource from the client application server (e.g., the local system 110), a pointer to that location's system statistics may be provided in the resulting session record 2502 in the CustomerClientInformation field of the schema 2500. This record may contain information regarding the user's machine name, operating system, etc. Furthermore, the BrowserInformation field may record information regarding the browser used to access the resource. The CSPSessionID field may record the session key used to enter the central server application. Furthermore, the date and time the record 2502 is generated may be recorded in the EntryDateTime field, the date and time the user last accesses the resource during a session (i.e. as the user navigates to different pages, the last active date and time may be updated to reflect the user's last activity in the current session) may be recorded in the LastActiveDateTime field, and the identity of the resource accessed may be stored in the WebAccessType field.

Figure 20:

Furthermore, sub records in the form of a navigation log record 2504 may be created for each session record 2502 as part of the navigation logging 2016 of FIG. 20. The navigation log record 2504 may store a user's navigation (i.e., activity) within a resource for a given user session with which the navigation log record 2504 is associated. That is, each time a user navigates to a page or resource, a navigation log record 2504 may be generated to record the user's activity. Each entry will log the identity of the resource accessed and ancillary information. For example, if the user generates report, the information may also be logged in the navigation log record 2504.

In this regard, each navigation log record 2504 may include a description of the associated user session (i.e., a reference to the session record 2502 with which the navigation log record 2004 is associated) in the CentralUserSession field. The relative URL path of the resource (e.g., webpage) accessed may be stored in the field ClassRelativeURL. If the resource being accessed comprises a report, the field Report may indicate as such. Furthermore, details of the nature of the report may be stored in the navigation log record 2504. For example, the parameters used to execute the report may be stored in the field ReportParameters, the SQL query used to execute the report may be stored in the field ReportQuery, an indicator as to whether the report was exported may be stored in the field ReportExported, and the number of records in the report results that may be stored in the field ReportRecordCount.

Furthermore, a field ContainsPatientInformation may be provided in the navigation log record 2504 to indicate whether the user accesses any resource that contains protected health information (PHI). As used herein, protected health information may include any patient identifying information such as, for example, patient name, patient identifier, patient date of birth, patient security number, patient telephone numbers, or other relevant information that identifies the patient. In this regard, PHI, as contemplated herein, may include, but need not be limited to, the definition of PHI provided in the Health Insurance Portability and Accountability Act (HIPAA). That is, as utilized herein, PHI may include a definition of information that coincides with the definition provided by HIPAA, but may also include any patient identifying information or subset thereof.

In any regard, if a user accesses a resource that contains PHI, the ContainsPatientInformation field may indicate as such. In one embodiment, the ContainsPatientInformation field may be at least partially based on a resource flag that is indicative of whether the resource includes PHI. In this regard, the resource flag may be a preset value for certain pages that are known to include PHI. Furthermore, for pages that may or may not include PHI, the resource flag that is indicative of whether the resource includes PHI may be dynamically generated. For example, when running a report, certain record fields in the report, if requested, may result in the resource flag being set to indicate that the report includes PHI. These record fields may be predefined such that the record fields may be indicated in the database as contain PHI such that if any such record fields included in the report, the ContainsPatientInformation field may be dynamically updated to indicate whether the user access to resource containing PHI. Further still, a given resource may be assumed to contain PHI. For instance, resources provided at a given location (e.g., the local device) may have a resource flag that indicates the resource contains PHI based on the location at which the resource is provided. This may help provide a safeguard against unauthorized or unintended access to PHI.

Furthermore, the navigation log record 2504 may further include administrative information such as the time it took to load it resource in the ServerProcessTime field and/or the date and time the navigation log record 25 before was entered in the EntryDateTime field.

Accordingly, use of the central support user management described above may allow central support users access local systems 110 to provide routine maintenance, troubleshooting, or other technical support services in relation to local systems 110. This may be particularly helpful in that central support users may comprise developers, technical support staff, or other users knowledgeable about the client applications executing at the local systems 110. For example, as described above, the central server 120 may be executed or facilitated by a provider of the pharmacy workflow management application 114 that is described below. Because specific individual support users may have corresponding permission data provided to the local systems 110, each specific individual support user may have appropriate permissions data provided for that user and that user's actions may be logged as described above. As each specific individual support user may have permission data associated there with, upon modification of a user's role, the permission data associated with that particular user may be easily modified and that modify permission data may be shared with local systems 110 as described above. Additionally, the ability to share permission data among systems of a health information management system 100 described above may be advantageous in that users from local systems 110 may also have permission data easily and efficiently associated there with in the manner described above. This data may also be shared with a central server 120 such that access to resources at the central server 120 may also be governed under the role-based security model facilitated by the system described above. In turn, a more robust role-based security model may be provided that allows for increased controls on user permissions and further facilitates specific user tracking in the form of logging as described above.

Accordingly and as described above, one particular context in which the foregoing support user management may be advantageously implemented is in the context of a healthcare information management system that includes a health information management application such as a pharmacy workflow management application 114 executing at a local system 110 that is in operative communication with a central server. In this regard, the following description relates to specific embodiments of pharmacy workflow management application 114.

In this regard, the local systems 110 may comprise a number of hardware and/or software modules that comprise the pharmacy workflow management application 114. For instance and with returned reference to FIG. 1 each local system 110 may include a local database 112 for storage of information. As may be appreciated, the local database 112 may in fact include a collection of one or more databases collectively referred to as the local database 112. In an implementation of the present invention, the local system 110 may include a server that facilitates access to the database 112. The database may store data related to the current in process work and/or store archival data related to prior work completed at the pharmacy. The local database 112 may be a high-performance, highly scalable and SQL-compliant object database. In this regard, the database may scale easily to handle thousands of simultaneous users and potentially terabytes of data.

In addition to storing information related to pharmacy work (i.e., dose order records), the database 112 may include information in a variety of contexts including information related to formulary information, administrative information, permission data as described above, or other information related to the pharmacy workflow management application 114 at the local system 110. In any regard, the local system 110 may execute a number of services (e.g., provided by modules executed by a processor). For instance, a data backup module may be provided that provides a rule-base approach to data backup from the local system 110 to the central server 120. The data backup module may define the interval at which the local system 110 provides backup data to the central server 120 and/or may dictate what information is provided to the central server. The backup module may also provide an administrator (e.g., at the central server or the local system 110) with information relating to the success or failure of data backup operations, system slowdowns, and the like. For instance, the backup module may facilitate selective backup of the local database 112 as described in U.S. Patent Application No. 62/019,227 incorporated by reference above.

Each local system 110 may also include a formulary management module that allows a pharmacy formulary to be maintained.

Figure 2:
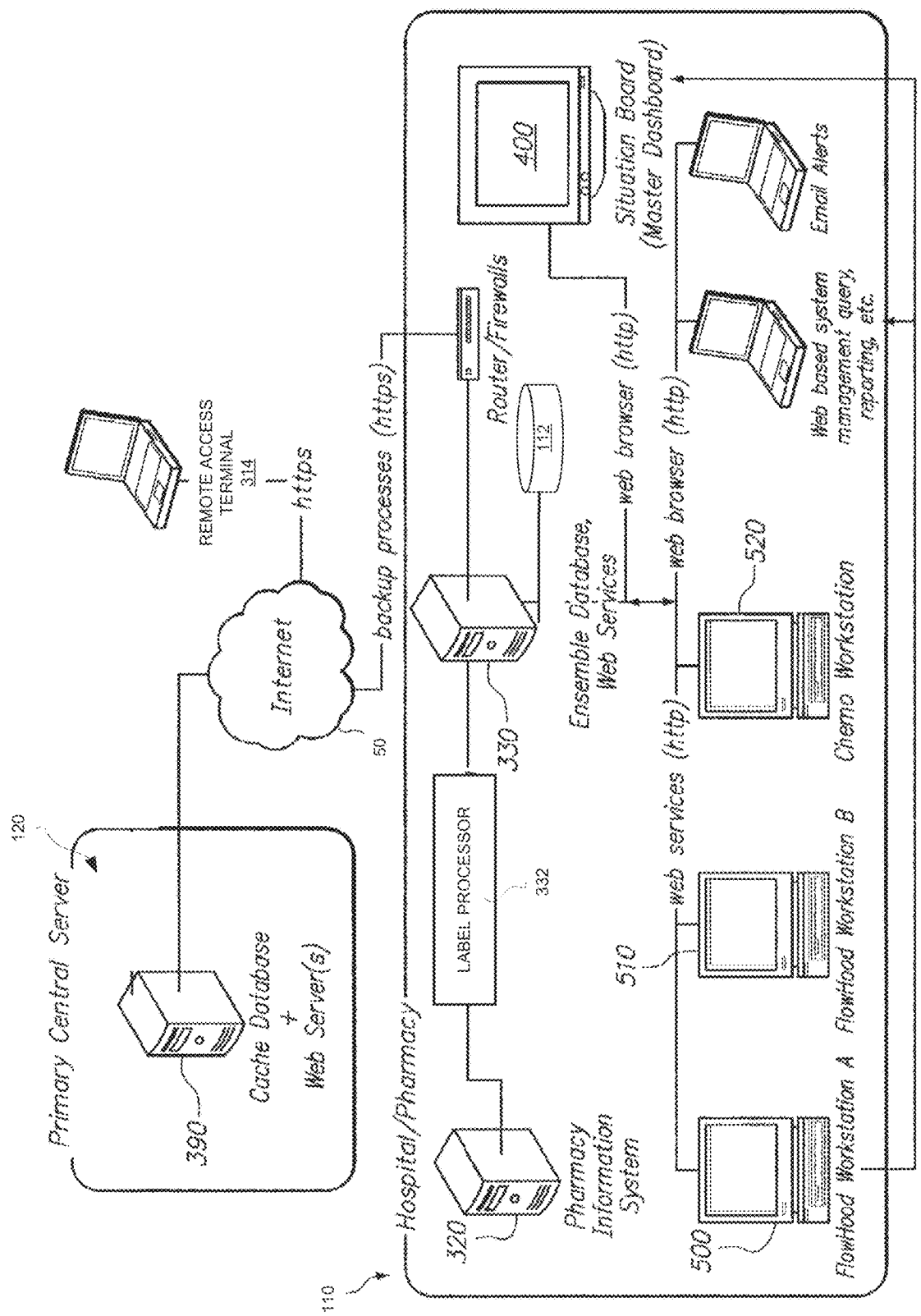
FIG. 2 is a schematic view of an embodiment of a local system comprising a pharmacy workflow management application that may form part of the healthcare information management system depicted in FIG. 1.

With further reference to FIG. 2, a schematic view of an embodiment of a local system 110 in operative communication with a central server 120 is depicted. Again, the local system 110 may execute a pharmacy workflow management application 114 for processing dose orders to prepare corresponding doses for administration to a patient. As may be appreciated, the local system 110 may, in at least one embodiment, include a pharmacy information system 320. The pharmacy information system 320 communicates to a local server 330. The local server 330 may store and/or provide access to the local database 112. A label processing module 332 may be provided between the pharmacy information system 320 and the local server 330. The label processing module 332 may intercept a message or data stream from the pharmacy information system 320. In turn, the label processing module 332 may provide data to the local server 330 for creation of a dose order record at the local server 330 in response to the label processor 332 receiving dose order information from the pharmacy information system 320.

As such, the local system 110 (i.e., a pharmacy, hospital, or other facility capable of preparing doses for administration to a patient) may receive or generate dose orders. Dose orders may be received at the local system 110 in one or more different ways. By way of example, in an embodiment a doctor or other appropriate medical personnel may enter one or more dose orders directly using the pharmacy information system 320. In this regard, the pharmacy information system 320 may provide an appropriate terminal accessible by the appropriate medical personnel for entry of the dose order. Additionally or alternatively, appropriate medical personnel may enter dose orders at a remote access terminal 314 that may provide order data to the label processor 332 in the local system 110 by way of the wide area network 50. As may be appreciated, the remotely entered dose orders may be communicated to the label processor 332 by way of a local server 330. In this regard, the local server 330 may include web services that facilitate the communication of dose orders from the remote access terminal 314 to the label processor 332. As the remote access terminal 314 may be remote from the local system 110, one or more routers or firewalls be provided to assist in securing the communication between the remote access terminal 314 and the local server 330. Further still, the pharmacy information system 320 may receive dose orders from and/or be a component of a larger hospital information system that may be capable of receiving and/or generating dose orders. In this regard, the hospital information system may provide information to the pharmacy information system 320 and/or directly to the label processor 332 as described in greater detail below. Any communication into or out of the local system 110 and/or any communication within the local system 110 may be secure. For example, various security protocols such as https, SSH, VPN, DES encryption, RSA encryption, or any other known security protocol to secure communication between nodes in the network.

In any regard, the pharmacy information system 320 may receive data from which information related to one or more dose orders may be extracted. That is, dose orders corresponding to requested doses for administration to a patient may received at the local system 110 and routed to the label processor 332. While present disclosure generally includes a description of label processing, label processing module may also be of any type described in commonly assigned U.S. Pat. No. 7,069,212, which is hereby incorporated by reference in its entirety.

In traditional approaches to pharmacy management, when dose orders are received at a facility, a corresponding physical label for the dose order is printed within the pharmacy. In turn, traditional workflow management in the pharmacy is relegated to management of the physical labels, which may be disadvantageous in that the physical labels may be lost, the physical labels may be difficult to organize, the use of physical labels introduces additional potential for human error, and the production of physical labels may not provide reliable logging for later auditing.

In contrast, when the dose orders are processed by the label processor 332, rather than only a label for medication order being printed, data related to the order (e.g. data that have traditionally been printed on the label corresponding to the order) may be captured, processed, and parsed in the computer implemented systems to create individual medical dose order records, each of which corresponds to a corresponding dose order, that are in turn stored in the local server 330. That is, rather than printing a label for a medication order, the order may be utilized to generate a digital dose order record that is stored at the local server 330 (i.e., in the local database 112). Data used to generate the digital dose order record may be taken from the medication order data received at the local system 110. As such, a dose order record may be generated and stored at the local server 330 that corresponds to each given medication order received at the local system 110. Thus, rather than having to manage physical printed labels at the local system 110, the received medication orders may be managed digitally utilizing the local server 330 that stores the dose order records corresponding to each medication order received.

Figure 3:
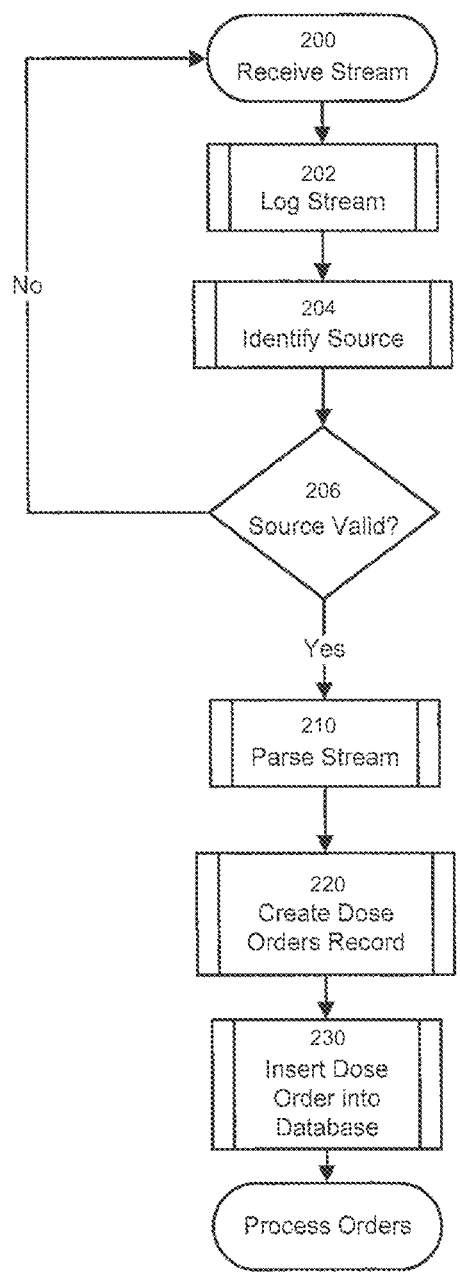
FIG. 3 is a flow chart depicting an embodiment of a method for receipt and processing of dose orders.

With reference now to FIG. 3, an embodiment of process is illustrated in which dose orders are received and processed to generate and store dose order records at the local system 110. At step 200, one or more medication order streams are received at the local system 110 (e.g., from a local data stream or a remote data stream as described above) and are processed by a label processing module 332. The label processing module 332 may comprise a processor that accesses a memory comprising code that is executed by the processor (e.g., at the local server 330) to perform the processes in FIG. 3. That is, the label processing module 332 may be separate from or comprise a part of the local server 330. In one specific embodiment, the medication order data can be captured by a monitoring module comprising computer code executing on a processor in the pharmacy for monitoring a port normally connected to a pharmacy printer, network monitoring for medication order information, or software application monitoring for events related to the input of medication orders. As described above, traditionally these order streams may represent data intended to be printed on labels on a printer, and oftentimes comprise serial data streams.

The medication order streams may contain a list of medication doses to prepare. Each dose order and dose is preferably associated with additional related data such as, for example, the patient for whom the medication is intended, by when it should be delivered, and to where it should be delivered, the ordering doctor, the time and date the prescription was entered, the reason for medication, and other relevant information associated with a dose order or any other appropriate metadata described in further detail below that may be present in the mediation order stream for each dose order contained in the stream. Such information may be used when generating a dose order record to populate appropriate dose order record data fields for a dose order record that correspond to respective ones of the medication dose orders contained in the medication order streams. As will be discussed in greater detail below, additional dose order metadata that may be added to the dose order record during the preparation, approval, and/or distribution of the dose order corresponding to the dose order record. The dose order record and all related dose order metadata may be stored in the local database 112.

Data streams containing medication dose order data that are received at the local system 110 are preferably logged at step 202 by a monitoring computer. Preferably, streams are logged in the local database 112 or other computer accessible medium (e.g., at the local server 330). Logging data streams enables extensive auditing and monitoring of the pharmacy, hospital, or other facility that dispenses medication. Because all data is logged, preferably in its raw form when it is first received by the pharmacy, no information is lost, corrupted, or disassociated during the processing or distribution of the medication. If necessary, an audit can be performed manually, off-line, or by a separate software program to reconstruct the data stream and all processing that should have or did occur after the pharmacy received the data stream.

Preferably, a data stream containing dose orders that is received at the local system 110 has an identifiable source. The source can be explicitly identified within the stream of data, or it can be determinable by the system. Source determination can include, for example, examining TCP/IP packet or header/footer information, examining cryptographic signatures of the stream, or data retrieved through additional network communication requesting the source. In any regard, the source may be identified at step 204.

At step 206, the system may be configured to determine whether the data stream originated from one of a set of valid sources. This can include identifying the source of the data stream and testing that it is one of the sources among those in the set. Validating the source ensures each medication dose prepared by the pharmacy workflow management application 114 is legitimate and originating from an authorized prescribing or ordering entity. Alternatively, the validation can ensure that the prescribing entity is presently entitled to have its prescriptions filled by the pharmacy. If the source is not valid, the system returns to step 200 to receive additional streams. Optionally, notifications can be sent to the source to inform it that there were validation issues or that the window for continued validation has one or more constraints (e.g., will expire in so-many days due to an overdue invoice).

After determining that the source is valid, the stream may be parsed to extract relevant information at step 210. The system can parse various message and data formats. Moreover, the parser can be extensible, such that as new formats are implemented or included within the networked environment, a parser extension can be included in the system to parse the new format. For example, if the data stream is a serial printer data stream, the system can determine the format of the data and pass the stream to the appropriate serial printer data parser. The printer data parser is configured to extract the dose order information contained within the stream and may populate dose order record data fields of a dose order record with the parsed data from the data stream corresponding to any one or more portions of dose order metadata described in more detail below. Preferably, the parser extracts all relevant data contained within the stream and maintains a record of the extracted data. The parsing methodology is preferably encapsulated in a library or set of modules that are called upon, as necessary, to parse a stream of any determined format. Each library entry or module operates as a "parser," as that term is used herein.

As described above, the data stream may contain one or more dose orders. For example, the stream may contain a single dose request by a doctor for a single patient. Alternatively, the stream can include multiple dose orders that may be delineated by the parser into separate dose order records corresponding to each distinct dose order. That is, the parser is preferably configured to recognize and discriminate between individual dose orders within a stream. In turn, dose order records may be created and populated for each corresponding one of the individual dose orders within a stream. The discrimination of individual dose orders can be accomplished by recognizing an order delimiter, or alternatively can be defined by the format of the data stream.

In any regard, once the stream is parsed at step 210, a dose order record may be created at step 220. In turn, the dose order record may be stored at the local database 330 at step 222. In this regard, the data stream may be received 200, logged 202, and parsed 210 to create a corresponding dose order record for each dose order contained within the stream. In turn, the medication stream received at the local system 110 may be used to generate dose order records stored in a local server 330 for each medication dose order to be prepared at the local system 110.

As briefly described above, having dose order records stored digitally in the local database 330 may facilitate improved management of the dose order records during preparation in the pharmacy. In turn, the following describes some embodiments of dose order record management performed at the local server 330 to facilitate pharmacy workflow management by the pharmacy workflow management application 114. Specifically, dose order records may be easily viewed, sorted, searched, prioritized, or otherwise organized by pharmacy technicians or other personnel who have appropriate access to the local database 330. Furthermore, as data is generated in the pharmacy regarding the dose order (e.g., during the preparation, approval, or distribution of a dose), such data may be stored in relation to the medication dose order record to provide a more robust data set associated with each medication dose prepared at the pharmacy. As may be appreciated, the amount of data related to each digital dose order record may be extensive. The data related to the dose order record may be referred to as dose order metadata. In turn, dose order metadata may be stored in corresponding dose order record data fields and may describe various characteristics of the dose order, a dose corresponding to the dose order, the preparation of a dose, or other relevant characteristics related to the dose or dose order.

For instance, examples of dose order record data fields may include, but are not limited to:
  dose order status information indicative of at least one of:
    a preparation status of the dose order (e.g., pending, at preparation station, ready for verification, undergoing verification, approved, rework, requeue, awaiting sort, discontinued, etc.),
    a priority status of the dose order (e.g., STAT, first dose, etc.),
    a wait status (e.g., including a time at which the dose order become available to be made),
    a hold status, dose order administration data indicative of at least one of:
  a patient to whom the dose order is to be administered,
  a time of administration (e.g., including date and time of administration),
  a beyond use date (BUD) indicative of an expiration (e.g., time and/or date) of the dose order,
  an administration route of the dose order,
  a preparation mode of the dose order,
dose order identification information indicative of at least one of:
  a dose order identifier (e.g., a dose order record number),
medication source data indicative of at least one of:
  a manufacturer of a component of a product corresponding to the dose order,
  a lot number of a component of a product corresponding to the dose order,
  an expiration date of a component of a product corresponding to the dose order,
  a serial number of a component of a product corresponding to the dose order, or
  a drug code indicative of the identity of a component of a product corresponding to the dose order;
chain of custody data indicative of at least one of:
  a listing of entities in possession of a component of a product corresponding to the dose order or a product corresponding to the dose order,
  a listing of users that have taken an action with respect to a product corresponding to the dose order, wherein the listing of users is correlated to specific actions taken by each user, or
  tracking information corresponding to physical movement of a component of a product corresponding to the dose order or a product corresponding to the dose order;
fulfillment data indicative of at least one of:
  image data corresponding with a component of a product corresponding to the dose order or a product corresponding to the dose order,
  scanned data obtained from a component of a product corresponding to the dose order,
  analytic data regarding a component of a product corresponding to the dose order or a product corresponding to the dose order,
  pharmacist review data corresponding with at least one pharmacist review of a component of a product corresponding to the dose order or a product corresponding to the dose order,
  compliance data corresponding with best practices associated with a component of a product corresponding to the dose order or a product corresponding to the dose order,
  sterility assessment data corresponding to a component of a product corresponding to the dose order or a product corresponding to the dose order,
  a listing of actions corresponding to a component of a product corresponding to the dose order or a product corresponding to the dose order,
  timestamp data corresponding to actions corresponding to a component of a product corresponding to the dose order or a product corresponding to the dose order, or
  a listing of life cycle events taken with respect a component of a product corresponding to the dose order or a product corresponding to the dose order; or environmental data indicative of at least one of:
  a temperature to which a component of a product corresponding to the dose order or a product corresponding to the dose order has been exposed,
  a temperature to which and corresponding time period for which a component of a product corresponding to the dose order or a product corresponding to the dose order has been exposed,
  whether a component of a product corresponding to the dose order or a product corresponding to the dose order is refrigerated,
  whether a component of a product corresponding to the dose order or a product corresponding to the dose order is frozen,
  a temperature profile experienced by a component of a product corresponding to the dose order or a product corresponding to the dose order, or
  accelerometer data corresponding to forces experienced by a component of a product corresponding to the dose order or a product corresponding to the dose order.

Furthermore, because the dose order records are stored digitally at the local server 330, remote access be provided to those outside of the pharmacy to view, modify, and/or otherwise manage the digital dose order records stored at the local server 330. In turn, access to the data associated with the medication dose order records may be provided to remote users to assist in the management of pharmacy resources or the like. Accordingly, as will be discussed herein, a number of approaches to pharmacy workflow management may be facilitated that utilize the medication dose order records stored in the local server 330.

With further reference to FIG. 2, the local server 330 may be in operative communication with one or more local clients at the local system 110. For instance, the local client may comprise thick or thin clients executing at a terminal or workstation. In this regard, the pharmacy workflow management application 114 may comprise a web services application provided by the local server 330 accessed at a thin client by way of a web server. Additionally or alternatively, the pharmacy workflow management application may include thick client applications executing at a client that may communicate with the local server 330. The client applications may be provided at one more terminals locally at the local system 110 and/or remote from the local system 110. For instance, a client application may be provided on workstations that are equipped to prepare doses or terminals that provide access to information stored on the client server 330. The terminals executing the client application may include management terminals that may access and/or modify dose order records, review terminals that may allow a pharmacist to review doses, a situation board that displays relevant pharmacy information, or other appropriate terminals that facilitate functionality related to the pharmacy workflow management.

In an embodiment, at least one of the terminals may be provided as a remote access terminal 314 to facilitate access to the local server 330 from outside the local system 110. Such remote access by a client may be facilitated by way of secure communications (e.g., use of secure socket layer (SSL) communication, encryption, or other means of secure communication over a network such as those described above). Accordingly, once appropriate security measures of been taken, the remote access terminal 314 may execute a client application operable to communicate with the local server 330 in a manner similar to the local instances of a client within the local system 110. That is, the remote access terminal 314 may be provided with any or all the functionality associated with any of the local client device is described herein.

Given the foregoing architecture at the local system 110 where clients may access the local server 330 to manage various features of the pharmacy workflow management application, it may be appreciated that the local system 110 may be scalable with the addition of additional terminals, each executing a thick or thin client in operative communication with local server 330. Also, the architecture allows for remote access as described above. Further still, access by a terminal may be subject to the role-based security described above. That is, because dose order records stored locally at the local database 112 and are accessed by way of the client application, the management of the dose order records may be substantially simplified. For instance, while a client application may modify dose order record, the modification to the dose order record will be reflected at the local database 112. In turn, another terminal in operative communication with a local database 112 may be configured to receive updated data from the local database 112 (e.g., in substantially real-time) such that the modification of the dose order record from the client application may be reflected throughout the terminal with access to the local server 112. This distributed model of dose order record management may provide robust capabilities, especially in the context of collaborative management dose order records.

A workstation (i.e., a terminal where doses are prepared) may include a touchscreen, one or more barcode scanners, a label printer, a camera, etc. Additional hardware that may be present at the workstation may include a scale, a reconstitution module (mixing station) and/or a security ID badge reader. The hardware at the workstation may be operative to collect information regarding the preparation of a dose that may be stored in corresponding relation to the dose order record. Furthermore, the workstation may include traditional preparation apparatus used to prepare doses such as, laminar flow hoods, biological safety cabinets, or other pharmacy equipment used in the preparation of a dose.

In any regard, the local server 330 may be in bidirectional communication with any number of workstations to allow the workstations (e.g., 500, 510, 520, etc. as shown in FIG. 2) to receive information from the local server 330. For instance, each workstation may receive data regarding the dose order records stored at the local database 112 by way of the local server 330. This data may include all dose order records, collectively referred to as the dose order queue, stored at the local server 330 or may comprise a filtered dose order listing that only displays a selected number of dose order records from the dose order queue at a given workstation, referred to herein as a dose order record listing.

Figure 4:
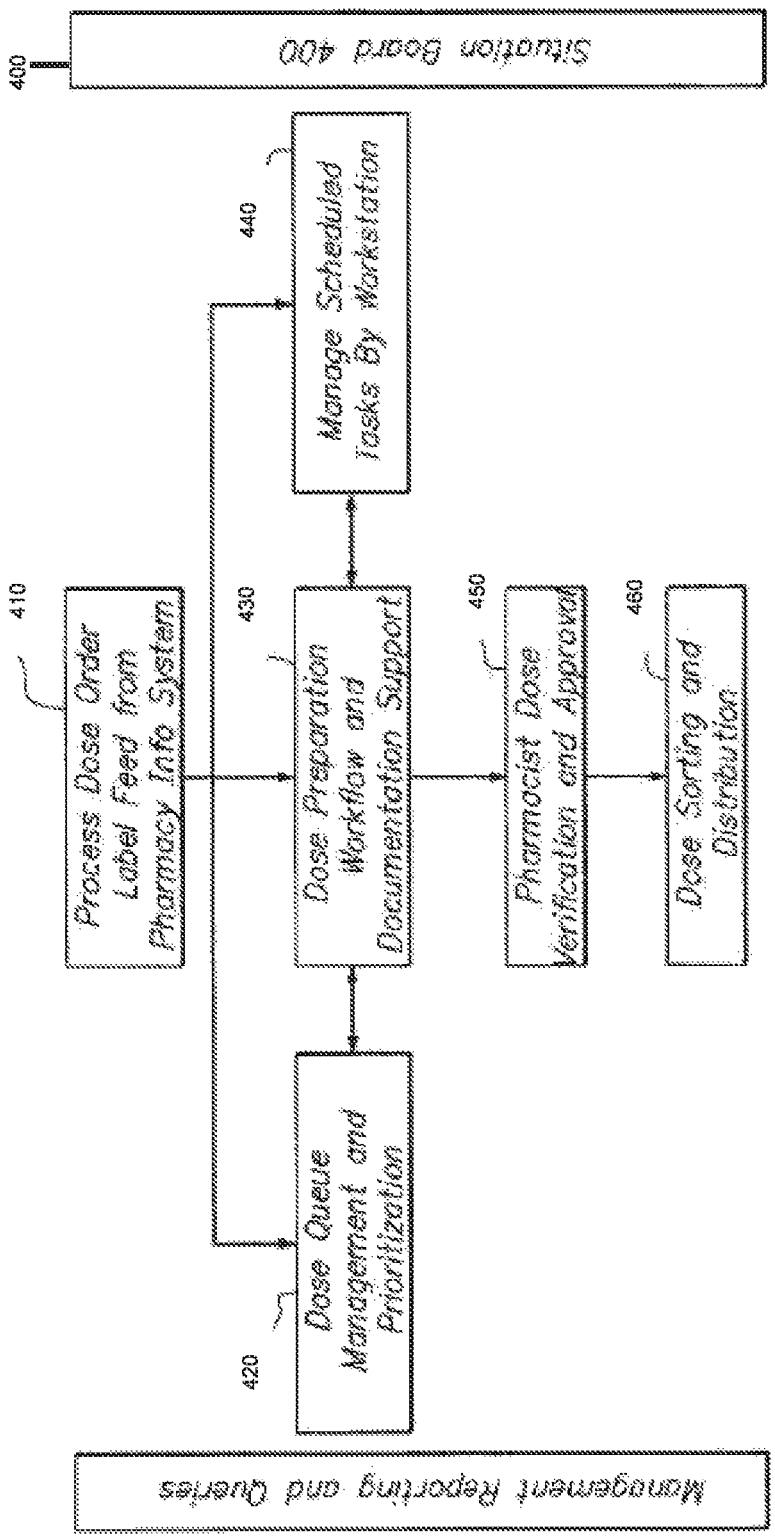
FIG. 4 is a schematic view depicting various functionalities of the pharmacy workflow management application executed by the local system shown in FIG. 2.
Figure 6:
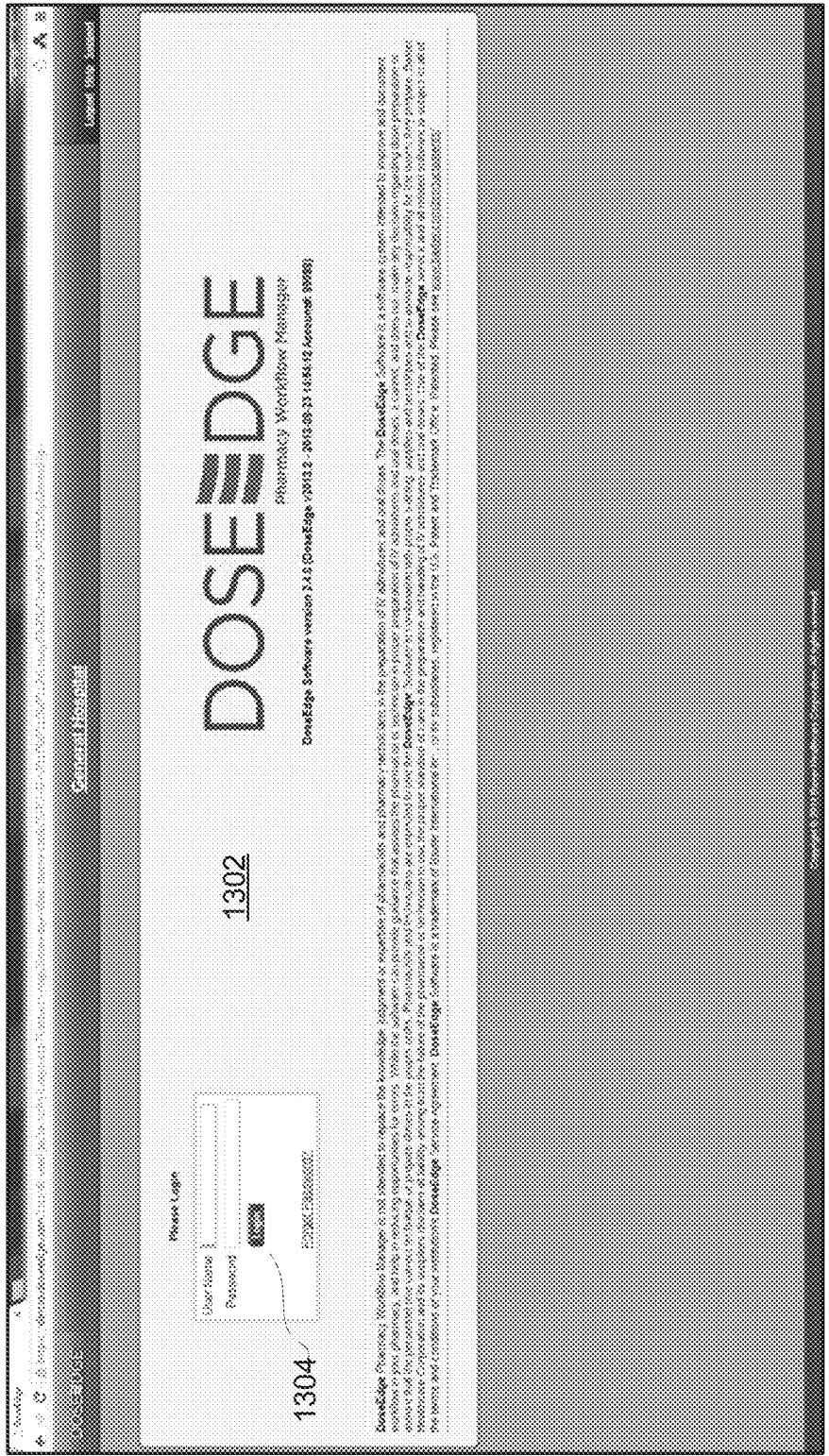

In turn, with reference to FIG. 4, once the dose orders have been processed 410 and provided dose order records stored in the local database 330, the pharmacy workflow management application 114 may provide for dose queue management and prioritization 420. Accordingly, an embodiment of dose queue management and prioritization 420 is described below.

Figure 5:
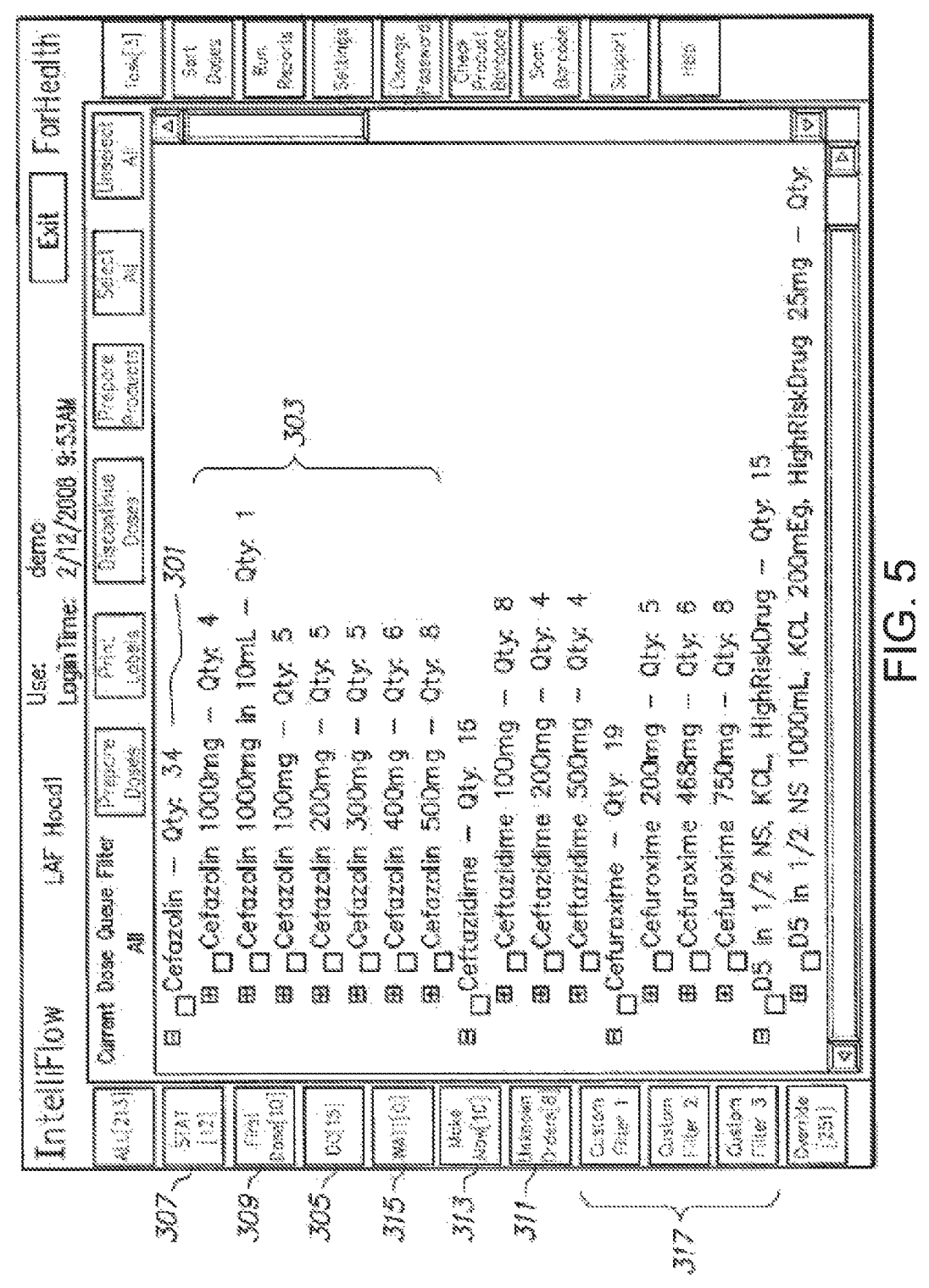

For example, at each workstation or other terminal, the dose order queue may be sorted and displayed as a dose order record listing that includes the dose orders records in any number of different ways. For example, the dose orders can be sorted and displayed by drug type and can be further sorted by dosage amount as shown in FIG. 5. The total amount of dose orders for each drug can be displayed next to the drug name in a main banner 301 and then underneath the main banner, the various drug dosage amounts are listed along with the quantity of each that is currently needed (lines 303). For example, as shown in FIG. 5, the main banner shows that there are 34 orders for the drug Cefazolin and underneath, the various drug dosage amounts, such as Cefazolin 1000 mg; Cefazolin 100 mg; Cefazolin 200 mg, are listed along with the quantity that is needed for each. Other examples of interfaces for filtering, displaying, and/or otherwise managing a dose order record listing are presented below.

Each dose order record listing can be displayed in a different manner to indicate information that is intended and helpful to the operators at the one or more workstations that process and fulfill the dose orders. For example, on the left column of the screen that is shown in FIG. 5, a box 305 labeled "DC" stands for discontinued dose orders which are orders that have been discontinued for some various reason and therefore, do not need to be processed and fulfilled. The box can have an associated color, such as purple, that allows individual dose orders to be indicated as being discontinued and therefore, should not be selected for processing and fulfillment. For example, the Cefazolin 500 mg (Qty: 8) dose order line can be displayed in purple, thereby indicating that this dose order is discontinued and should not be processed. Also along the left column are other status indicators, such as "STAT" 307, "First Dose" 309, "Unknown Drug" 311, "Make Now" 313 and "Wait" 315. These indicators can dictate a preferred order of selecting and fulfilling the dose orders. The status indicators may be stored as dose order metadata for a dose order record. The status indicators may be updated throughout the preparation process to provide the dose order record a different status based on the progress through the preparation process. Additionally, "First Dose" can indicate the highest priority dose orders which should be selected first before another dose order, including those dose orders that are labeled "STAT". Meanwhile, a situation board 400 provides an overview of the queue for all drug orders that are being handled. The situation board 400 may provide an overview throughout the entire process of order preparation as shown in FIG. 4.

In addition and with returned reference to FIG. 5, other options available for selection by the operator at a station can be displayed, such as along the left column. For example, one or more filters 317 can be employed by the operator to filter the dose orders that are listed in the dose order queue. The filter 317 can be selected among standard ones, such as a filter that lists only those dose orders that can selected and fulfilled by the operator at a given workstation or the filter can be designed to only show only those dose orders that are classified as STAT orders and/or those that are classified as First Dose orders. Alternatively, the filter can be a custom filter that is created and defined by the workstation operator.

The dose order queue may also be displayed at a remote access terminal 314. Thus, the remote access terminal 314 may be operative to display the dose order queue according to the foregoing (e.g., where dose orders may be sorted and/or filtered for display). Furthermore, an administrator with proper administrative privileges may be operable to manage the dose orders contained in the dose order queue. As may be appreciated, this management may be facilitated within a terminal within the pharmacy 310 or by way of a remote access terminal 314.

With reference to FIGS. 6-12, additional embodiments of various user interface screens for an embodiment of a dose order management tool 1300 are depicted. The management tool 1300 may be a web-based management tool that may be presented to a user in a web browser or the like. For instance, a user may navigate to a particular web address and be presented with a login screen 1302. The login screen 1302 may include an authentication field 1304 that may require, for example, a user name and password be entered by the user to facilitate confirmation of a user's authorization to utilize the management tool 1300 and/or access various functionality of the tool 1300. As may be appreciated, different user authorization levels may exist such that when a user logs in utilizing the authentication field 1304, various rights associated with the management tool 1300 may be allowed or blocked based upon the user credentials provided and the associated authorization level associated therewith as described above in relation to support user management.

Figure 7:
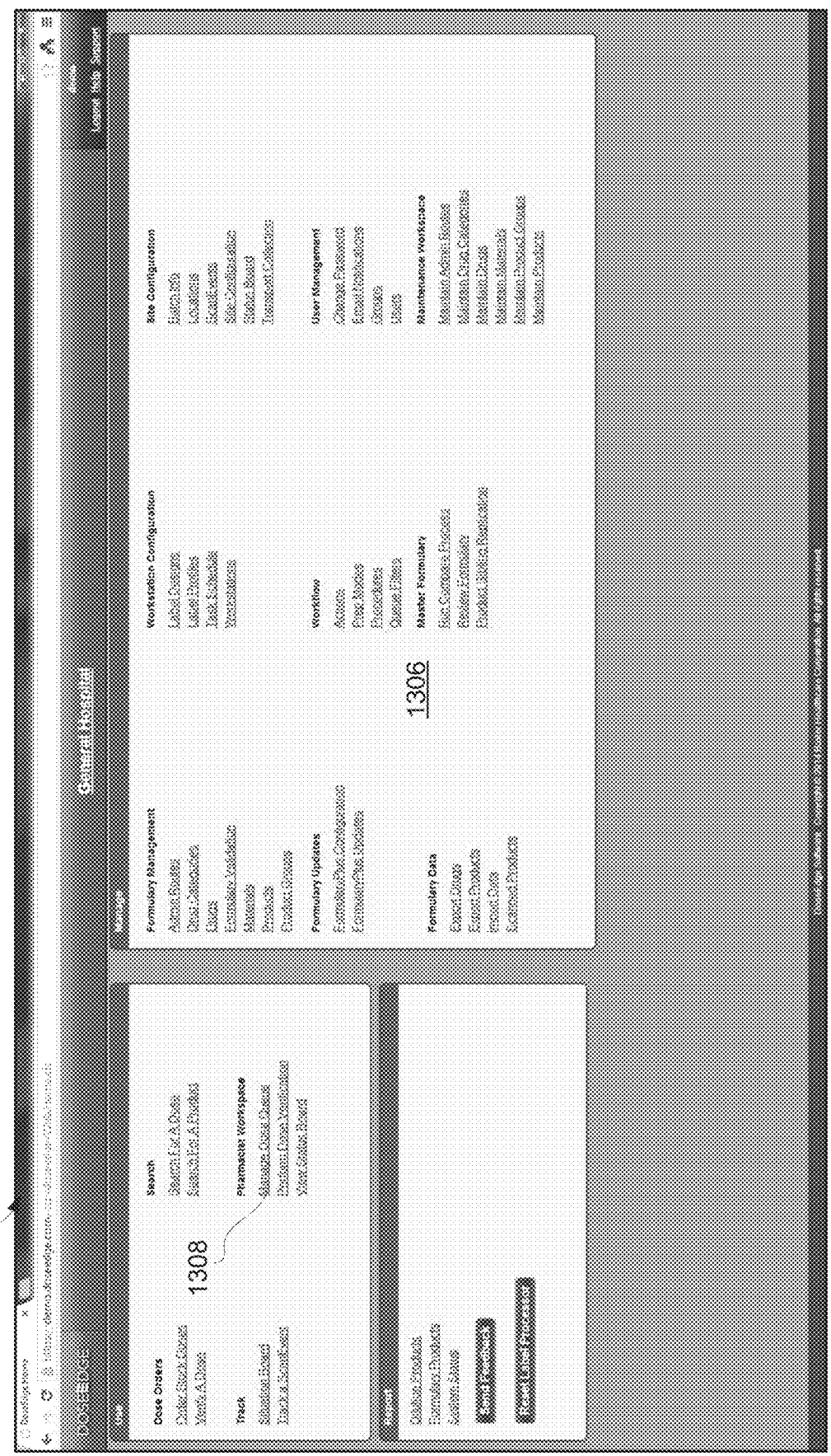
Figure 8:

With further reference to FIG. 7, upon successfully authenticating the user, a navigation screen 1306 may be provided to the user. The navigation screen 1306 may include a plurality of links associated with various functions of the management tool 1300. For example, the navigation screen 1306 may facilitate access to a dose order record listing for review or management of dose orders. Also, the navigation screen 1306 may facilitate access for a pharmacist to verification screens used to review and verify doses that have been prepared in the pharmacy by a pharmacy technician as are described in greater detail below. The navigation screen 1306 may include a link 1308 to a dose order management screen 1310. Selection of the link 1308 may result in the user being presented with the dose order management screen 1310 shown in FIG. 8.

The dose order management screen 1310 may include a dose order record listing 1312 that displays appropriate ones of the dose order records of the dose order queue stored in the local server 330. The dose order record listing 1312 may be arranged such that the individual dose order records are listed and divided by columns wherein each column corresponds with a different dose order record data field. As such, each dose order record data field column may be used to sort the dose order records in the dose order record listing 1312 (e.g., based on dose order metadata for each dose order record appearing in the dose order record listing). For example, the columns shown in FIG. 8 correspond to a dose identifier, does description, administration time, a relative time to administration, patient ID, patient name, patient location, a dose status, and a dose priority. In this regard, if desired the columns displayed in FIG. 8 may be used to sort the dose order record listing 1312 in ascending or descending order relative to the selected column.

The user may also utilize the dose order management screen 1310 to filter the display of the dose order record listing 1312. For example, the dose order management screen 1310 may include one or more tabs (e.g. 1314, 1316, etc.) that may be utilized to filter the dose order record listing 1312 according to status of the dose order records. For example, selection of tab 1314 by the user may filter the dose order records appearing in the dose order record listing 1312 such that dose order records with a status of "pending" may be displayed (i.e., including dose order records that have not yet been prepared). In this regard, selecting the tab 1314 may filter the dose order record listing 1312 such that dose order records but not yet been prepared may be shown. Selection of the tab 1316 may result in filtering of the dose order record listing 1312 such that dose order records are shown that have undergone preparation and are waiting verification by pharmacist. In this regard, the dose order records having a status indicating the dose orders are awaiting verification by a pharmacist may only be displayed in the dose order record listing 1312. It may be appreciated that additional tabs may be provided corresponding with different dose order statuses such as, for example, doses at initial review (i.e., doses not yet having been released for preparation), doses ready for preparation, doses awaiting in-line verification, verify doses awaiting sorting, doses awaiting rework, or any other appropriate status identifier that may be attributed to the dose order record.

The tabs 1314 or 1316 may also provide a user with a changeable graphical element that may allow for the user to be updated regarding various high-priority doses being added to the dose order record listing 1312. For example, if a STAT dose is populated into the dose order record listing 1312, a corresponding STAT dose indicator in the tab 1314 or 1316 may be updated to display the number of STAT doses currently in the dose order record listing 1312. Furthermore, the color indicator may be used to provide a quick reference to the user. For example, if a STAT dose is contained in the dose order record listing 1312, the STAT field in the tab 1314 or 1316 may be highlighted with a colored background (e.g., a red background that may be easily identifiable by the user even if not in close proximity with a display displaying the dose order management screen 1310).

The dose order management screen 1310 may also include a plurality of secondary filters 1318 that may be utilized to further filter the dose order record listing 1312. For example shown in FIG. 11, the secondary filters may include a selection of all doses, requeued doses, STAT doses, resume preparation doses (e.g., doses is preparation have been interrupted), rework doses, discontinue doses, doses placed on weight and/or hold, and suspected duplicate doses. It may further be appreciated that the secondary filters 1318 provided may be based upon the tab 1314 or 1316 selected. For example, when the tab 1314 is selected for display of dose order records that have not yet been prepared, the secondary filters 1318 displayed may include those listed above including an all dose filter, a requeued dose filter, a STAT dose filter, a resume preparation dose filter, a rework dose filter, a discontinued dose filter, a wait/hold dose filter, and a suspected duplicate dose filter. However, upon selection of tab 1316 to display dose order records that have been prepared and are awaiting verification, the secondary filters 1318 may be modified to include a wait/hold filter, and in-line filter (e.g., to only display doses awaiting in-line verification), a STAT filter, a final verification filter, and a being verified filter. A queue filter 1336 may also be provided to allow for configurable filters to be generated and applied to the dose order record listing 1312 based on a configurable comparison of the dose order queue to predetermined dose order record data field values as will be described in greater detail below.

Returning to FIG. 8, it may be appreciated that a dose order record 1320 may be selected from the dose order record listing 1312. The selected dose order record 1320 may be signified by a checkbox provided in the dose order record listing 1312 and/or highlighting of the selected dose order record 1320 from among the other dose order record in the dose order record listing 1312. As may be appreciated, multiple dose order records may be highlighted has selected dose order records 1320 such that batch processing may be facilitated on selected ones of the dose order records 1320. Selection of the selected dose order record 1320 may result in a plurality of dose order operation buttons being enabled. For example, dose order operations buttons may include a detail button 1322, a place on hold button 1324, a remove from hold button 1326, a discontinue button 1328, and modify button 1330. Selection of a dose order operation button by a user may result in performance of a corresponding operation to the selected dose order 1320. For example, selection of the detailed button 1322 may result in the dose order management tool 1300 displaying in detail screen providing additional details regarding the selected dose order 1320. Selection of the place on hold button 1324 may result in the selected dose order 1320 being placed on hold status. Selection of the remove from hold button 1326 may result in a selected dose order record 1320 that is currently a hold status being removed from hold status. It may be appreciated from FIG. 8, the selected dose order 1320 and the particular embodiment shown is not on hold, therefore the place on hold button 1324 may be enabled while the remove from hold button 1326 may be disabled. In contrast, if a selected dose order 1320 was a dose order with an on hold status, the place on hold button 1324 may be disabled and the removed from hold button 1326 may be enabled. Selection of the discontinue button 1328 may result in the selected dose order 1320 being discontinued (i.e., the status of the selected dose order 1320 may be changed to a discontinued status). Selection of the modify button 1330 may result in display of a dose modification screen 1348 that allows for one or more portions of dose order metadata to be modified as shown in FIG. 9.

Furthermore, the availability of a button for performing an operation relative to a dose order may be at least partially based on a level of authorization of a user. In turn, the enablement of one or more of the buttons that provide management functionality relative to the dose orders appearing in the dose order record listing 1312 may be based upon permission data as described above. As such, for example, a user may have the ability to place a dose order on hold or remove a dose order from hold using the place on hold button 1324 or remove from hold button 1326, but not have sufficient authorization to modify a dose order using the modify button 1330. Further still, a user may have authorization to view a dose order record listing 1312 alone without any authorization to modify a dose in any regard. Each of these permission identifications may be provided in permission data relative to the user.

Figure 9:
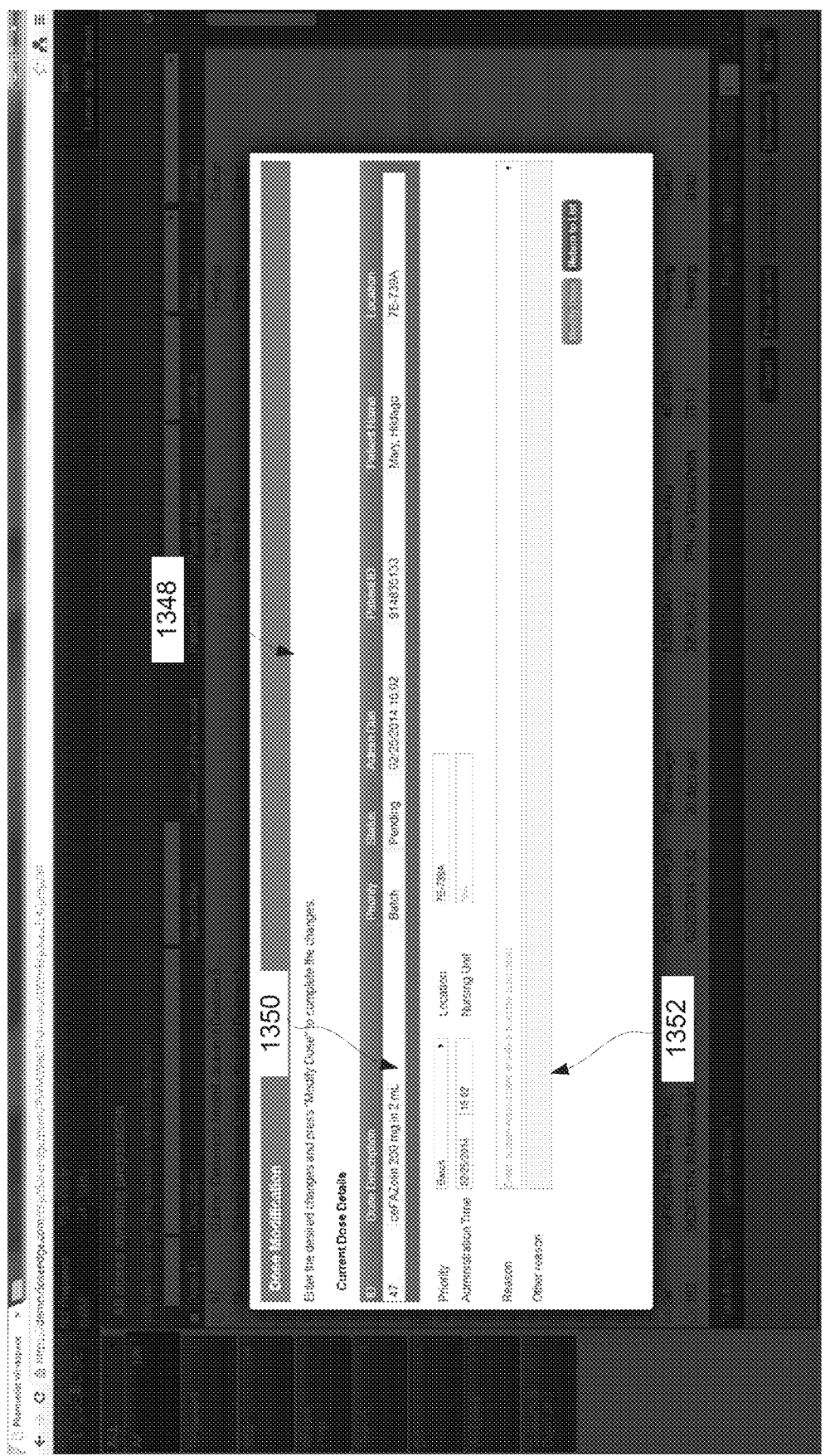

With continued reference to FIG. 9, the dose modification screen 1348 may be displayed upon selection of the modify button 1330 with respect to a selected dose order 1320. The dose modification screen 1348 may include the dose order record listing 1350 and a dose modification field 1352. The dose modification field 1352 may include one or more fields that allow for modification of one or more dose order record data fields associated with the selected dose order 1320. For example, the dose priority, dose location, administration time of the dose, nursing unit to which the patient for the dose belongs, or other parameters may be modified for the selected dose order record 1320. The dose modification field 1352 may also provide a field to accept a reason for the modification of the selected dose order record 1320. Providing a reason for modification of the dose may be required field that must be selected by user prior to allowing the dose order record to be modified. The reason may be selected from a drop-down field that may include a plurality of predefined reasons that may be selectable by a user. Additionally or alternatively, the user may enter a reason for the modification using free-form text entry in the other reason box. Furthermore, depending upon the authorization level of the user, the other reason provided by the user may be included for later selection and the reason drop-down list.

Figure 10:
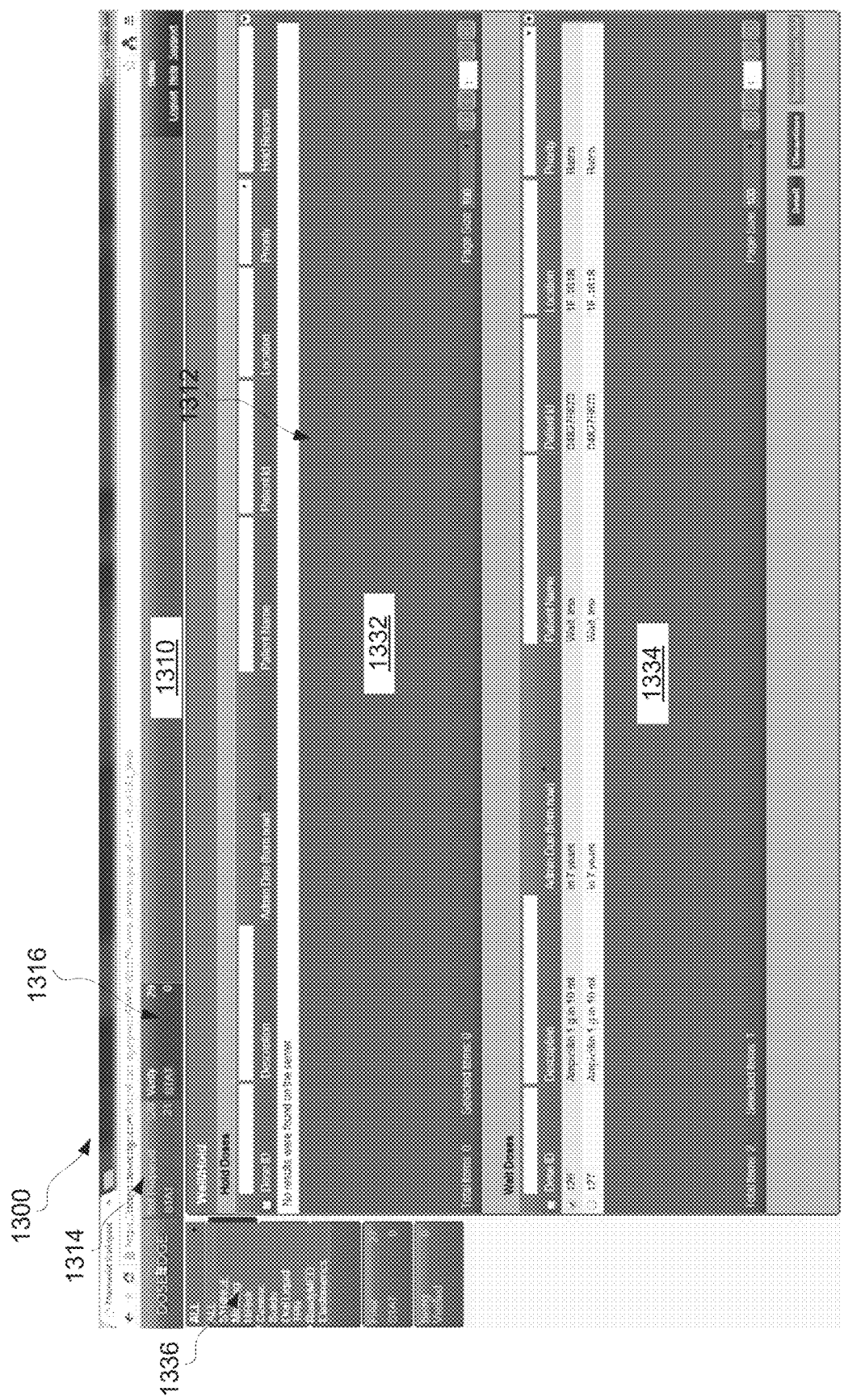

With further reference to FIG. 10, the dose order management screen 1310 is shown when the verify tab 1316 is selected. Upon selection of the verify 1316, doses that have been prepared and are waiting pharmacist verification may be displayed. Additional aspects related to pharmacist verification are described in greater detail below. Furthermore, FIG. 10 depicts the dose order management screen 1310 upon selection of a wait/hold secondary filter from the secondary filter list 1318. In this regard, the dose order record listing 1312 may be divided based upon a dose order record status of having a hold or wait status. Also shown in FIG. 10, a plurality of queue filters 1336 may also be provided. The queue filters 1336 may be configurable by a user and may allow for customization of filters to be provided. In this regard, the queue filters 1336 may include customizable parameter selection such that a filtered dose order record listing 1312 may be based upon any desired metadata for one or more dose order record data fields associated with the dose order records. That is, the queue filters 1336 may query any one or more of the dose order record data fields associated with each of the dose order records in return only those dose order records that match a query.

Figure 11:
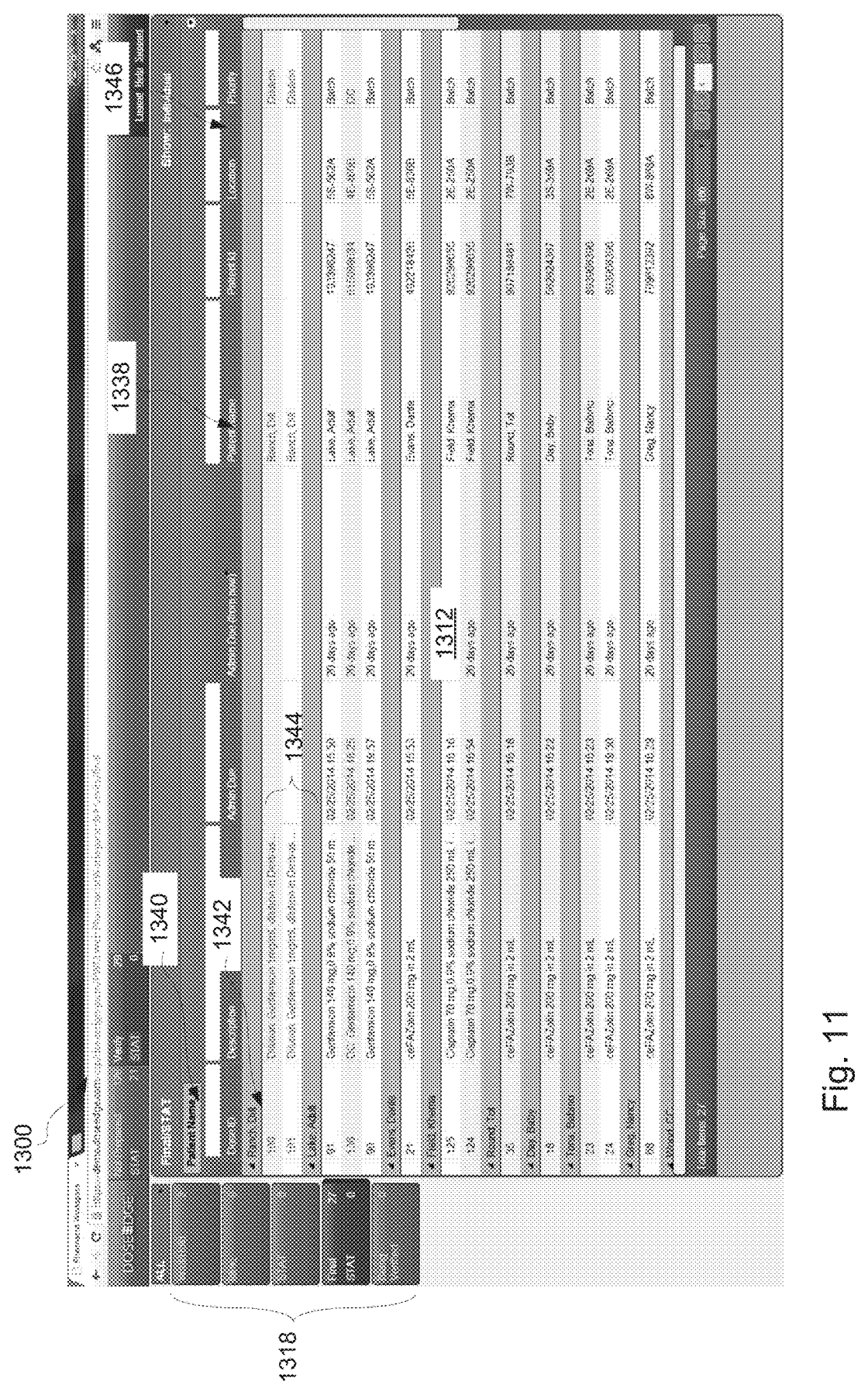

With further reference to FIG. 11, a further embodiment of the dose management screen 1310 is depicted. As shown in FIG. 11, the dose order record listing 1312 may be configurable to depict categorization of dose order records within the dose order record listing 1312. For example, user interface elements may allow for a column heading such as, for example, the patient name 1338 as shown in FIG. 11 to be dragged and dropped to a categorization bar 1340. Upon selection of the column heading 1338 for use in the categorization bar 1340, the corresponding column heading 1338 may appear in the categorization bar 1340. In turn, the dose order record listing 1312 may be configured to display dose order records according to category selected based upon the column heading 1338 selected. For example, shown in FIG. 11, the patient name column heading 1338 has been selected for use in the categorization bar 1340. In turn, the dose order record listing 1312 may be categorized according to patient name. Thus, the dose order record listing 1312 may include category headings 1342 within the dose order record listing 1312 such that associated dose order records 1344 corresponding to the category heading 1342 are presented. As may be appreciated, each category heading 1342 may be expanded or collapsed such that the associated dose order records 1344 for each category heading 1342 may be shown or hidden. It may be further appreciated the multiple category headings 1338 may be dragged and dropped to the categorization bar 1340. As such, the categorization within the dose order record listing 1312 may include a hierarchical listing such that a plurality of hierarchically displayed category headings 1342 may be provided in the dose order record listing 1312.

FIG. 11 also displays a column layout selection 1346 that allows for different column headings 1338 to be shown and/or hidden in the dose order record listing 1312. The column layout selection 1346 also allows for arrangement of the various column headings 1338. In this regard, the column layout selection 1346 may allow for user customization. In turn, the user may arrange the dose order record listing 1312 as desired including selection and/or arrangement of various column heads, categorization and/or filter results. In turn, once users authorized in the login screen 1302, the last used dose order record listing 1312 configuration or a default dose order record listing 1312 configuration any presented to the user.

Rules may also be used to otherwise assist in management of the dose order records in the dose order queue. For example, the local server 330 may also include or be in operative communication with a dose logic engine ("DLE").

The DLE may be operative to evaluate dose order records based on one or more portions of dose metadata stored in corresponding dose order record data fields. In this regard, anyone or more the portions of dose order metadata as described above may be utilized in a rule implemented by the DLE. Furthermore, conditions for execution of rules executed by the DLE may be established such that the rule may be performed at one or more times on dose order records. For example, one or more rules may be executed on a dose order record by the DLE when the dose order record is initially populated in the dose order queue and/or upon a subsequent condition being satisfied such as a change in status of the dose order record or the like. In any regard, a rule executed by the DLE may include scrutinizing one or more portions of dose metadata in view of a rule. For example, Boolean searching or the like may be utilized to identify whether a rule is to be applied to the dose order record based on the occurrence of a selected parameter in the dose order metadata. Upon determining that a rule applies to a dose order record, an operation may be associated with the rule that is in turn executed on dose order records determined to be applicable to the rule. The operation may be utilized to manage and/or modify the dose order record identified by the rule. For example, the operations may include changing a status of the dose order, modifying metadata of the dose order, or other appropriate operation with respect order record or metadata associated with the dose order record. Two such examples of operations that may perform by the DLE include identifying duplicate orders and/or discontinued orders.

In a duplicate order detection rule, the DLE may be operative to review a first dose order record in view of other dose order records within the dose order queue to determine if the first dose order record corresponds to a potential duplicate dose order. In this regard, the DLE may evaluate the metadata regarding the first dose order record to determine if other ones of the dose order records within the dose order queue match the identified metadata regarding the dose order to a predetermined correspondence. The predetermined correspondence may be selectable by a user of the management tool 1300. It may be appreciated that the matching of the metadata between the dose order record being reviewed in the other dose order records in the queue may not necessarily need to be identical. For example, the rule may be written such that if selected ones of the metadata fields are identical between the first dose order record being reviewed and the other dose order records in the dose order queue, the dose order record being reviewed may be flagged is a potential duplicate order. Such a rule may be applied to the first dose order record when the record is initially populated the dose order queue.

Figure 12:
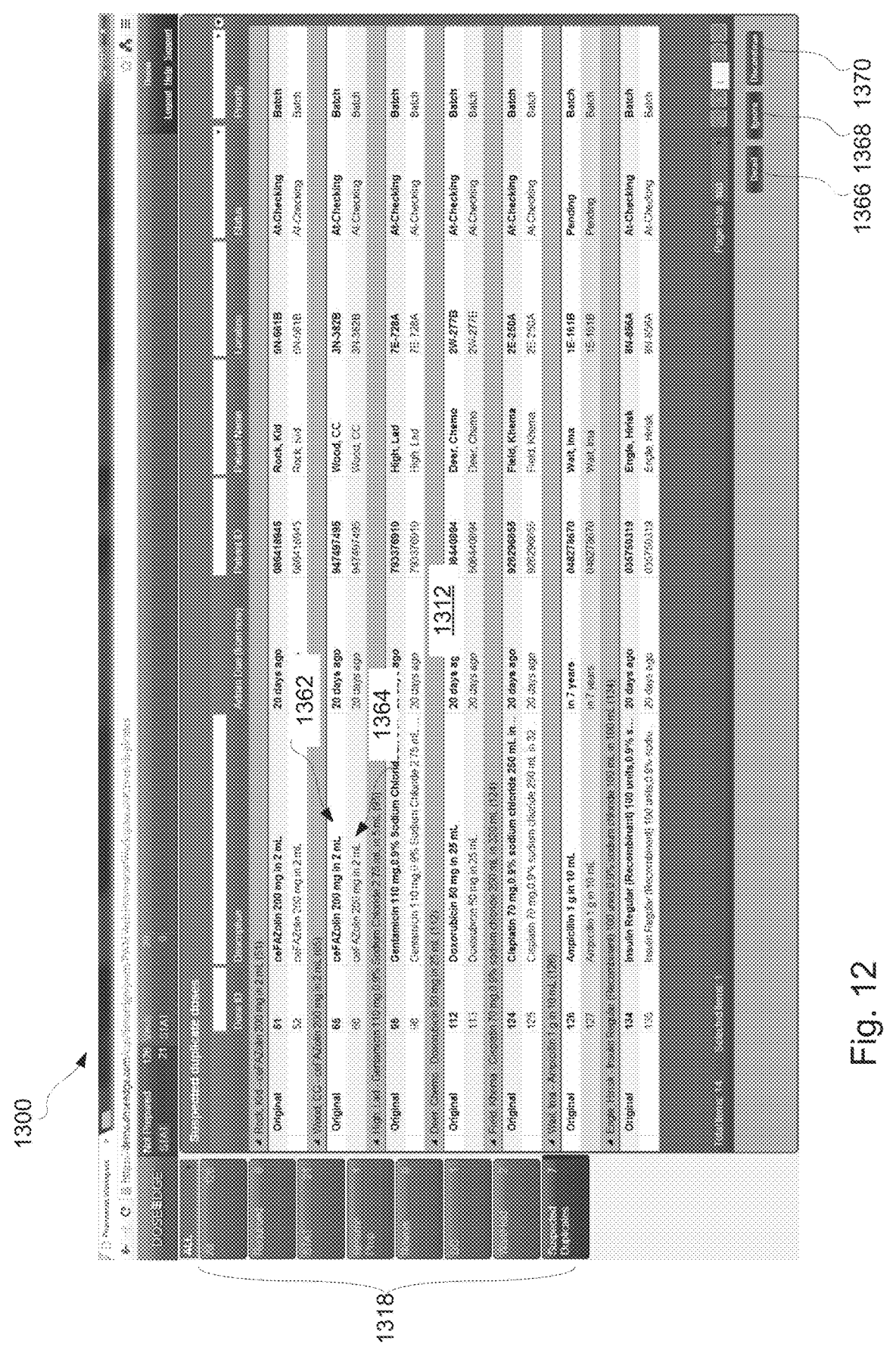

In this regard, with further reference to FIG. 12, may be appreciated that the dose order records that have been identified as a potential duplicate order may be sorted and presented to a user. In this regard, the dose order management screen 1310 may include a secondary filter for presenting suspect duplicates in the dose order record listing 1312. In this regard, the dose order record listing 1312 may be populated with suspected duplicates. In this regard, the dose order record listing 1312 may present a user in an original dose order record 1362 that is associated with one or more suspected duplicates 1364 based on exceeding a predetermined correspondence between the metadata of the suspected duplicates 1364 the original dose order record 1362.

Accordingly, upon selection of the suspected duplicate 1364, number of operation buttons may be enabled. For example, the user may select detail button 1366 to be presented with additional details regarding the suspected duplicate order 1364 and/or the original order 1362. In turn, the user may determine suspected duplicate 1364 may not in fact be a duplicate order, but rather be a valid order the should proceed preparation. In this regard, the user may select the ignore button 1368 to indicate that the suspected duplicate 1364 is not in fact a duplicate of the original order 1362. In contrast, should the user determine that the duplicate order 1364 is in fact duplicate of the original order 1362, the user may select the discontinue button 1370 to discontinue the duplicate order 1364 such that the duplicate order may be removed from the dose order queue. Upon selection of either the discontinue button 1370 or the ignore button 1368, the user may be present the dialog box that may require the user to identify the reason for the discontinuation or ignoring of the suspected duplicate status of the dose order.

Additionally, it may be recognized that the DLE may process incoming dose orders to determine if the order corresponds to a discontinuation of an order. That is, a common practice when processing dose orders is to indicate a discontinuation of a first order by subsequently sending a corresponding order to the first order at a later time with a discontinue status for the subsequently provided order. In prior approaches, the receipt of such a discontinued order may simply result in printing a label with the dose order details and a discontinuation status. This would in turn require a user to go through the printed dose order labels to locate the original dose order that was referenced in the discontinued dose order in order to replace the original dose order on a discontinued status. The DLE may be utilized to automate this process in the context of the dose order queue stored by the local server 330 by identifying receipt of a dose order in the dose order queue that contains a discontinued status and automatically matching the discontinued dose to one or more existing dose order records. Thus, receipt of a dose order with a discontinued status may trigger the DLE to perform a query of the dose order queue to identify corresponding ones of the dose orders in the dose order queue that exceed a predetermined correspondence to the discontinued dose order. For example, one or more overlapping or identical pieces of metadata between the discontinue dose order and the identified discontinued order in the dose order queue may be determined. The predetermined correspondence may be customizable by a user. In any regard, upon identification of a dose order record from the dose order queue that corresponds to a received discontinued dose order, the original dose order may automatically change the status of the one or more identified dose order records to a discontinued status.

The execution of a discontinued dose rule by the DLE may also at least partially be based upon the status of the one or more dose order records from the dose order queue that are identified as discontinued doses at the time the dose order records are identified. For example, in one example, the dose order for the dose order record identified as a discontinued dose may not yet have been prepared. In this regard, the DLE may simply change the status the dose order record to discontinued and remove the dose order record from the dose order queue such that the discontinued dose order record is not prepared. In contrast, the identified discontinued dose order record may have been prepared and verified and be in sort awaiting dispatch from the pharmacy. In this regard, the status of the dose order may be modified to discontinued and any resulting dose that was prepared for the dose order record may be changed from a dose to a product. That is, the dose order system may print a work in progress label or other identifier that allows the prepared dose to be moved to pharmacy stock for later use (e.g., to fulfill a later dose order received at the pharmacy). The modification of a dose to a produce may also occur in the case where a dose has been prepared and not yet verified. In this regard, the pharmacist that performs the verification may be presented with the status of the dose being discontinued.

In addition to the dose order record management functions related to the dose order records described above, the pharmacy workflow management application 114 may further be operative to provide dose order records to a workstation for the purpose of fulfilling or preparing the dose order record at the workstation. Any number of different workstations can be part of the system. For example, FIG. 2 shows a flowhood workstation A 500, a flowhood workstation B 510, and a chemo workstation 520. However, other workstations may be provided without limitation. For instance, those skilled in the art will recognize a number of different workstations that are often utilized in the pharmacy environment. Such workstations may include, laminar flow hoods, biohazard cabinets, or other particularized workstations used in the preparation of specific doses. However, other workstations may also be included that do not actually prepare doses, but may be used for pharmacy management such as supervisory terminals (e.g. that perform web-based system management, query reporting, etc.), situation boards that display system status or the like, pharmacist review stations, or other appropriate workstations in operative communication with the local server 330 to communicate dose order record and associated metadata.

In any regard, the local server 330 may be operative to communicate with a workstation to provide information related to the dose order record thereto. For example, in order to prepare a medication dose at one of the workstations, data regarding a corresponding medication dose order record may be sent by the local server 330 to the appropriate workstation. As may be appreciated, the various workstations may be particularly suited for particular type of medication dose to be prepared. For instance, a dose of chemotherapy to be administered to a patient may be provided to the chemo workstation 520, whereas another type of dose may be prepared at another workstation within the local system 110.

With returned reference to FIG. 4, information related to dose order records may be forwarded to client applications executing on one or more workstations located within the pharmacy, hospital, or elsewhere. The workstation client application or technician can manage the various open tasks (e.g., orders to fill) by interacting with the workstation in order to follow a protocol or "recipe" mandated for a particular dose order or batch of orders, as indicated a block 440. The dose orders are prepared as doses at the workstation with the benefit of documentation support as indicated a block 430. The documentation support is provided to the technician to guide preparation and better ensure the doses are prepared in accordance with established protocols and policies. As described further below, the intermediate steps in the preparation of each dose order are subject to data capture to permit post preparation review of the steps taken to prepare each dose.

Figure 13:
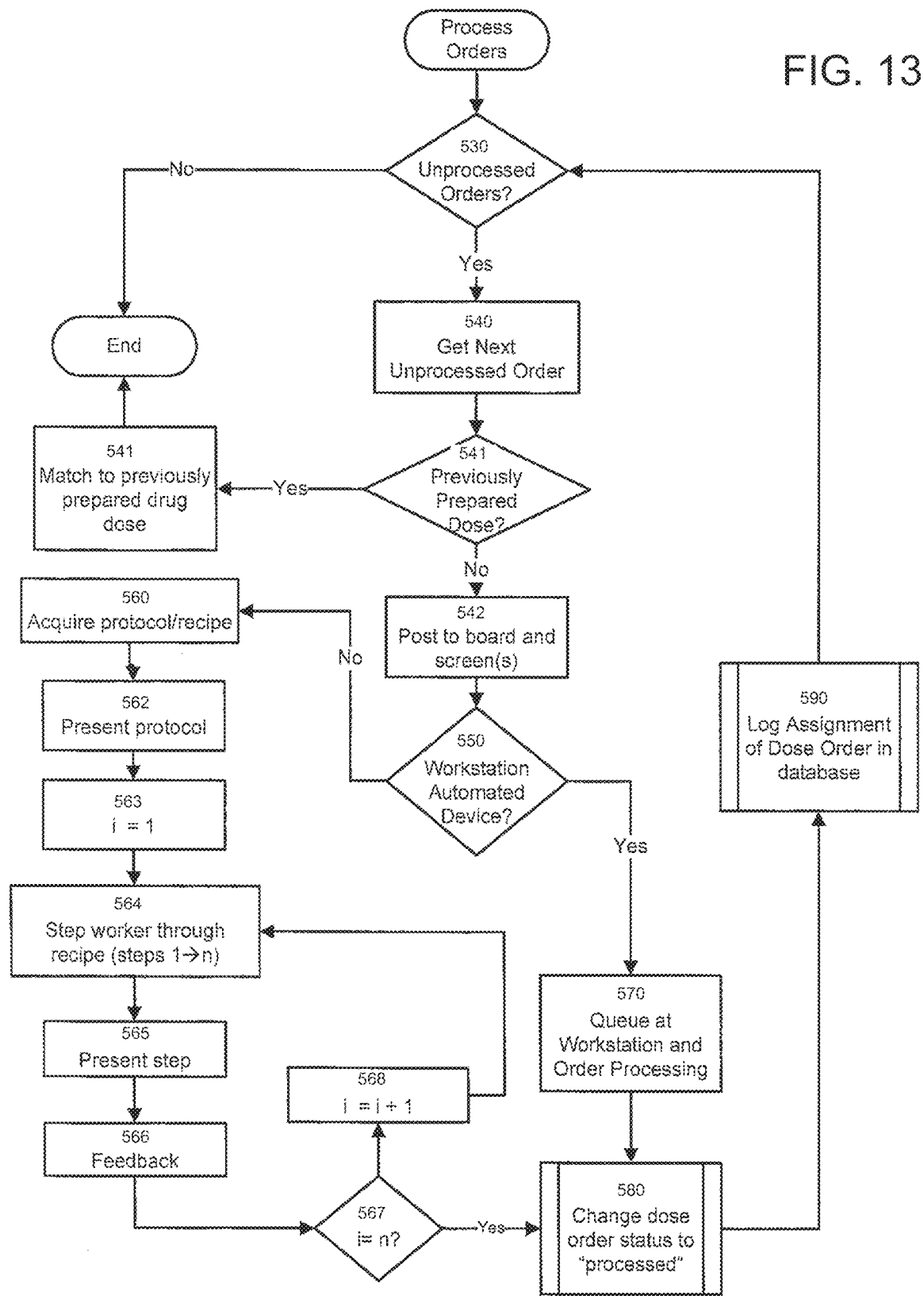
FIG. 13 depicts a flow chart of an embodiment of a method for processing dose order records to prepare a corresponding dose at a work station.

Returning to the dose preparation workflow and documentation support 430 and management of scheduled tasks by the workstation 440 depicted in FIG. 4, an exemplary method performed in relation to these schematically depicted tasks as shown in FIG. 13. The order filling processing commences at step 530 at which it is determined whether there anyone to fill dose order records in the database.

If unfulfilled dose order records are in the database, unfulfilled dose order records are retrieved at step 540. At decision 541, it may be determined whether a dose previously prepared and stored which would satisfy the dose order. For disclosure of assist in the prepared dose orders in anticipation of need for such orders, see U.S. application Ser. No. 11/844,135, filed Aug. 23, 2007, entitled "Automated Centralized Preparation of Medications in Anticipation of Use," which is co-owned with the present application and hereby incorporated by reference in its entirety. If no such dose exists, the dose order may be posted to the dose order queue at each workstation and may also be posted to the situation board 400 at step 542. Additionally, the dose order record may be updated so that a status of the dose order records indicated as "pending" to signify the dose order is ready to be prepared. Optionally, the requirements for filling the dose order are retrieved and used to post the dose order to the dose order queues only those workstations that are suitable for handling such dose order. In this way, individual workstations may have a tailored queue of pending dose orders. In another arrangement, such tailored queues are provided to the individual workstations with the operator such workstation can expand the presentation to see other disorders in the queue even if not suitable for handling of the operators given workstation.

With returned reference to FIG. 13, at step 542, the drug order queue is generated and optionally one or more dose orders can be assigned to a particular workstation based on one or more rules that govern the distribution of dose orders to a particular workstation. The system may be configured so that the dose orders must be "pulled" from the dose order queue. In other words, an affirmative step may be required for the dose order to be assigned to particular workstation. For example, as discussed above, an operator at a given workstation may review the dose order queue and then select the dose orders that will be fulfilled at the given workstation (e.g., by using a touch screen display), at which time these orders are effectively assigned to workstation and are removed from the dose order queue.

In some instances the workstation is in the form of an automated device and therefore, the automated device has a selection module comprising code to automatically select those dose orders in the queue that can be fulfilled by the workstation. The selection can take into account number of different rules including the number of pending dose orders at this workstation, the availability of different drugs, etc. The automated device communicates with the local server 330 and selects and pulls dose order for filling.

However, even when the system is configured to operate in such a pull mode, the individual dose orders can be preassigned in the event that a dose order can only be fulfilled by a specific workstation, in which case the application 114 may recognize this fact and identifies that the particular dose order is intended for delivery to a particular workstation. For example, if the dose order that is received and processed step 541 is the type that can only be fulfilled by specific workstation (e.g., chemotherapy workstation), the dose order will be identified as such on the dose order queue in the workstation type is qualified for receiving and fulfilling the dose order can be notified (e.g., the chemo workstation 520 as shown in FIG. 2). Similarly, the type of dose order can be identified as a manual fill dose order on the situation board in one or more manual workstations can be alerted or to simply include the dose order on screen.

In another application, the system may be configured to "push" dose orders to the individual workstations. In this regard, the local server 330 may select which workstation is best capable of handling incoming dose order and assign the dose order to that workstation. Workstation may then be sent to the workstation fulfillment of the order. In this regard, the "pushing" dose orders to the individual workstations may be based on a multitude of factors including, for example, the type of workstation, the backlog of dose orders, the types of drugs located at a given workstation, the technician logged in at a given workstation, or other factors.

Furthermore, the application 114 can analyze the supplies necessary to fulfill the order. The list of required supplies may be compared to an inventory of supplies and their availability, optionally broken down by hospital, pharmacy location, or workstation. If there are insufficient supplies, additional supplies may be automatically order the relocation of supplies from one workstation to another may be ordered such that at least one workstation will have the necessary supplies to fulfill the dose order.

In an embodiment, a rule-based management of dose orders (e.g., by way of the DLE discussed above) may facilitate automatically assigning a dose order based on the preparation mode for the dose order. For example, the dose order may be evaluated with respect to at least one portion of dose order metadata stored in a dose order record data field associated with the dose order record. This evaluation may be performed upon population of the dose orders to the dose order queue. In turn, the evaluation may result in the preparation mode being assigned to an order. In turn, the user may be free of selecting the preparation mode associate of the dose order record, rather the preparation mode may be assigned automatically in response to the evaluation of the at least one portion of dose order metadata stored in the dose order record data field. The preparation mode assigned the dose order may be used, for example, to generate and/or select an appropriate preparation procedure for that dose order. Such preparation procedure may in turn be presented to a user when preparing the dose. As the preparation mode may be automatically attributed to the dose order based on application of a rule to the dose order, the user may not be required to select the preparation mode for the dose order. In turn, the dose order may be routed to an appropriate workstation where the user may be presented with the preparation procedure at least partially based on the automatically assigned preparation mode that is been associated with the dose order record by the system. Furthermore, dose orders that have the same preparation mode may also be grouped together into a micro batch in a queue view list.

In this regard, the pharmacy workflow management application 114 may allow for a dose order record to be communicated to a workstation for preparing a dose associated with the dose order record. As may be appreciated, the protocol or "recipe" corresponding to the dose order record may be provided to a technician at the workstation for use in preparing the dose. During the preparation of the dose, the technician may scan, enter, capture, or otherwise generate or record dose order metadata corresponding to the dose order being prepared. At least a portion of this information collected by the technician during preparation of the dose may be utilized to allow for a pharmacist review of the preparation of the dose as described in greater below.

With returned reference to FIG. 13, if the dose-order is one determined to be suited for manual preparation, then the process flow branches to block 560. At block 560, protocol information is retrieved. This is because, before the dose order record is dispatched to a manual workstation for action by the operator, additional information is provided to facilitate the manual fulfillment of the dose order at the selected workstation. This can be based on the determination that manual preparation is required and the assumption that providing additional information can improve safety, efficiency, and precision during fulfillment of the dose order. The management module can associate the additional information with the dose order record. For example, at step 560 the medication and form of dose (e.g., syringe, IV, oral dose etc.) specified by the dose order record can be examined so as to determine the protocol by which the dose of that medication should be prepared. The protocol can specify the steps (e.g., sanitization and documentation) that must be taken during preparation to comply with Food and Drug Administration regulations or any other governing procedures regarding the conduct of the pharmacy. Furthermore, the protocol associated with the dose order at steps 560 and 562, preferably is interactive in guiding the operator through the fulfillment process to achieve the same level of accuracy and dose safety which is typically associated with the automation. For example, the protocol can require the operator's input including logging of events at critical stages of the dose preparation process (e.g., requiring the operator to scan information related to the source drug containers).

The additional information (i.e., protocol) can be associated with the dose order record at step 562 for presentation to the operator. The association can be accomplished by attaching the protocol file to the dose order record, or otherwise communicating it electronically to the workstation selected for handling that dose order, or by printing a copy of the protocol to include with a printed order for the dose. In a paperless environment, the protocol is preferably displayed along with the display of the order or can appear as a hyperlink or call-up dialog box from within the order display at the workstation.

Figure 14:
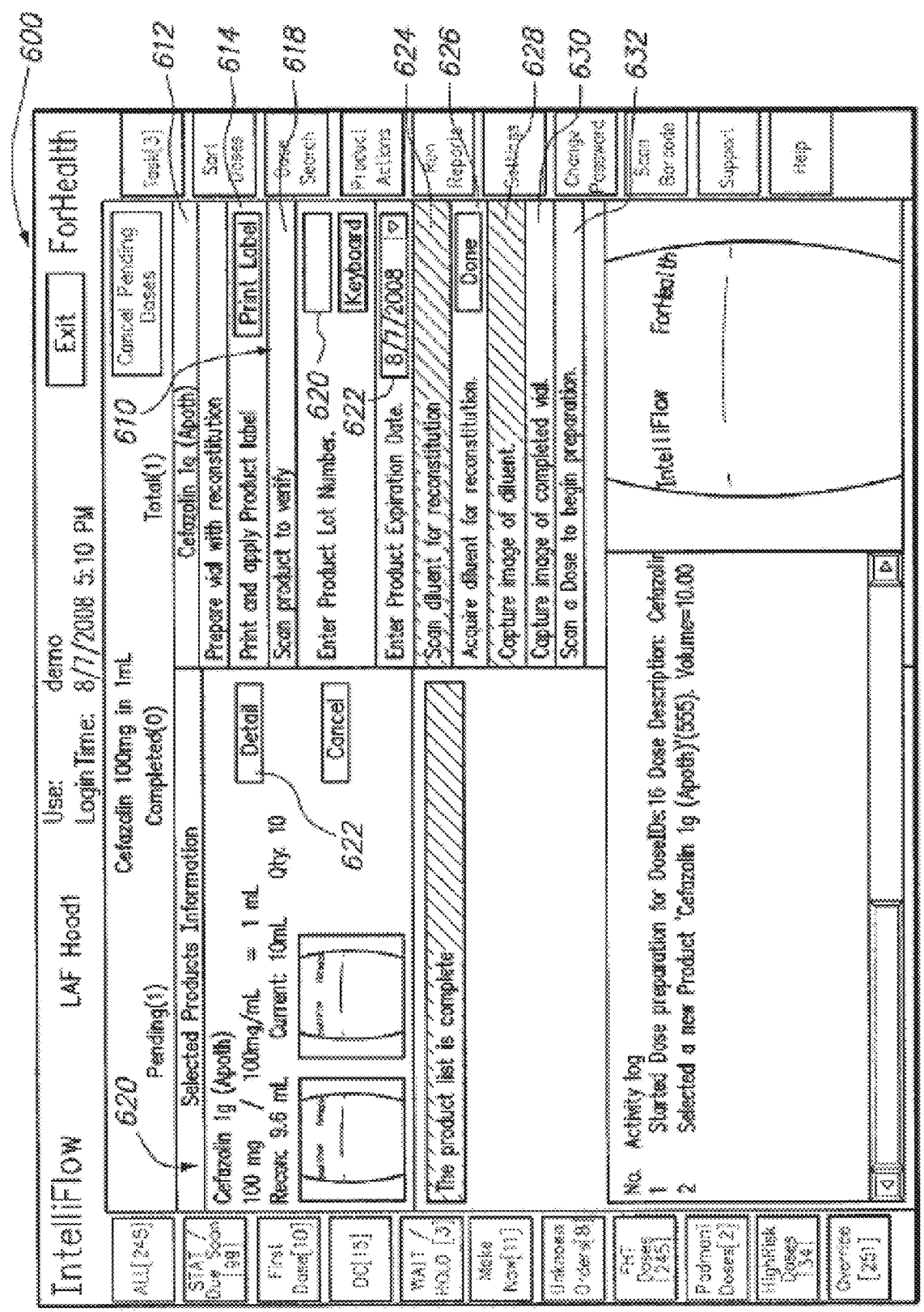
FIGS. 14-15 depict an embodiment of a user interface of a pharmacy workflow management application presented to a user when preparing a dose corresponding to a dose order record.

Referring briefly to FIG. 14, one exemplary screen 600 is illustrated that lists a number of steps generally indicated at 610 that are required to be performed to successfully prepare a medication product that is used to prepare a dose that is part of a dose order. On the left side of the screen, the drug to be prepared is clearly identified at 620, in this case Cefazolin 1 g (Apoth). This screen is an interactive screen in that the user can simply highlight different areas either to receive more information or to enter information. For example, there is a Detail button 622 near the drug identification and if additional information is needed concerning this particular drug order, the user can simply highlight this particular button (as by "clicking" the box).

On the right side of the screen are processing steps 610 that must be undertaken in order to prepare the requested dose. For example, a banner 612 indicates again the drug being produced is Cefazolin 1 g (Apoth) and below this banner there are a number of steps 610 that must be performed in order to produce the correct dose (drug product). The illustrated screen shows a first step 614 of printing and applying a product label. The label is printed by simply pressing the button 616 that is labeled "Print Label". As soon as the label is printed, the user is prompted to move on to the next step 618 which is a step of scanning the product to verify that the proper product is present at the workstation. Conventionally scanning equipment can be used to scan (e.g., a barcode) the product and then the user is prompted to enter the Product Lot Number in a box 620 that is provided and the user then enters the Product Expiration Date in another box 622. All this inputted information is used to confirm that the correct product (drug) is present and is being used in the preparation of the Cefazolin 1 g dose. In this regard, it may be appreciated pharmacy workflow management application 114 may require a previous step to be completed prior to moving to a subsequent step. Performance of some steps may include positive capture of information related to the dose being prepared. In turn, the sequence of the protocol presented for a dose may be documented and explicit steps in relation thereto may be required prior to progressing in the sequence.

In another aspect of the present invention, other identifying information can be used to assist in determining that the correct drug is present at the workstation and is suitable for use in fulfilling a pending drug order. More specifically, the Drug Listing Act of 1972 requires registered drug establishments to provide the Food and Drug Administration (FDA) with a current list of all drugs manufactured, prepared, propagated, compounded, or processed by it for commercial distribution. The National Drug Code (NDC) is a universal product identifier used in the United States for drugs intended for human use. The FDA inputs the full NDC number and the information submitted as part of the listing process into a database known as the Drug Registration and Listing System (DRLS). The information submitted as part of the listing process, the NDC number, DRLS, and the NDC Directory are used in the implementation and enforcement of the Act. In turn, the NDC for a drug may be recorded during the preparation of a dose. A formulary of the pharmacy workflow management application 114 may be cross-referenced to determine if the NDC received during preparation corresponds to a drug appropriate for the dose being prepared. If the NDC is appropriate as determined by reference to the formulary, the user may be allowed to sequence to the next step in the process. If the NDC does not match, the operator may not be allowed to progress and the fact that in incorrect NDC was provided may be noted. It will also be appreciated that some of this information can be inputted using a reader devices, such as a barcode reader, etc.

Dose order records stored in the local database can be ordered or arranged and displayed in the dose order queue and/or at the situation board in accordance with a rule base that operates on the database with one or more rules. The rules may be at least partially based on dose order metadata populating one or more dose order record data fields. For example, one rule can be to optimize fulfillment of the orders. Thus, like dose orders (e.g., dose orders with similar drug components as reflected in the dose order metadata) can be processed at the same workstation one after another and hence faster because there is less cross-contamination and medication changes (i.e., retrieval and storage). Thus, dose orders can be grouped by type or medication, such that dose records requiring the same medication or with no risk of cross-contamination can be processed in order by the same machine, or set of machines. In this regard, the rules are configured to sort the dose-orders by type or medication. Alternatively, dose order records can be prioritized by urgency (e.g., "First Doses" or "STAT"). For example, if a doctor urgently needs a specific medication, the data stream identifying the dose can include information indicating its urgency, and the dose order record can include such urgency information. Thus, the rule in this instance operates to re-sort an urgent order to near the front of the queue, or have that order identified (e.g., flagged) as urgent for immediate or expedited fulfillment. Through this or a similar mechanism, the next unfulfilled dose order retrieved at step 140 can be arranged in the queue to optimize throughput or to satisfy other rule-based priorities. Alternatively and as described above, urgent orders can simply be highlighted and/or labeled as such in the drug order queue presented at the workstation.

The workstation can include various tools and monitoring equipment to assist and perform quality control during the manual preparation of the dose order. Such tools and monitoring equipment can include barcode scanners, digital cameras, scales, hydrometers, spectrometers, and other tools that can be used to verify the properties of a substance. For example, a computer monitor at the workstation can prompt the operator to take certain measurements of the dose order being prepared and input the results of those measurements. Failure to input a measurement within an acceptable range can result in the system automatically rejecting the preparation. Furthermore, to prevent operator fraud, the system can prompt the operator to place the preparation on a scale, or within another instrument, that automates the measurement, thereby reducing the opportunity for the operator to intentionally or unintentionally deceive the system. In this regard, it should be appreciated that the protocol presented to the used at block 562 is preferably coded to capture the progress made toward dose fulfillment. Thus, steps taken in completing the protocol or recipe are preferably coupled with specific operator input such as photographing a drug vial, weighing a syringe, and the like, with the inputs being captured and included in a data record that can be forwarded to the pharmacist for review and approval. The data record can be a record storable in the Ensemble database that is used in a preferred embodiment of the invention.

In accordance with the present invention and as previously mentioned, the present system includes means, such as readers and the like, which allow a particular drug to be identified at step 618 and compared to a database to ensure that the identified drug is the drug which is being requested is the same drug which has been identified at a particular location (station) of the present system. Since the NDC includes product code information, such as the specific strength, dosage form and formulation, it can be used in drug identification step 618 of the present system. It will also be appreciated that the NDC number can provide a means for redundantly confirming the identification of the drug being used at the workstation to prepare the requested drug order. In other words, other identifying information that is printed or otherwise present on the drug product can be read and then the NDC number can be read and the two compared as part of an integrity check to ensure that the correct drug product is present at the workstation.

The next step 624 involves scanning the diluent that is used in the reconstitution process. Once again, conventional scanning or imaging techniques can be used to identify and confirm whether the correct diluent is being used in the reconstitution process. The step 626 involves acquiring the diluent for the reconstitution and then confirming its proper identity and the user can indicate that the step has been completed by pressing the button labeled "Done". The next step 628 can involve capturing the image of the diluent using conventionally techniques (e.g., a camera) and additional steps that can be performed are capturing the image of the completed vial 630 and scanning a dose to begin preparation of the individual dose 632. All of the information that is gathered in each of the steps is stored in the local database, preferably in the same record as or in association with the particular drug order being filled.

At any point, if a task performed in one of the steps is not verified as being correct, the operator is prevented from going onto the next step and the dose is not prepared.

Figure 15:
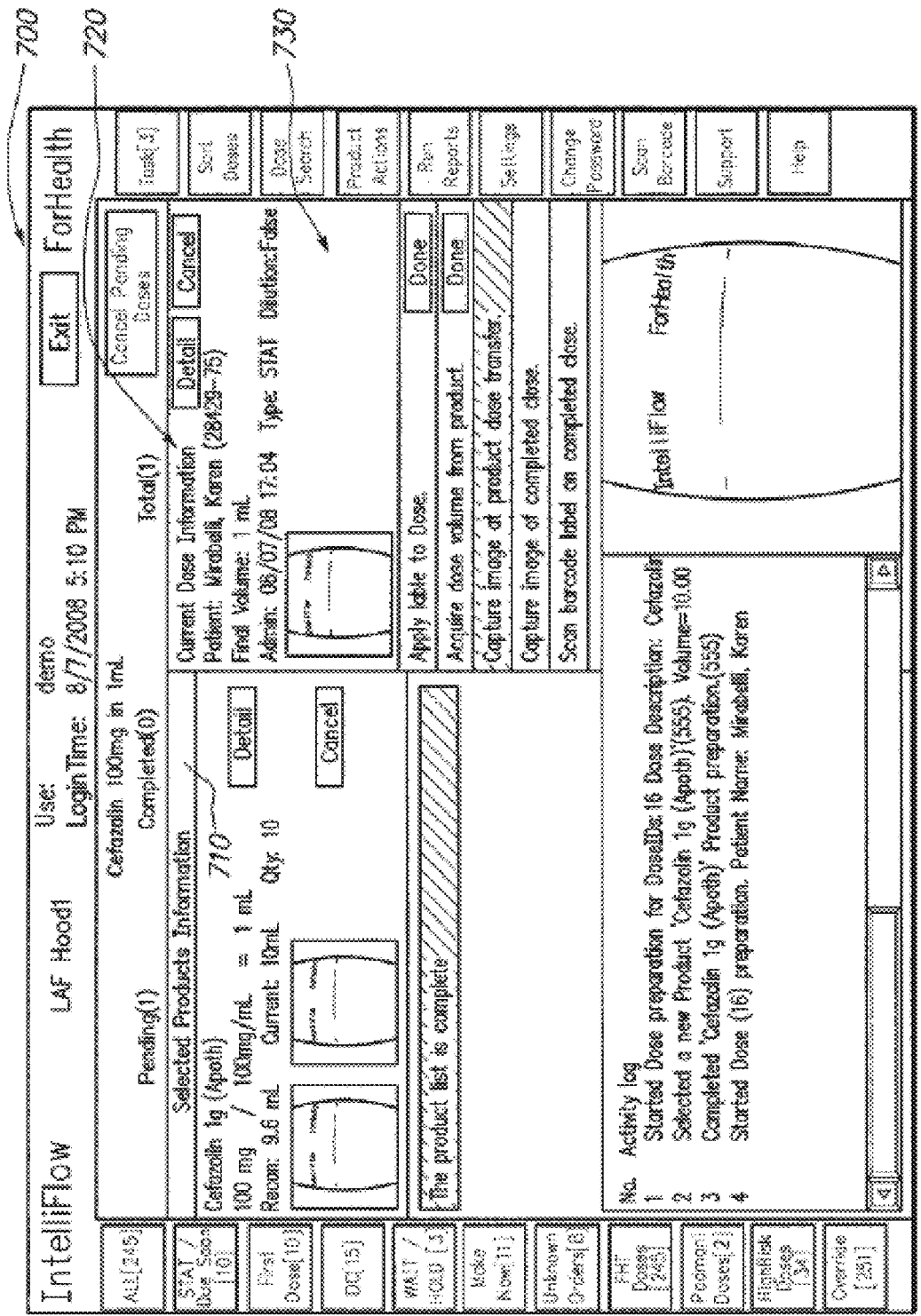

Also, with brief reference to FIG. 15, a sample screen 700 shows exemplary steps that are displayed to the operator to assist the operator in preparing a specific dose of medication. On the left side of the screen, a "Selected Products Information" section 710 is provided and lists the drug product that is being prepared. In this example, the drug product is Cefazolin 1 g (Apoth). On the right side of the screen is information 720 that relates to the current dose that is being prepared for a specific patient. For example, the patient's name (e.g., Karen Mirabelli) is clearly identified along with any identifying patient information (a patient number). The dose information also includes a final volume of the dose (e.g., 1 ml) and administration information is provided, such as a date and time (e.g., 8/7/08 17:04) when the dose is to be administered. The type of dose (e.g., STAT) can also be listed to alert the operator to any special processing information (e.g., the dose should be processed in an urgent manner).

The screen of FIG. 15 lists a number of steps 730 that are to be performed by the user to prepare the dose and fulfill the dose order. For example, one step may be the step of applying a label to the dose and once this task is performed, the user can indicate so by pressing a button that is labeled "Done". Another step can be to acquire the dose volume from the product and once this task is performed, the user can indicate so by pressing a button that is labeled "Done". Other steps that are to be performed and verified are capturing the image of the product dose transfer; capturing the image of the completed dose; and scanning the barcode label on the completed dose. Each of these steps must be verified as being properly completed before the user can continue with the other steps of the dose preparation process.

The NDC information also contains formulary information and this can be used at the workstation as the drug is being prepared in accordance with the steps shown and described with reference to FIG. 15. In particular, this information can be used as part of an integrity check (drug verification process) to ensure that the drug is being prepared properly.

As mentioned above, if it is determined at step 550 that the dose order record is suitable for automated handling, it will be queued at an appropriate automated workstation. Queuing the dose order record at a workstation presents a further opportunity to optimize the distribution of orders within the pharmacy. For example, it may not be feasible to determine at step 140 an optimal organization of dose order records to ensure that dose order records requiring similar medications are queued at the same workstation. Thus, at step 570, a particular dose order can be queued at an automated workstation that is known to be processing the same medication, or to any workstation at which a dose order involving the same medication was just queued (e.g., a workstation to which the dose order and protocol are provided at block 560. Re-ordering and queuing of dose orders can be very flexible if the urgency of the dose order is very low. For example, the dose orders can be queued in a less than optimal order with respect to time, but more efficient with respect to medication changes and cleanings to prevent cross-contamination. Optionally, the current workload and/or work distribution of dose orders to workstations can be tracked or monitored and presented to a user (e.g., presented on a centralized display) for management and performance monitoring.

Once the workstation fulfills the dose order, the status of the dose order record can be changed to indicate that it has been processed at step 580. The status change can be received by the pharmacy workflow management application 114 as an acknowledgement that the drug dosage form has been prepared, or as a "processed-order" status, and this can further result in an update to the dose order record, the inventory record, or both concerning any drug dosage forms that have been prepared but not yet delivered. Additionally, data concerning the assignment of the dose order to the selected workstation and the completion of the dose order can be logged in the database. Logging information concerning which workstation processed the dose order into the database (e.g., the local database 330), as indicated at step 590, enables complete tracking of both the dose-order processing steps and tracking of the prepared dose itself from its entry as data into the pharmacy system to its delivery to the patient. Accordingly, at step 590, the information can be logged into the local database 112.

The present system therefore provides a composite workflow application that can layer on top of a hospital's existing pharmacy information system 320, without requiring any changes to that system, in order to manage the production of IV doses (and other doses) in the pharmacy, track dose delivery from the pharmacy, prevent medication errors caused by incorrect dose preparation, capture detailed history of dose preparation (including images), and serve as a gateway to automation systems throughout the pharmacy, such as carousels, compounders, and IV robots.

Accordingly, the pharmacy workflow management application 114 may allow for a pharmacist review of a dose prior to the dose being distributed from the pharmacy is depicted in the pharmacy dose verification and approval step 450 of FIG. 4. In traditional approaches to pharmacist review, a pharmacist would often have to enter the pharmacy to verify work performed by a pharmacy technician. Oftentimes, such preparation environments comprise clean rooms such that the pharmacist might have to go through an extensive gowning process in order to access the area in which the dose is being prepared. In contrast, given the centralized storage of dose order metadata facilitated by the pharmacy workflow management application 114, a pharmacist may utilize a remote access terminal 314 or a client at the local system 110 that is external to the pharmacy, but still within the local system 110 to access, review, and approve or deny doses prepared by technicians.

Accordingly, the pharmacy workflow management application 114 may provide for remote inspection of prepared doses, thus facilitating the practice of telepharmacy, by which a pharmacist can inspect the dose preparation from any location inside the hospital or elsewhere so the dose is released more quickly and efficiently from the pharmacy. Accordingly, dose inspection/verification may be performed by a pharmacist from any location using the portal the present invention. Dose order record metadata stored at the local server 330 may be presented to the pharmacist for inspection and approval. The portal may be provided through a conventional web browser, optionally with the use of a plug-in or other active code that provides for review of the data presented such as, for example, magnification, rotation, contrast adjustments, and other adjustments to an image to facilitate interview.

In turn, a pharmacist may be presented with images associated with the preparation of the dose. The pharmacist can not only look at images of the final product, including the product label, and other related product information, such as a barcode information, but also, the pharmacist can review information and images that obtain the particular steps in the overall drug preparation process. For example, during a drug reconstitution process, the operator may step through the drug preparation as described above such that the operator must confirm each step is successfully completed prior to moving to the next step. One of the steps in the preparation of the dose may be the selection of a particular drug vial. The selection of the drug while may be captured using the camera to produce an image that may be later viewed by the pharmacist. Additionally or alternatively, a scanning event during which the operator identifies the drug vial being used by scanning a barcode on the drug vial may also produce data that is reviewable by the pharmacist. The pharmacist can view each or many of the steps are taken in order to confirm that steps properly completed in the protocol to prepare the preparation and thus, confirmed the dose is properly prepared. The remote verification facilitated by the pharmacy workflow management application 114 provides a superior and more complete way of inspecting and verifying a dose prior to releasing the dose to the patient because the pharmacist may be able to visually inspect multiple images and/or data obtained during the steps of preparing of the drug to confirm that the steps are carried out properly, and thus, ultimately conclude whether the dose order is properly prepared and should be released the patient. In contrast, traditional approaches may rely upon a pharmacist discussing with the technician the steps taken to prepared dose without any way to actually verify the steps performed. This improved verification may be important in many circumstances, including when the constituent components of the final dose include more than one clear fluid such that a visual inspection of the final dose alone cannot provide a basis for the pharmacist to confirm the accuracy of the dose. Thus, benefit results from the capture and review steps, regardless of whether the pharmacist is on-site or remotely situated.

Figure 16:
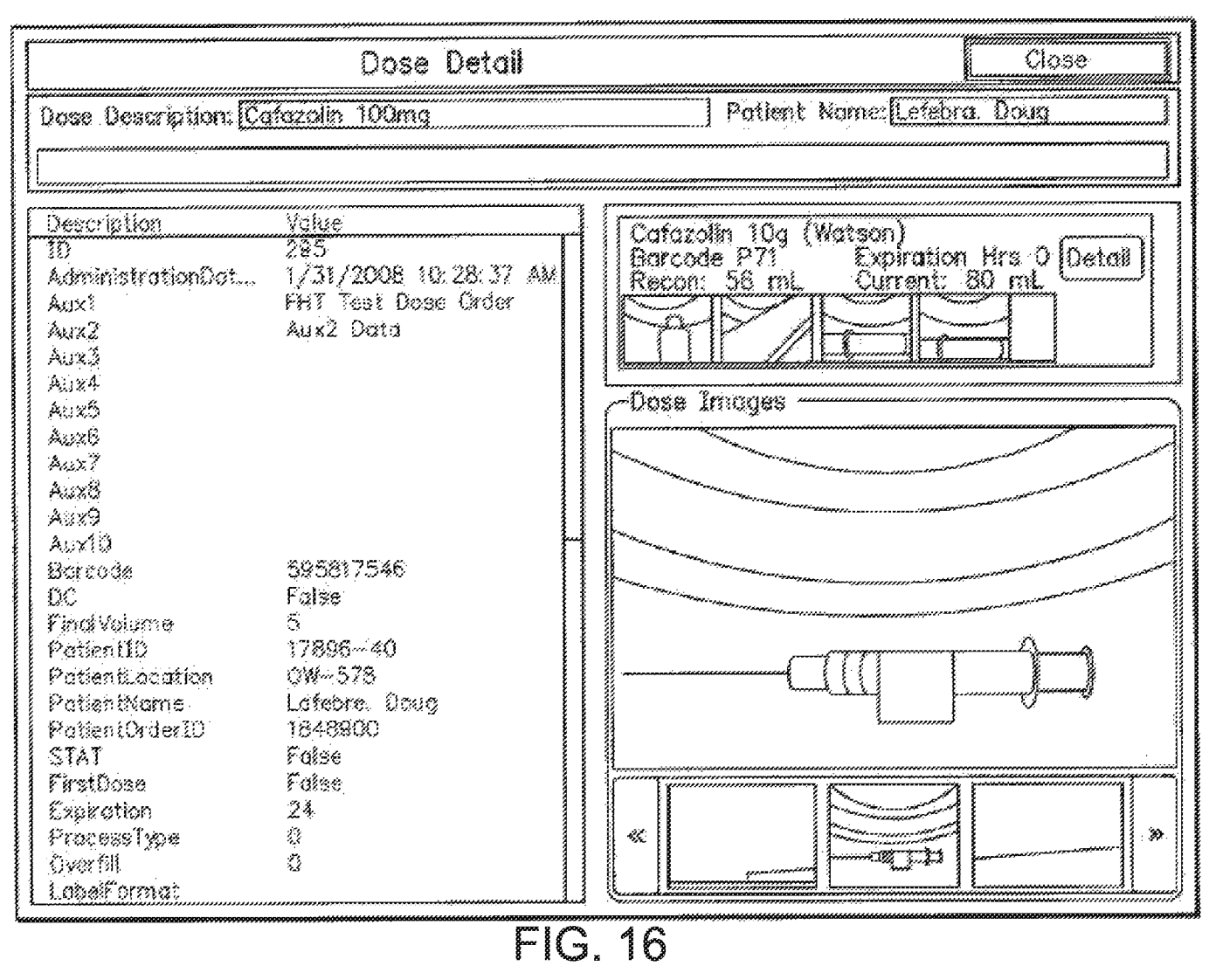
Figure 17:
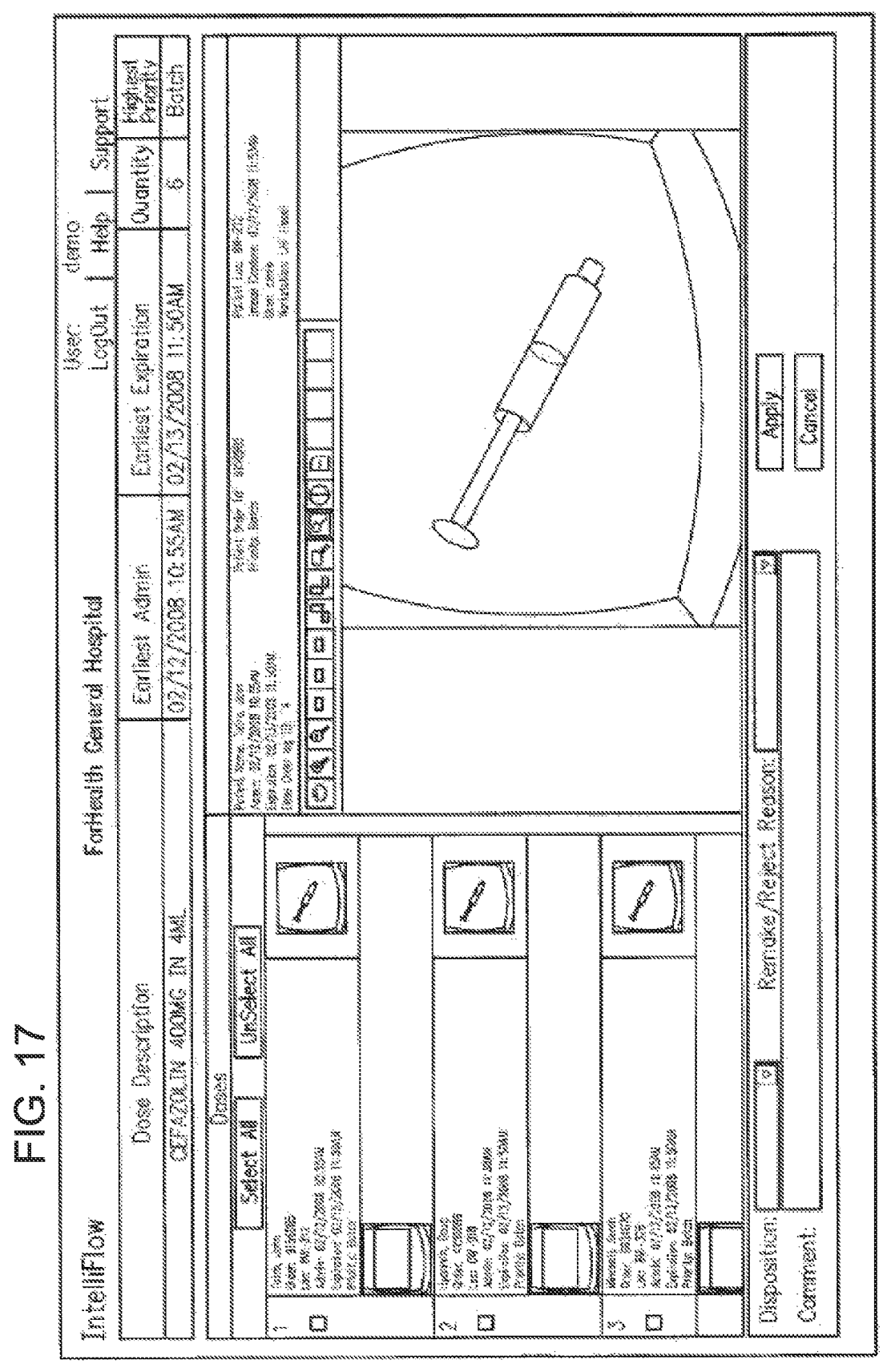

FIGS. 16 and 17 show an embodiment of a user interface for depicting various images that can be selected by a pharmacist in order to view a final dose order, in this case a syringe filled with medication. Different angles and different views are available to the pharmacist, as well as information that has been captured in other ways such as by scanning or weighing steps, if called for in the recipe at the workstation that prepared the final dose being inspected.

Preferably, the local server 330 includes web services or a communication module that enables the data records associated with the dose order and its production to be viewed through a conventional web-browser program. As such, the pharmacist no longer has to be physically within the pharmacy to inspect and verify dose orders and ultimately either approve and release the dose order or reject the dose order. The opportunities that this system presents are varied and great. For example, a number of pharmacies can subscribe to a service where pharmacists inspect and verify dose orders from a remote location, either all the time or after the close of normal business hours. In addition, when the drug orders are prepared by automated drug preparation devices as opposed to pharmacy clerks, the inspection and verification process can be outsourced to one or more pharmacists who review and verify the dose orders.

In addition, a panel of pharmacists can, at one or more remote locations, review the dose orders that have been prepared by a number of different workstations (both automated and manual), regardless of the location of such workstations. Each pharmacist can review all of the digital records and stored information as described above as part of the inspection process and then can approve the dose order for release if the pharmacist concludes that the dose order was properly prepared. The approval process can comprise messages communicated through the portal, e.g., a web-browser application such that the pharmacist simply logs into the system and approves particular orders by mouse-clicks, keystrokes, and other conventional inputs that are forwarded to the local server that was the source of that particular dose order. A conventional login process with password and optionally further user-authentication ensures that the pharmacist's identity is verified before providing access to the pharmacist to any dose order information. The system can be designed so that for each dose order, the pharmacist must enter a unique identifier, such as a password, in order to release the drug. The date and time of the inspection and release or rejection of the dose order is also logged. Optionally, this information can be associated with the dose order record so that the approval stage is saved together with the processing steps to fill the dose order. In this manner, a record of which pharmacist has approved a particular dose order can be saved.

It will be appreciated that an entity can be formed in which pharmacist-members span the world in different time zones so as to have a pharmacist available regardless of the time of day to inspect and release or reject a particular dose order. The pharmacists can thus be part of an organization or a corporation that offers this service to different pharmacies across the globe. To accommodate different languages, the software can be configured to offer the dose order information in different languages, which can be selected in a pull down menu on a screen, such as a login screen.

Figure 18:
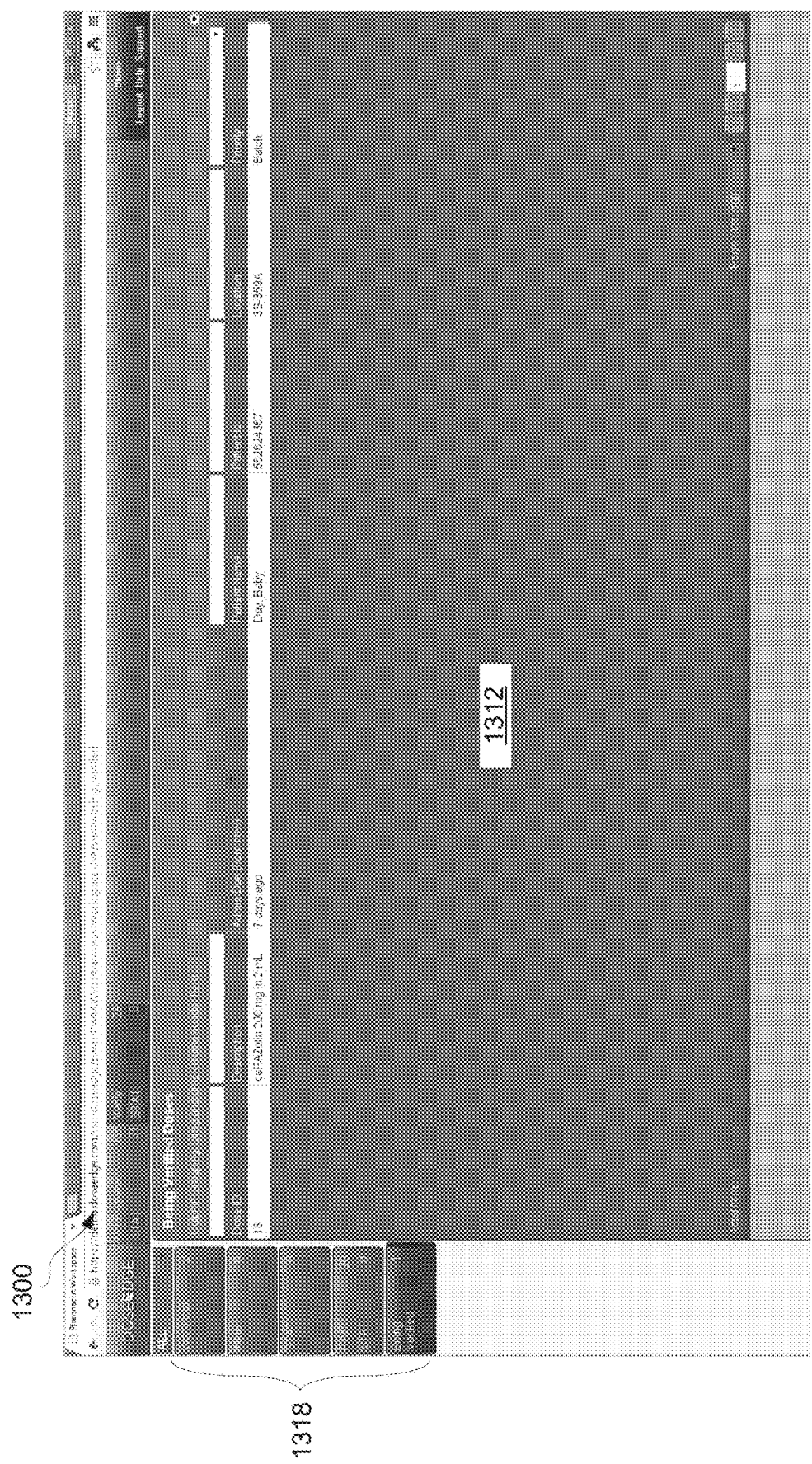
FIGS. 18, 19A, 19B, and 20 depict an embodiment of the user interface of the pharmacy workflow management application utilized by a pharmacist when reviewing a dose.

With further reference to FIG. 18, the dose order management tool 1300 may allow for a user to view and/or modify who has control over a dose order undergoing verification. For example, when a user selects a dose order record that has been prepared in order to verify the dose order, the dose order status may be changed to "at verification" or "claimed" to indicate that the dose is being verified by a user. However, under certain scenarios, the user may become distracted, be called away from the terminal at which verification is being performed, or otherwise be disposed such that the dose being verified remains in the claimed status without further action being taken with respect to the dose order. It may be beneficial to allow for another user to obtain control of the dose order record being verified such as for example, when a dose order associated with the verified dose order record is approaching administration time or if the dose order has a STAT priority or the like. Accordingly, with respect to FIG. 18, when tab 1316 is selected to display dose is awaiting verification, a secondary filter 1318 associated with doses being verified may be displayed to present a dose order record listing 1312 populated with dose order records with a claimed status. That is, upon selection of the being verified filter 1318, the dose order record listing 1312 may be populated with doses that are undergoing verification.

Figure 19A:
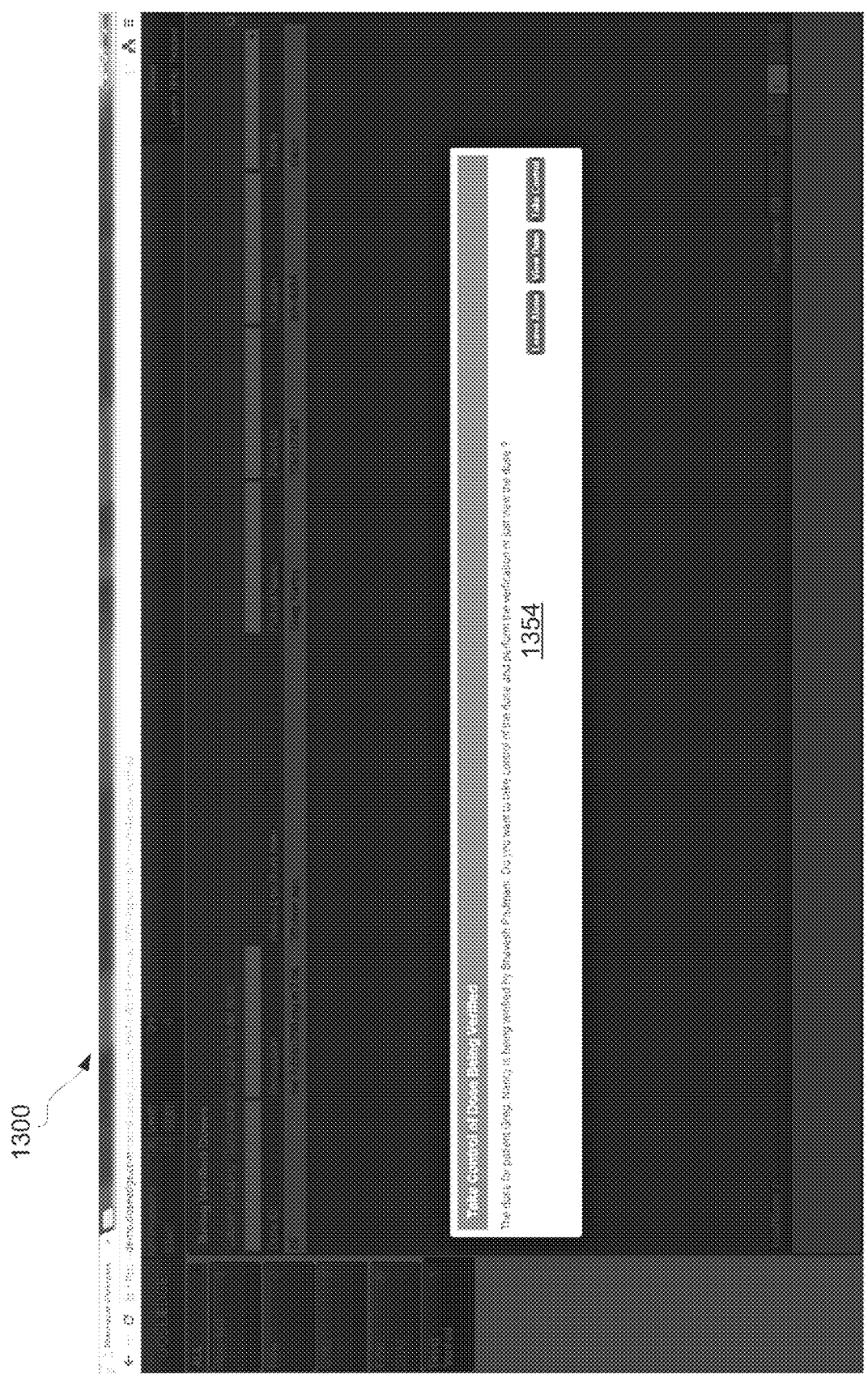

In turn, upon selection of a dose being verified by another user, a verification control dialog box 1354 may be displayed to the user as shown in FIG. 19A. The verification control dialog box 1354 may display to a user an indication of the other user who currently has control of (i.e., is verifying) the dose. The verification control dialog box 1354 may in turn include a number of controls (e.g., buttons) that provide for actions to be taken with respect to the dose being verified. For example, a user may select to leave the dose in the control of the other user by selection of the "leave alone" button. The user may also view details of the dose by selecting the "view dose" button. Finally the user may modify the control over the dose. In an embodiment, a control may be provided that allows a user to revoke the control over the dose from another user. Furthermore, as shown in FIG. 19A, a user may take control of the dose being verified by the other user by selecting the "take control" button.

Figure 19B:

Upon selection of the "take control" button, a user may obtain control over the verification of the dose from the other user. In turn, a dose verification screen 1360 for the user to control the dose may be shown as depicted in FIG. 19B. Specifically, a dose control indicator 1356 may provide an indication that indicates the user has taken control over the verification of the dose. Selection of the dose control indicator 1356 may provide details regarding the user and an expiration time corresponding to the time at which the user's control over the dose may cease in a dose control information window 1358. Correspondingly, a dose verification screen 1360 of the other user may be updated such that the dose control indicator 1356 of the other users modified to indicate the user no longer controls the verification of the dose. Furthermore, the dose control information window 1358 may be updated to display to the other user name user who is currently controlling the dose.

After doses are prepared, the resulting physical dose may be tracked during the dose sorting and distribution 460 as shown in FIG. 4. That is, once the dose corresponding to the dose order is prepared, the resulting dose may be labeled, preferably at the dose preparation station so that the label is in close proximity to the prepared dose (as opposed to the conventional practice of centralized printing of all of the labels for dose-orders that enter the pharmacy. The association between the dose, the dose order, and the dose order record may be a result of linking the interrogation of a scannable element to the dose order record. A code supported by or secured to the dose itself and a code associated with a bin at the dosage form's current location can both be interrogated and then that information uploaded to a database to provide information regarding the whereabouts of the dose within the pharmacy. For example, the codes can be bar codes and can be sensed using a reader such as, for example, a bar code scanner. The particular scanner or reader used and the manner of scanning can be varied within the context of the invention to suit the requirements of a given implementation. Thus, for example, the code can be an optically scannable bar code or an interrogatable code such as an RFID tag that is supported in lieu of or in addition to bar codes, plain text, or other codes. The terms scanner, scanning, and scannable and/or reader, reading, or readable are intended to include wireless interrogation or passive data reception whether they are based on an optical read, a radio frequency interrogation or an interrogation in some other frequency band, or a form of passive wireless data reception. More generally, the codes in scannable or readable form are referred to as "tags." As the dose progresses through the process of preparing the dose, the dose and/or additional tags associated with various locations or processes can be scanned to track the dose through the preparation process. The process of scanning a tag associated with the dose to change the dose's status and/or location information may be referred to as a scan event. Some scan events may also be triggered scan events that function to change the status of the dose in the preparation process in response to a scan. For example, when the technician selects a dose to prepare, a dose label may be printed for the dose. The printed dose label may have a tag associated with the dose order. Scanning the dose order tag on the label may be a precursor in the protocol to initiate the preparation of the dose and my simultaneously trigger the status of the dose to change from, for example, "pending" to "in process."

The workflow process described herein may include a "kitting" function that organizes work into appropriate kits, prints picking documents to assist the technician in locating and securing the appropriate drugs and supplies. Bar codes or the like can be used to verify the selected drugs and the workflow process includes issuing a kit report that tracks the work into and through the IV room or other room.

Additionally, scanning of tags associated with a dose may allow a plurality of dose orders may be aggregated to define a transport collection. For example, a transport collection may be identified for a specific final destination within a facility for more efficient transport of doses to the final destination in the facility. As such, the final destination may, but is not required to, correspond to a physical location within a hospital or other care facility. In this regard, verified doses may be scanned to identify the dose order for the dose. Subsequently, a transport collection (e.g., a tag or other machine readable identifier) may be scanned to associate the dose order with the transport collection. In this regard, when the transport collection undergoes a scan event (e.g., corresponding to a change in location of transport collection), all dose order records that are associated with transport collection may be updated without requiring each dose order record and transport collection to be scanned.

The transport collections may be associated with the final destination. In this regard, prior to association of a dose order with transport collection, one or more portions of dose metadata may be scrutinized determine the appropriateness of the dose order being added to the transport collection. For example, a transport collection may be established that is to be distributed to a predetermined location within a hospital. As an example, a transport collection may be defined corresponding to a fourth floor nursing station. In this regard, if the dose order record has dose metadata associated with a corresponding dose order record data field that indicates the dose order is not to be transported to the fourth floor nursing station, a transport collection rule may prevent association of the dose order with the transport collection rule. In this regard, the rule may scrutinize dose order metadata associated with a dose order to determine the appropriateness of the dose order records in relation to the transport collection. As such, a dose order record that includes dose order metadata not associated with acceptable metadata for the dose order record may be disallowed from being associated with the transport collection. The metadata scrutinized by the transport collection rule may be any appropriate portion of metadata and not simply limited to a location provided in the dose order data. For example, it may be recognized that a location may be unacceptable for handle hazardous doses such as chemotherapy doses or the like. In this regard, any portion of dose order metadata regarding the dose order (e.g., drug identifiers like) may be utilized to define transport collection rules.

In connection with the tracking of the dose in the pharmacy, the pharmacy workflow management application 114 is further capable of responding to any status inquiries concerning a given dose order with order status (e.g., "unprocessed," "in-progress at {selected workstation}," "processed" and the like) and optionally a location (e.g., in bin A, on cart B, in pediatric ward, etc.). The pharmacy workflow management application 114 is also capable of monitoring and tracking the prepared dose through to its delivery with additional status information (e.g., dispensation to patient {X}), as discussed with reference to FIG. 21.

In FIG. 21 a process flow is illustrated that commences when a workstation identifies a particular dose as having been completed, as indicated at terminator 800. The local database is updated with completion information at step 805, and this provides status information that can be referenced by persons outside of the pharmacy in response to a status inquiry and by the system in managing the distribution of subsequent dose orders. The identification preferably associates a unique identifier with the dose. The database record associated with the identified dose can be marked as completed. Alternatively, various other subsystems can be notified of the completion of the dose. For example, a storage subsystem that tracks medication that is "on-hand" can be updated with the prepared dose's record. Additionally, a delivery subsystem can be notified that the prepared dose is completed and ready for delivery to its destination. At a later time, for instance, according to a schedule, the information in the local database can be uploaded to a central server 390 that can be configured to communicate with the respective local databases of multiple pharmacy systems.

With continued reference to FIG. 21, in step 830, if the pharmacist approves the dose order, then the dose order is released in step 840 as described above. On the other hand, if at step 830 the pharmacist does not approve the dose order based on the information presented to the pharmacist, then the dose order is rejected and the original order is added back the dose order queue at step 850 for preparation anew. At step 860, the local database and the situation board are updated to reflect whether the dose order was released or not. At a later time, the local database can communicate the completed dose information including any dose-approvals and dose-rejections from the local server 330 to the central server 390.

As may be appreciated, dose tracking takes a number of forms. The situation board 400 provides one manner of dose tracking because it maintains a high level view of the work being performed in the pharmacy and because is configured to immediately instruct an observer regarding any incomplete work. Moreover, color coding on the situation board can immediately identify the amount of work that is pending preparation, under preparation or prepared but not yet checked out by a pharmacist (i.e., orders not yet approved for release. Dose tracking is also provided at each step in the dose preparation process, including without limitation, the selection and preparation of the ingredients, pharmacist checking, removal from the IV room for delivery to a patient, and the actual delivery of the dose to the floor. Each of these steps is part of the workflow process that is tracked in the system managed by the server 330. As well, there is a dose query function that permits any authorized user to probe the database to discover the current status of any particular dose or group of doses. Also, the situation board maintains alarms for doses that are due and also tracks doses whose preparation must be delayed because of limited stability in solution.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A system for preparing medication doses, the system comprising:

a central server of a healthcare information management system, the central server configured to:
   receive permission data that includes permission identification for at least one support user and verification users regarding permitted access to a healthcare information management application based on specified roles for the at least one support user and the verification users, one of the specified roles corresponding to dose preparation verification,
   apply a hash function to the permission data to generate a hash value,
   compare the hash value to a previous hash value of previous permission data that was last transmitted to dose preparation work stations, and
   when the hash value does not match the previous hash value, transmit the permission data to the dose preparation work stations to update the previous permission data;
an individual dose preparation work station that is located remotely from the central server, the individual dose preparation work station including
   a touchscreen for displaying information related to preparing medication doses in one or more user interfaces,
   at least three of a reconstitution module, a barcode scanner, a camera, or a scale for preparing medication doses,
   a processor communicatively coupled to the touchscreen and the at least three of the reconstitution module, the barcode scanner, the camera, or the scale,
   a memory storing instructions that are configured to be executed by the processor for executing a pharmacy workflow management application for use in the preparation of medication doses for administration to a patient at the individual dose preparation work station, wherein the pharmacy workflow management application is in operative communication with the central server, and wherein the pharmacy workflow management application executes the healthcare information management application, and
   a local network communication device in operative communication with the central server to receive the permission data from the central server, wherein the memory further includes a non-transitory computer-readable data structure that stores the permission data; and
a remote access terminal communicatively coupled to the central server via a network, the remote access terminal configured to receive the permission data from the central server and execute the healthcare information management application to at least:
   receive user authentication corresponding to a first verification user,
   use the permission data to determine that the received user authentication corresponds to the dose preparation verification role,
   after authenticating the first verification user, receive a request to take control of a dose verification of a medication dose prepared by the individual dose preparation work station, the dose verification currently being performed by a second verification user at another remote access terminal,
   after receiving the request to take control, cause the other remote access terminal to remove access to the dose verification for the second verification user, and display verification information related to the dose verification to enable the first verification user to complete the dose verification of the medication dose, wherein the instructions of the memory specify operations performed by a permission module of the pharmacy workflow management application at the individual dose preparation work station, wherein the instructions cause the permission module to receive a request for access by the at least one support user, the request for access associated with dose preparation, and grant the at least one support user access to the healthcare information management application for dose preparation based on the permission data, wherein responsive to receiving access to the healthcare information management application, the instructions cause the permission module to enable the at least one support user to prepare the medication dose with the individual dose preparation work station by accessing a dose preparation protocol for the medication dose that is displayed via the one or more user interfaces and using the at least three of the reconstitution module, the barcode scanner, the camera, or the scale in conjunction with the dose preparation protocol to prepare the medication dose, and wherein the instructions cause the permission module to prevent the at least one support user from preparing the medication dose with the individual dose preparation work station when the permission data does not support the request for access by the at least one support user based on the specified role for the at least one support user by preventing access to the one or more user interfaces and preventing the at least one support user from accessing the dose preparation protocol and using the reconstitution module, the barcode scanner, the camera, or the scale.

2. The system of claim 1, wherein the permission module is operative to provide confirmation of receipt of the permission data to the central server.

3. The system of claim 2, wherein the confirmation of receipt of the permission data comprises a checksum calculated by the permission module in relation to received permission data.

4. The system of claim 1, wherein the permission data received from the central server comprises a subset of permission data that is modified since the previous transmission of permission data to the local network communication device.

5. The system of claim 1, wherein the local network communication device transmits to the central server an error regarding the permission data received at the pharmacy workflow management application.

6. The system of claim 1, wherein the local network communication device receives the permission data from the central server at regular periodic intervals.

7. The system of claim 1, further comprising:
a log module that is operative to log activity of the at least one support user at the individual dose preparation work station in a human readable format for review by a human user at the individual dose preparation work station.

8. The system of claim 7, wherein the log module logs changes made to the non-transitory computer-readable data structure regarding the permission data.

9. The system of claim 7, wherein the log module is in operative communication with the local network communication device and logs data regarding the receipt of the permission data from the central server.

10. The system of claim 7, wherein the log module logs access data regarding access by the at least one support user to the individual dose preparation work station.

11. The system of claim 10, wherein the access data comprises an identity of the at least one support user accessing the central server and an indication of a resource that is accessed by the at least one support user.

12. The system of claim 11, wherein the at least one support user is a remotely located support user at the central server.

13. The system of claim 11, wherein the identity of the at least one support user comprises a user name of the at least one support user.

14. The system of claim 13, wherein the indication of the resource accessed by the at least one support user comprises an indicator of whether the resource included protected health information (PHI).

15. The system of claim 14, wherein the indicator of whether the resource included PHI is based on a resource flag indicative of whether the resource includes PHI.

16. The system of claim 15, wherein the resource comprises a report, and wherein the resource flag indicative of whether the resource includes PHI is dynamically generated based on whether the report included a data class defined as containing PHI.

17. The system of claim 1, wherein the permission data is correlated to a user name regarding the at least one support user and the user name is associated with a password.

18. The system of claim 17, wherein access to a resource at the pharmacy workflow management application requires provision of a correct user name and password combination, and wherein the access to the resource at the pharmacy workflow management application or the central server is defined by the permission identification associated with the user name.

19. The system of claim 18, wherein the user name corresponds to a single individual user.

20. The system of claim 19, wherein the non-transitory computer-readable data structure stores at least one support user group, the at least one support user group having permission data applicable to each member of the at least one support user group, and wherein the at least one support user is a member of the at least one support user group such that the user name of the at least one support user is associated with the at least one support user group.

21. The system of claim 20, wherein the at least one support user group is provided with task specific permission identification.

22. The system of claim 1, wherein the permission identification defines a data class accessible by the at least one support user.

23. The system of claim 22, wherein the data class is defined as either one of data having protected health information (PHI) or not having PHI.

24. The system of claim 23, wherein the permission identification identifies that the at least one support user is authorized to only access the data class not having PHI.

25. The system of claim 23, wherein the permission identification identifies that the at least one support user is authorized to access the data class having PHI.

26. The system of claim 18, wherein the permission module at the individual dose preparation work station determines whether access to the resource is granted to the at least one support user based at least on receipt of a correct password corresponding to the user name and the permission identification in the permission data regarding the at least one support user.

27. The system of claim 1, wherein the central server and the pharmacy workflow management application are unaffiliated.

28. The system of claim 27, wherein the at least one support user is remote from the pharmacy workflow management application.

\* \* \* \* \*